(12) United States Patent
Wan et al.

(10) Patent No.: US 10,550,063 B2
(45) Date of Patent: Feb. 4, 2020

(54) PROCESSES FOR PREPARING 2,5-DICHLOROPHENOL

(71) Applicant: Monsanto Technology LLC, St. Louis, MO (US)

(72) Inventors: Kam-To Wan, Town and Country, MO (US); John H. Ahn, Maryland Heights, MO (US); John Wang, St. Louis, MO (US); Don Probst, St. Peters, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/516,105

(22) PCT Filed: Oct. 2, 2015

(86) PCT No.: PCT/US2015/053715
§ 371 (c)(1),
(2) Date: Mar. 31, 2017

(87) PCT Pub. No.: WO2016/054506
PCT Pub. Date: Apr. 7, 2016

(65) Prior Publication Data
US 2017/0247310 A1    Aug. 31, 2017

Related U.S. Application Data

(60) Provisional application No. 62/058,886, filed on Oct. 2, 2014, provisional application No. 62/091,995, filed on Dec. 15, 2014.

(51) Int. Cl.
*C07C 51/367* (2006.01)
*C07C 37/00* (2006.01)
*C07C 51/00* (2006.01)

(52) U.S. Cl.
CPC ........... *C07C 51/367* (2013.01); *C07C 37/00* (2013.01); *C07C 51/00* (2013.01)

(58) Field of Classification Search
None
See application file for complete search history.

(56) References Cited

U.S. PATENT DOCUMENTS 2,480,817 A    8/1949    Warren
2,651,659 A    9/1953    Warren et al.
(Continued)

FOREIGN PATENT DOCUMENTS

| EP | 0975569 B1 | 9/2003 |
| RU | 2192308 C | 11/2002 |
| WO | 2013123299 A1 | 8/2013 |

OTHER PUBLICATIONS

Abello et al. Applied Catalysis A: General 364 (2009) 191-198.*
(Continued)

*Primary Examiner* — Clinton A Brooks
(74) *Attorney, Agent, or Firm* — Stinson LLP; Erin C. Robert

(57) ABSTRACT

Processes for producing 2,5-dichlorophenol and 3,6-dichloro-2-methoxybenzoic acid are described. Various processes for isomerizing 2,4-dichlorophenol over a zeolite catalyst to form 2,5-dichlorophenol are provided. Processes for preparing 2,5-dichlorophenol including hydroxylating 1,4-dichlorobenzene are also described. The present invention also relates to processes for producing 3,6-dichloro-2-methoxybenzoic acid.

42 Claims, 12 Drawing Sheets

(56) References Cited

U.S. PATENT DOCUMENTS

| | | | |
|---|---|---|---|
| 2,708,209 | A | 5/1955 | Nicolaisen et al. |
| 3,013,054 | A | 12/1961 | Richter |
| 3,462,498 | A | 8/1969 | Lowe et al. |
| 3,726,929 | A | 4/1973 | Payne et al. |
| 4,418,235 | A | 11/1983 | Haag et al. |
| 4,568,777 | A | 2/1986 | Baltes et al. |
| 5,055,623 | A | 10/1991 | Gubelmann et al. |
| 5,110,995 | A | 5/1992 | Kharitonov et al. |
| 5,118,876 | A | 6/1992 | Zinnen et al. |
| 5,648,562 | A | 7/1997 | Henrick |
| 5,672,777 | A | 9/1997 | Kharitonov et al. |
| 5,756,861 | A | 5/1998 | Panov et al. |
| 6,156,938 | A | 12/2000 | Sobolev et al. |
| 6,166,268 | A | 12/2000 | Kuehnle et al. |
| 6,274,776 | B1 | 8/2001 | Henrick et al. |
| 6,323,377 | B1 | 11/2001 | Scheuerman et al. |
| 6,388,145 | B1 | 5/2002 | Kustov et al. |
| 6,414,197 | B1 | 7/2002 | Kustov et al. |
| 6,476,277 | B2 | 11/2002 | Vogel et al. |
| 6,548,718 | B2 | 4/2003 | Murray et al. |
| 6,573,413 | B2 | 6/2003 | Chernyavsky et al. |
| 6,586,624 | B1 | 7/2003 | Henrick et al. |
| 6,900,358 | B2 | 5/2005 | Hamilton, Jr. |
| 7,259,121 | B2 | 8/2007 | Schewefer et al. |
| 8,513,150 | B2 | 8/2013 | Wu |

OTHER PUBLICATIONS

Corma, A., "Inorganic Solid Acids and Their Use in Acid-Catalyzed Hydrocarbon Reactions," 1995, Chem Rev, 95:559-614, 56 pages.

Rodkin, M.A., et al., "Room-Temperature Oxidation of Hydrocarbons Over FeZSM-5 Zeolite," 2000, Studies in Surface Science and Catalysis, 130: 875-880, 6 pages.

Syme, A., "The Production of Phenoxy Herbicides," Production of Chemicals, Chemical Process in New Zealand, New Zealand Institute of Chemistry, Downloaded Sep. 2, 2014, 10 pages.

Venuto, P.B., "Organic Catalysis Over Zeolites: A Persepective on Reaction Paths Within Micropores," 1994, Microporous Materials 2, 297-411, 115 pages.

Yamada, Y., "Dicamba (240) Draft" 2010, Food and Agriculture Organization of the United Nations, 939-1094.

International Search Report dated Dec. 18, 2015 in International Application No. PCT/US2015/053715, 12 pages.

\* cited by examiner

US 10,550,063 B2

PROCESSES FOR PREPARING 2,5-DICHLOROPHENOL

REFERENCE TO RELATED APPLICATIONS

The present application is the 371 National Stage Application of International Patent Application Serial No. PCT/US2015/053715, filed Oct. 2, 2015, which claims the benefit of U.S. Provisional Application Ser. No. 62/058,886, filed Oct. 2, 2014 and U.S. Provisional Application Ser. No. 62/091,995, filed Dec. 15, 2014, the entire contents of which are incorporated herein by reference.

FIELD OF THE INVENTION

The present invention generally relates to processes for producing 2,5-dichlorophenol. Various processes in accordance with the present invention include isomerizing 2,4-dichlorophenol over a zeolite catalyst to form 2,5-dichlorophenol. The present invention further relates to processes for preparing 2,5-dichlorophenol including hydroxylating 1,4-dichlorobenzene. The present invention also relates to processes for producing 3,6-dichloro-2-methoxybenzoic acid.

BACKGROUND OF THE INVENTION

Dichlorophenols are useful intermediates in the preparation of a variety of chemical products. In particular, certain herbicides are prepared from dichlorophenols. For example, 2,4-dichlorophenoxyacetic acid (2,4-D) can be prepared from 2,4-dichlorophenol. See U.S. Pat. Nos. 2,480,817 and 2,651,659. Also, 3,6-dichloro-2-methoxybenzoic acid (dicamba) can be prepared from 2,5-dichlorophenol. See, for example, U.S. Pat. Nos. 3,013,054 and 5,648,562.

With the introduction of dicamba-tolerant traits in various crop plants, dicamba is becoming an increasingly important herbicide. However, difficulties remain in processes for producing dicamba. High raw material cost, low process conversions and selectivities, and large amounts of wastes are problems that remain in these processes. In addition, the starting material 2,5-dichlorophenol is expected to significantly contribute to high raw material costs. Accordingly, there remains a need for improved processes for the production of critical intermediates to dicamba including 2,5-dichlorophenol to improve process economics.

U.S. Pat. No. 4,568,777 proposes a process for the isomerization of mono- or dichlorophenols, including 2,4-dichlorophenol, using certain types of zeolite catalysts. However, this process failed to achieve a high selectivity for the 2,5-dichlorophenol isomer. Thus, there remains a need for commercially feasible processes that are highly selective for 2,5-dichlorophenol, which reduce raw material costs and waste products.

SUMMARY OF THE INVENTION

Briefly, in some aspects, the present invention relates to processes for producing 2,5-dichlorophenol comprising contacting a feed gas or a liquid comprising 2,4-dichlorophenol with a zeolite catalyst in acid form in an isomerization zone to isomerize at least a portion of the 2,4-dichlorophenol to 2,5-dichlorophenol. In various processes, the zeolite catalyst has a $SiO_2/Al_2O_3$ mole ratio of no greater than about 35:1. In various processes, the zeolite catalyst comprises a desilicated zeolite catalyst having a $SiO_2/Al_2O_3$ mole ratio of no greater than about 80:1. In various processes, the desilicated zeolite catalyst has a meso-macro pore volume (>20 Å to 2500 Å) that is at least about 50%, at least about 75%, at least about 100%, at least about 125%, at least about 150%, at least about 175%, at least about 200%, at least about 225%, at least about 250%, at least about 275%, or at least about 300% greater than the meso-macro pore volume of the initial zeolite catalyst before desilication. In various processes, the zeolite catalyst has a meso-macro pore volume that is at least about 0.15 $cm^3/g$, at least about 0.175 $cm^3/g$, at least about 0.2 $cm^3/g$, at least about 0.225 $cm^3/g$, or at least about 0.25 $cm^3/g$. In various processes, the feed comprises 2,4-dichlorophenol further comprises water (e.g., steam). In various processes, the feed comprising 2,4-dichlorophenol further comprises 3,4-dichlorophenol. In various processes, the feed comprising 2,4-dichlorophenol further comprises 2,5-dichlorophenol and 3,4-dichlorophenol. Also, various processes further comprise suspending contact of the feed comprising 2,4-dichlorophenol with the zeolite catalyst and contacting the zeolite catalyst with steam at a temperature from about 250° C. to about 375° C. to rejuvenate the catalyst.

In other aspects, the present invention relates to processes for producing 2,5-dichlorophenol comprising hydroxylating 1,4-dichlorobenzene with an oxidizing agent in the presence of a first zeolite catalyst in a hydroxylation zone to form a hydroxylation reaction product comprising 2,5-dichlorophenol and 2,4-dichlorophenol; separating at least a portion of the 2,4-dichlorophenol from the hydroxylation reaction product to form a fraction comprising 2,4-dichlorophenol; and contacting the fraction comprising 2,4-dichlorophenol with a second zeolite catalyst in acid form in an isomerization zone to isomerize at least a portion of the 2,4-dichlorophenol to 2,5-dichlorophenol.

In further aspects, the present invention relates to processes for producing 3,6-dichloro-2-methoxybenzoic acid comprising carboxylating at least a portion of the 2,5-dichlorophenol prepared in accordance various process described herein to produce 2-hydroxy-3,6-dichlorobenzoic acid and methylating/saponification or selective methylating the 2-hydroxy-3,6-dichlorobenzoic acid to 3,6-dichloro-2-methoxybenzoic acid.

Other objects and features will be in part apparent and in part pointed out hereinafter.

DESCRIPTION OF THE PREFERRED EMBODIMENTS

Figure 1:
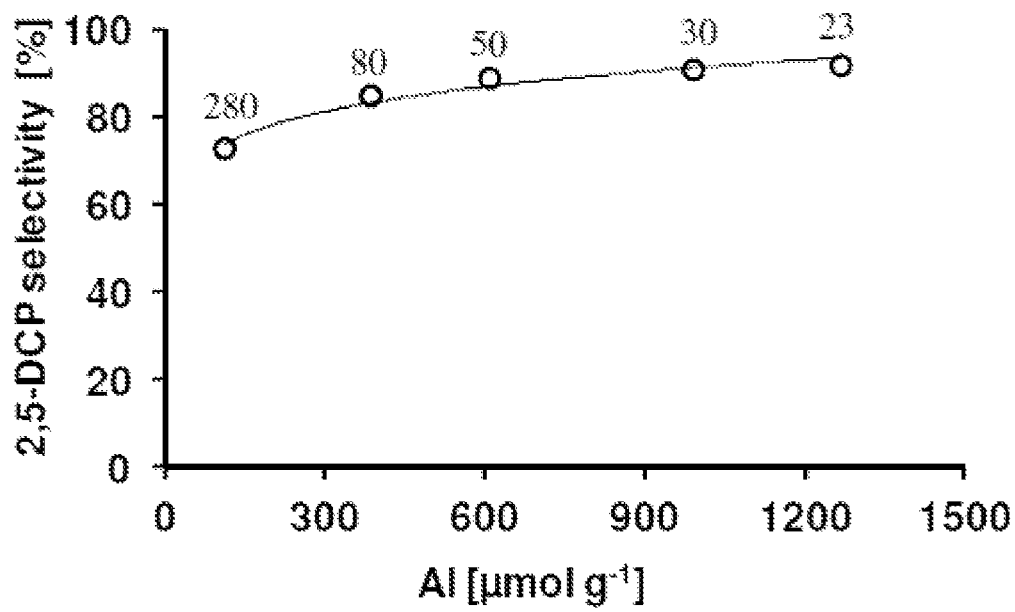
FIGS. 1-5 present various results from the experiments described in Example 2.
Figure 2:
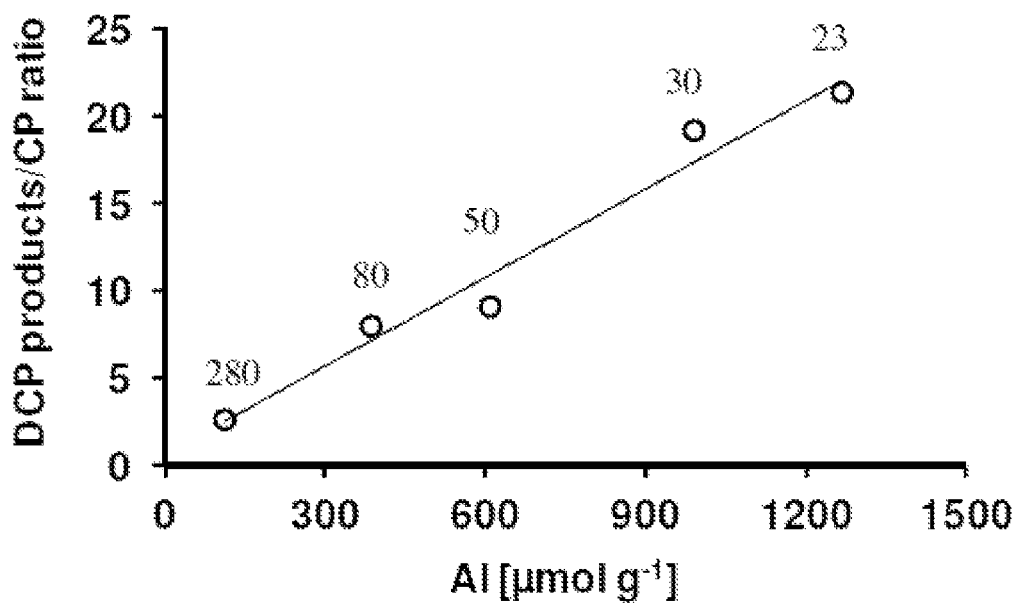
Figure 3:
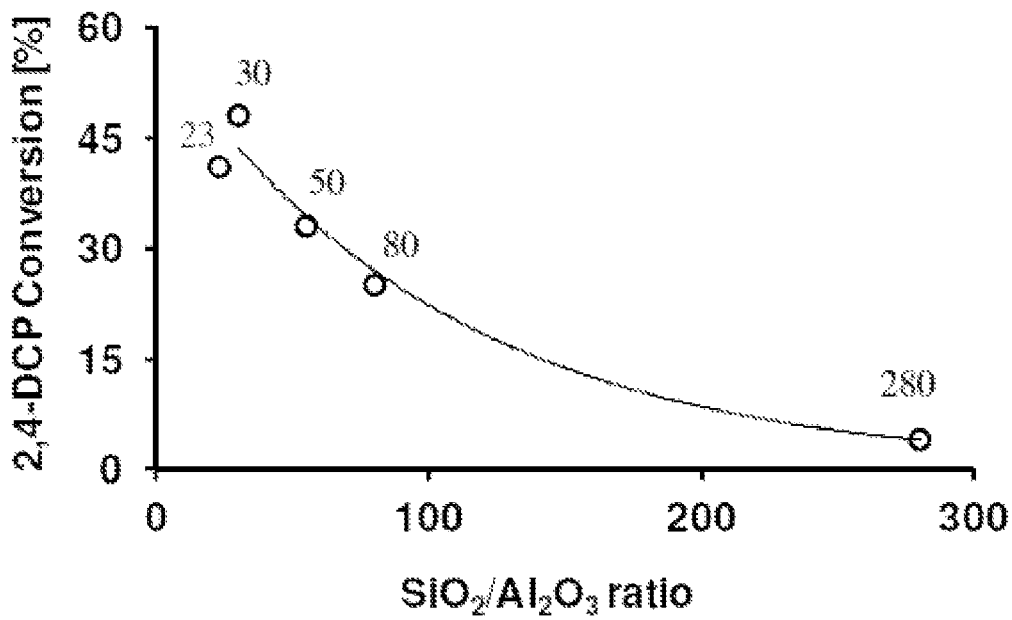
Figure 4:
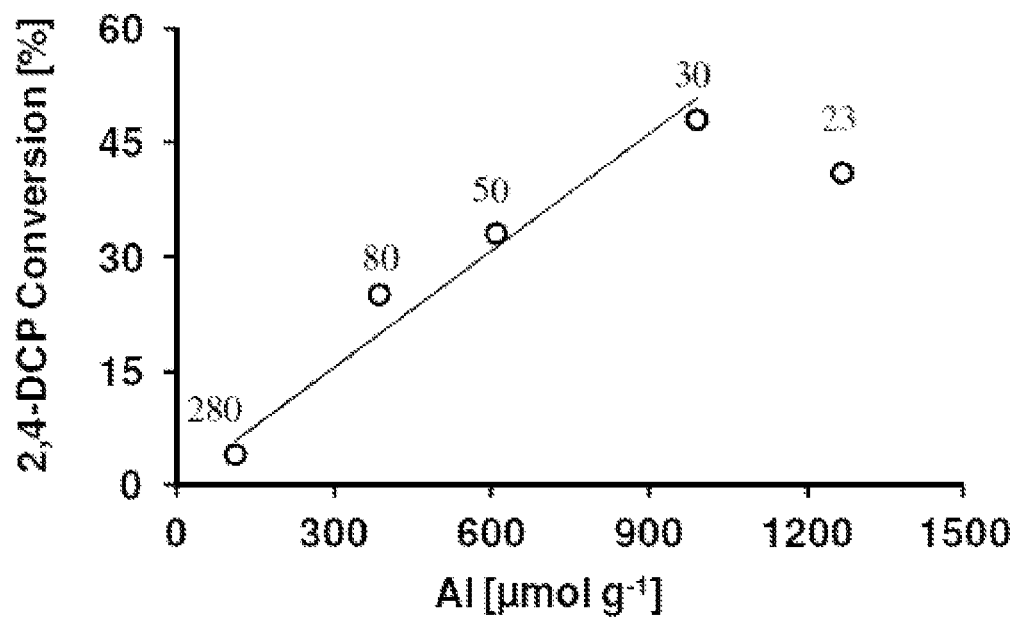
Figure 5:
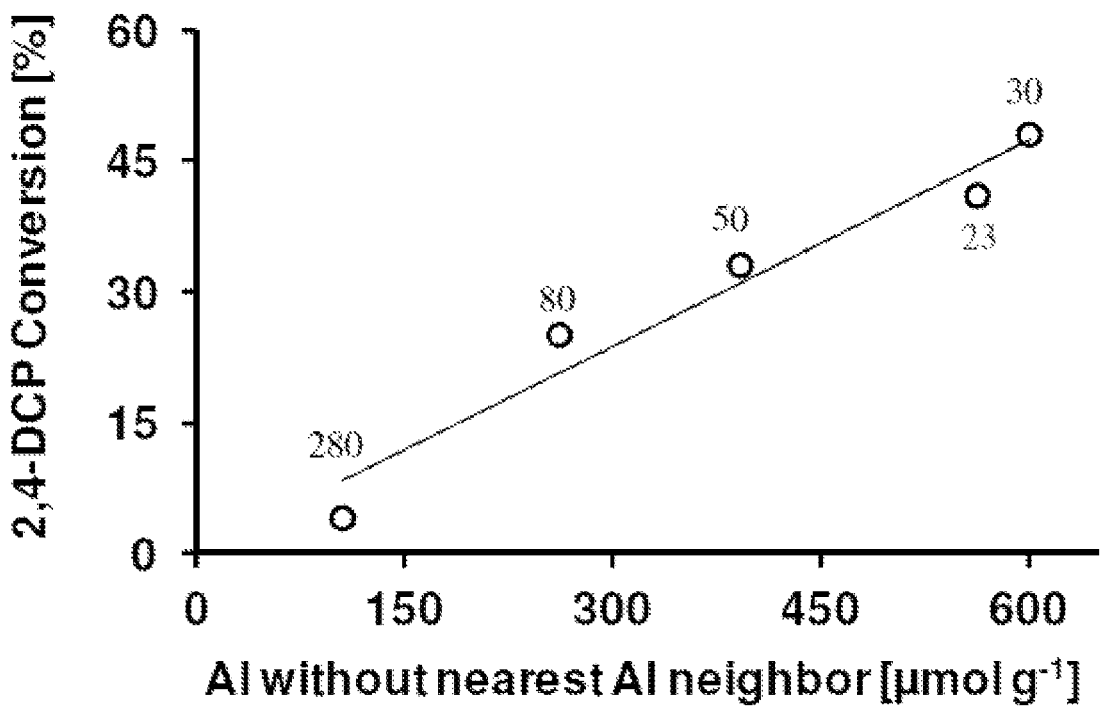

Various aspects of the present invention relate to processes for producing 2,5-dichlorophenol. Other aspects of the present invention relate to processes for producing 3,6-dichloro-2-methoxybenzoic acid.

One aspect of the present invention is directed to processes for the isomerization of 2,4-dichlorophenol that are highly selective for 2,5-dichlorophenol. Processes that are highly selective for 2,5-dichlorophenol reduce the amount of waste products such as monochlorophenols and 3,4-dichlorophenol, which require separation from the product and disposal or further processing to recycle. Thus, processes in accordance with the present invention with improved selectivity for 2,5-dichlorophenol significantly enhance process economics.

Another aspect of the present invention is directed to processes for the isomerization of 2,4-dichlorophenol with improved yield of 2,5-dichlorophenol. Processes that provide greater yields of 2,5-dichlorophenol advantageously increase production rates and reduce energy costs, which improves process economics. A further aspect of the present invention is directed to processes for the isomerization of 2,4-dichlorophenol that include an improved catalyst rejuvenation procedure that requires less energy input over conventional procedures, which also improves process economics.

Another aspect of the present invention relates to processes for the preparation of 2,5-dichlorophenol by hydroxylation of 1,4-dichlorobenzene. 1,4-Dichlorobenzene is a widely available industrial precursor used in the production of a variety of chemical products. Thus, using 1,4-dichlorobenzene as the starting material in the production of 2,5-dichlorophenol is expected to reduce reagent costs and improve process economics, especially for downstream processes that use 2,5-dichlorophenol as a key intermediate.

Yet another aspect of the present invention is directed to processes for the preparation of 2,5-dichlorophenol by hydroxylation of 1,4-dichlorobenzene that include separating at least a portion of 2,4-dichlorophenol produced in the hydroxylation reaction and isomerizing the 2,4-dichlorophenol to 2,5-dichlorophenol. Isomerizing 2,4-dichlorophenol by-product beneficially increases overall yield of the desired 2,5-dichlorophenol product.

A further aspect of the present invention is directed to processes for preparing 3,6-dichloro-2-methoxybenzoic acid from 2,5-dichlorophenol produced in accordance with various processes described herein.

Isomerization of 2,4-dichlorophenol

Various processes in accordance with the present invention for producing 2,5-dichlorophenol include isomerizing 2,4-dichlorophenol. Generally, the processes include use of a zeolite catalyst. In particular, isomerization processes in accordance with the present invention for producing 2,5-dichlorophenol comprise contacting a feed comprising 2,4-dichlorophenol with a zeolite catalyst in an isomerization zone to isomerize at least a portion of the 2,4-dichlorophenol to 2,5-dichlorophenol as shown below.

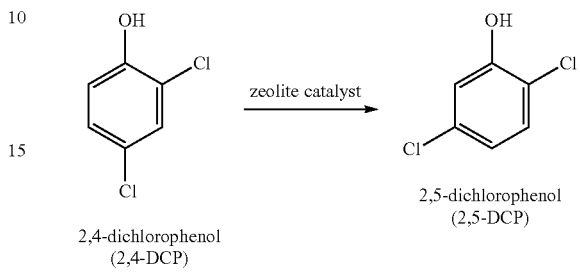

The feed comprising 2,4-dichlorophenol can be supplied to the isomerization zone as a gas or a liquid.

Suitable zeolite catalysts include medium and large pore size zeolites. Suitable medium pore size zeolites include pentasil zeolites such as ZSM-5 and ZSM-11 and large pore size zeolites include Beta zeolites and faujasite zeolites, such as zeolite Y. Thus, the zeolite catalyst can comprise at least one alumino-silicate zeolite selected from the group consisting of ZSM, Beta, Y zeolites, and mixtures thereof. In various isomerization processes of the present invention, the zeolite catalyst comprises a boron-promoted zeolite or a metal-promoted zeolite selected from the group consisting of titanium-silicates, alumino-silicates, iron-silicates, and gallium-silicate.

In various isomerization processes of the present invention, the zeolite catalyst comprises the acid form of the zeolite. For example, the zeolite catalyst includes the acid form of a medium pore size zeolite such as ZSM-5 zeolite (e.g., HZSM-5) or a large pore size zeolites including Beta zeolites and faujasite zeolite such as zeolite Y. An acid form (also known as proton form or hydrogen form) of a zeolite catalyst can be prepared by calcining an ammonium form of zeolite catalyst at elevated temperature. In various processes of the present invention, the zeolite can be calcined at a temperature at least about 450° C., at least about 500° C., at least about 510° C., at least about 520° C., at least about 530° C., at least about 540° C., or at least about 550° C. The calcination temperature can be in the range of from about 500° C. to about 1000° C., from about 500° C. to about 900° C., from about 500° C. to about 800° C., from about 500° C. to about 700° C., from about 520° C. to about 600° C., from about 530° C. to about 580° C., or from about 540° C. to about 560° C. Also, an acid form of a zeolite catalyst can also be prepared from a sodium form of zeolite. In this technique, the sodium form is subject to ion exchange with an ammonium salt to form the ammonium form of the zeolite. Subsequently, the ammonium form can be calcined to the acid form.

In various isomerization processes of the present invention, the mole ratio of $SiO_2/Al_2O_3$ is an important aspect of the zeolite catalyst. Surprisingly, applicants have discovered that when the $SiO_2/Al_2O_3$ mole ratio is no greater than about 35:1, then the selectivity of the catalyst for 2,5-dichlorophenol is significantly increased. Also, in some cases, when the $SiO_2/Al_2O_3$ mole ratio is no greater than about 35:1, the conversion of 2,4-dichlorophenol can advantageously be increased. Decreasing the $SiO_2/Al_2O_3$ mole ratio increases the relative amount of aluminum present in the zeolitic framework. Without being bound by theory, it is believed that the aluminum serves as acid sites for the isomerization. Accordingly, in various processes according of the present invention the zeolite catalyst can have a $SiO_2/Al_2O_3$ mole ratio of no greater than about 35:1. In certain processes, the zeolite catalyst can have a $SiO_2/Al_2O_3$ mole ratio of no greater than about 30:1.

It has been further discovered that in some instances decreasing the $SiO_2/Al_2O_3$ mole ratio lower than about 20:1 or about 23:1 reduces the activity of the catalyst. For example, it has been found that the conversion of 2,4-dichlorophenol is reduced when the $SiO_2/Al_2O_3$ mole ratio is lower than about 20:1 or lower than about 23:1 when compared to the conversion using a zeolite catalyst having a $SiO_2/Al_2O_3$ mole ratio at 30:1. Applicants believe that there are several possible aluminum (active site) distributions and locations in zeolitic frameworks, and these depend on the $SiO_2/Al_2O_3$ mole ratios as well as synthesis parameters of the zeolite. Without being bound by theory, applicants believe that the activity of the catalyst depends on the number of acid sites that are relatively "isolated" (or do not have neighboring or adjacent aluminum species), possibly because adjacent active sites increase the activation energy required for isomerization (from distorted bond angles, changing the ability to stabilize transition state) or these adjacent sites enhance adsorption of two reactant molecules, which creates additional steric hindrances for isomerization. Accordingly, in various processes of the present invention, the zeolite catalyst can have a $SiO_2/Al_2O_3$ mole ratio that is no greater than about 35:1, but is at least about 23:1 (i.e., from about 23:1 to about 35:1 or from about 23:1 to about 30:1).

In some isomerization processes of the present invention, applicants have found that a desilicated zeolite catalyst is highly selective and provides enhanced yields of 2,5-dichlorophenol. The desilication of zeolite catalysts can be carried out by leaching techniques with, for example, one or more solutions of NaOH. Heat can be applied during leaching (e.g., heating at 65-80° C.). The leaching procedure converts the acid (proton) form catalyst to a sodium form. Thus, the sodium form can be subjected to ion exchange with an ammonium salt such as $(NH_4)_2SO_4$ to form the ammonium form of the zeolite. Subsequently, the ammonium form can be calcined to the acid form (e.g., calcined in air at 550° C. for 24 hours to convert the zeolites to acid form (i.e., HZSM-5).

In processes employing a desilicated zeolite catalyst, the $SiO_2/Al_2O_3$ mole ratio of the zeolite can be greater than about 35:1. For example, the $SiO_2/Al_2O_3$ mole ratio of the zeolite can be as high as about 80:1, about 60:1, or about 55:1 (e.g., from about 23:1 to about 80:1; from about 23:1 to about 60:1; or from about 23:1 to about 55:1). It is believed that the desilication procedure enhances the meso-pore volume, but maintains the median pore width and micro-pore volume. Accordingly, desilicated zeolite catalysts exhibit a greater meso-macro pore volume which is defined herein as the volume attributable to pores having diameters that are greater than 20 Å and as large as 2500 Å. Although not entirely understood, it is believed that increasing of meso-pore volumes of the catalyst by desilication increases the concentration of accessible active acid sites. The significantly higher yield with desilicated catalyst suggested that the acid sites in the catalyst pore mouth region are predominantly responsible for a higher yield of 2,5-dichlorophenol in the isomerization of 2,4-dichlorophenol. The desilication procedure can increase the meso-macro pore volume (>20 Å up to 2500 Å) of the zeolite catalyst by at least about 50%, at least about 75%, at least about 100%, at least about 125%, at least about 150%, at least about 175%, at least about 200%, at least about 225%, at least about 250%, at least about 275%, or at least about 300% as compared to the meso-macro pore volume of the initial zeolite catalyst that has not been desilicated. Thus, another process for producing 2,5-dichlorophenol comprises contacting a feed comprising 2,4-dichlorophenol with a desilicated zeolite catalyst in acid form in an isomerization zone to isomerize at least a portion of the 2,4-dichlorophenol to 2,5-dichlorophenol, wherein the desilicated zeolite catalyst has a meso-macro pore volume (>20 Å up to 2500 Å) that is at least about 50%, at least about 75%, at least about 100%, at least about 125%, at least about 150%, at least about 175%, at least about 200%, at least about 225%, at least about 250%, at least about 275%, or at least about 300% greater than the meso-macro pore volume of the initial zeolite catalyst before desilication.

The desilicated zeolite catalyst can have a meso-macro pore volume (>20 Å up to 2500 Å) that is from about 50% to about 500%, from about 50% to about 400%, from about 50% to about 300%, from about 100% to about 500%, from about 100% to about 400%, from about 100% to about 300%, from about 200% to about 500%, from about 200% to about 400%, or from about 200% to about 300% greater than the meso-macro pore volume of the initial zeolite catalyst before desilication. For example, for a zeolite catalyst (e.g., H-ZSM-5) with an initial $SiO_2/Al_2O_3$ mole ratio of 55:1, the desilication procedure can increase the meso-macro pore volume (20 Å to 2500 Å) to at least about 0.15 cm³/g, at least about 0.175 cm³/g, at least about 0.2 cm³/g, at least about 0.225 cm³/g, or at least about 0.25 cm³/g. The meso-macro pore volume (20 Å to 2500 Å) of the desilicated zeolite catalyst can be from about 0.15 cm³/g to about 0.3 cm³/g, from about 0.175 cm³/g to about 0.3 cm³/g, from about 0.2 cm³/g to about 0.3 cm³/g, from about 0.225 cm³/g to about 0.3 cm³/g, or from about 0.25 cm³/g to about 0.3 cm³/g.

Regardless of any modifications to the zeolite catalyst, the zeolite catalyst can have a meso-macro pore volume that is at least about 0.15 cm³/g, at least about 0.175 cm³/g, at least about 0.2 cm³/g, at least about 0.225 cm³/g, or at least about 0.25 cm³/g. For example, the meso-macro pore volume of the zeolite catalyst can be from about 0.15 cm³/g to about 0.3 cm³/g, from about 0.175 cm³/g to about 0.3 cm³/g, from about 0.2 cm³/g to about 0.3 cm³/g, from about 0.225 cm³/g to about 0.3 cm³/g, or from about 0.25 cm³/g to about 0.3 cm³/g. Also, the $SiO_2/Al_2O_3$ mole ratio of the zeolite catalyst can be no greater than about 80:1, no greater than about 60:1, or no greater than about 55:1. For example, the $SiO_2/Al_2O_3$ mole ratio of the zeolite catalyst can be from about 23:1 to about 80:1; from about 23:1 to about 60:1; or from about 23:1 to about 55:1.

The specific surface area of the zeolite is determined according the BET method as described in S. Brunauer, P. H. Emmett, E. Teller, J. Am. Chem. Soc. 1938, 60, 309-331. Mean pore widths and pore volumes are determined in accordance with the BJH method described in E. P. Barrett, L. G. Joyner, P. P. Halenda, J. Am. Chem. Soc. 1951, 73, 373-380.

Related to the $SiO_2/Al_2O_3$ mole ratio of a zeolite catalyst is the concentration of the active aluminum sites (without next-nearest-neighboring aluminum atoms, i.e., Al—O—Si—O—Al sequence). In various isomerization processes of the present invention, the number of active aluminum sites can be greater than about 500 μmol/g, greater than about 550 μmol/g, or greater than about 580 μmol/g. The number of active aluminum sites can be in the range from about 500 µmol/g to about 650 µmol/g, from about 550 µmol/g to about 650 µmol/g, from about 580 µmol/g to about 650 µmol/g, or from about 580 µmol/g to about 600 µmol/g.

In general, the isomerization process can be conducted known industrial reactor formats such as fixed-beds.

In some isomerization process, the mass of catalyst divided by the mass flow rate of 2,4-dichlorophenol in the feed to the isomerization zone (weight over feed) is at least about 1000 g·s/g, at least about 5000 g·s/g, at least about 10000 g·s/g, at least about 20000 g·s/g, at least about 50000 g·s/g, or at least about 70000 g·s/g. For example, the mass of catalyst divided by the mass flow rate of 2,4-dichlorophenol in the feed to the isomerization zone can be from about 1000 g·s/g to about 150000 g·s/g, from about 5000 g·s/g to about 150000 g·s/g, from about 20000 g·s/g to about 150000 g·s/g, from about 20000 g·s/g to about 120000 g·s/g, from about 20000 g·s/g to about 100000 g·s/g, or from about 20000 g·s/g to about 70000 g·s/g.

The isomerization processes of the present invention can be conducted over a broad temperature range. Generally, the catalyst is contacted with a feed comprising 2,4-dichlorophenol at a catalyst temperature in the range of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

In various processes of the present invention, the temperature of the catalyst is no greater than about 450° C. because it has been found in certain instances that reactants may degrade and undesired products may be generated at temperatures above 450° C. Applicants have found that when the catalyst temperature is controlled in a certain range, the selectivity for 2,5-dichlorophenol is improved. Without being bound by theory, it is believed that decomposition reactions are restricted relative to isomerization reactions occurring in this temperature range. It has been found that the isomerization becomes relatively faster than thermal decomposition in this controlled temperature because the isomerization may have a lower activation energy than the decomposition reactions. In addition, it is believed that 3,4-dichloriphenol derived from a 2→3 chlorine shift is less favored relative to 2,5-dichlorophenol from a desired 4→5 chlorine shift in isomerization reactions in this temperature range. Therefore, improved 2,5-dichlorophenol selectivity may be achieved when the catalyst temperature is maintained in these temperature ranges. At catalyst temperatures outside these limits, it is possible that other isomers such as 3,4-dichlorophenol and 2,6-dichlorophenol may be favored and other decomposition reactions and catalyst deactivation may be promoted. In particular, increased selectivity may be achieved in some processes when the temperature of the catalyst is in the range of from about 250° C. to about 375° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 285° C., from about 280° C. to about 325° C., or from about 290° C. to about 310° C. Also, it has been found that in various processes, the temperature of the catalyst can be less than 300° C. (e.g., less than about 290° C. or less than about 285° C.).

The feed comprising 2,4-dichlorophenol can be introduced to the isomerization zone as a gas or a liquid. When gaseous 2,4-dichlorophenol is introduced into the isomerization reaction zone containing the zeolite catalyst, the partial pressure of 2,4-dichlorophenol in the feed gas can be at least about 0.05 kPa, at least about 0.5 kPa, at least about 1 kPa. The partial pressure of 2,4-dichlorophenol in the feed gas to the isomerization reaction zone can be from about 0.05 kPa to about 10 kPa, from about 0.5 kPa to about 10 kPa, or from about 1 kPa to about 10 kPa. In some cases, the selectivity of 2,5-dichlorophenol can be increased by increasing the 2,4-dichlorophenol partial pressure because it is believed that formation of 3,4-dichlorophenol by-product may be reduced relative to the formation of 2,5-dichlorophenol. It is believed that the chlorine at the 2-position, next to the OH group of 2,4-dichlorophenol (as well as 2,5-dichlorophenol) may be more "protected" at higher partial pressures (i.e., dechlorination of 2,4-dichlorophenol and 2,5-dichlorophenol may be less favored at higher partial pressures relative to dechlorination at other positions).

The isomerization reaction can be conducted in an inert atmosphere such as nitrogen or argon gas. In some cases, it has been found that reducing the oxygen and water concentration beneficially suppresses the formation of monochlorophenols. It is believed that water interacts with the chlorine group of phenols and accelerates the dechlorination pathway. Accordingly, the isomerization reaction can be conducted in atmosphere that is essentially free of oxygen and water.

Notwithstanding the above, it has been surprisingly found that in some instances the presence of water in the isomerization zone beneficially enhances the activity of the zeolite catalyst. Accordingly, various isomerization processes for producing 2,5-dichlorophenol comprise contacting a feed comprising 2,4-dichlorophenol and water with a zeolite catalyst in acid form in an isomerization zone to isomerize at least a portion of the 2,4-dichlorophenol to 2,5-dichlorophenol. Without bound to theory, it is believed that the water most likely reacts with or reduces the binding energies of the large aromatic species that are irreversibly bound to the active sites of catalyst under the reaction conditions, allowing the bound molecules to dissociate from the zeolite.

The water may be fed to isomerization zone with the feed containing 2,4-dichlorophenol, via a separate stream, or both. Also, the water may be fed continuously or intermittently to the isomerization zone. It has been found in various instances that feeding water continuously at a relatively low flow rate or intermittently maintains an improved level of selectivity while enhancing the yield of 2,5-dichlorophenol.

In general, the amount of water fed to the isomerization zone is relatively small when compared to the weight of the catalyst. Accordingly, the weight ratio of catalyst to water per hour is typically at least about 150:1, at least about 200:1, at least about 300:1, or at least about 400:1. The weight ratio of catalyst to water can be in the range from about 150:1 to about 500:1, from about 150:1 to about 400:1, from about 200:1 to about 500:1, or from about 200:1 to about 400:1. Also, the weight ratio of 2,4-dichlorophenol in the feed to water per hour is typically at least about 5:1, at least about 10:1, at least about 15:1, or at least about 20:1. The weight ratio of 2,4-dichlorophenol in the feed to water can be in the range from about 5:1 to about 30:1, from about 5:1 to about 25:1, from about 5:1 to about 20:1, or from about 10:1 to about 20:1.

The water can be fed to the isomerization zone at the temperature of the zeolite catalyst. For example, when the feed is a gas, the water can be fed to the isomerization zone as steam at a temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

It has further been found that the selectivity of 2,5-dichlorophenol can be enhanced by co-feeding 3,4-dichlorophenol to the isomerization zone. Thus, another process of the present invention for producing 2,5-dichlorophenol comprises contacting a feed comprising 2,4-dichlorophenol and 3,4-dichlorophenol with a zeolite catalyst in acid form in an isomerization zone to isomerize at least a portion of the 2,4-dichlorophenol to 2,5-dichlorophenol. The 3,4-dichlorophenol may be fed to isomerization zone with the feed containing 2,4-dichlorophenol, via separate stream, or both. Also, the 3,4-dichlorophenol may be fed continuously or intermittently to the isomerization zone. The 3,4-dichlorophenol can be a component of a recycle stream containing 2,4-dichlorphenol, which can be obtained from a downstream separation process of the isomerization reaction product. In that case, the recycle stream containing 2,4-dichlorophenol and 3,4-dichlorophenol can be fed to isomerization zone. The feed to the isomerization zone may also contain a minor portion of 2,5-dichlorphenol (e.g., as a component of a recycle stream containing 2,4-dichlorophenol and 3,4-dichlorophenol mixture). The presence of 2,5-dichlorphenol in the feed is believed to decrease the selectivity due to the increase of the off-target isomerization of 2,5-dichlorophenol to 3,4-dichlorophenol. However, co-feeding 3,4-dichlorphenol to the isomerization zone has been found to beneficially limit this decrease in selectivity.

Typically, the amount of 3,4-dichlorophenol that is fed to the isomerization zone is relatively small compared to the amount of 2,4-dichlorophenol in the feed. Accordingly, the mole ratio of 2,4-dichlorophenol to 3,4-dichlorophenol is typically at least about 10:1, at least about 15:1, at least about 20:1, at least about 30:1, or at least about 40:1. For example, the mole ratio of 2,4-dichlorophenol to 3,4-dichlorophenol can be in the range from about 10:1 to about 50:1, from about 10:1 to about 40:1, from about 10:1 to about 30:1, from about 10:1 to about 20:1, from about 15:1 to about 50:1, from about 15:1 to about 40:1, from about 15:1 to about 30:1, from about 15:1 to about 20:1, from about 20:1 to about 50:1, from about 20:1 to about 40:1, or from about 20:1 to about 30:1.

As explained, the various isomerization processes of the present invention generally provide improved selectivity for 2,5-dichlorophenol. Typically, the selectivity of the isomerization of 2,4-dichlorophenol to 2,5-dichlorophenol is at least about 50%, at least about 60%, at least about 70%, at least about 80%, at least about 85%, at least about 90%, or at least about 95%. The selectivity of the isomerization of 2,4-dichlorophenol to 2,5-dichlorophenol can be from about 50% to about 99%, from about 70% to about 99%, from about 70% to about 97%, from about 70% to about 95%, from about 80% to about 99%, from about 80% to about 97%, from about 80% to about 95%, from about 85% to about 97%, from about 85% to about 95%, or from about 90% to about 97%. Selectivity for 2,5-dichlorophenol in the isomerization reaction is defined according to equation (A):

$$2,5-DCP \text{ selectivity} = \frac{\text{moles of } 2,5-DCP}{\Sigma(\text{moles of all phenols except } 2,4-DCP)} \times 100\% \quad (A)$$

Due to analytical limitations, quantification of all phenols and degradants may not be possible. Therefore, the sum of the moles of all phenols except 2,4-dichlorophenol can be approximated by the sum of the moles of 2,3-dichlorophenol; 2,5-dichlorophenol; 2,6-dichlorophenol; 3,4-dichlorophenol; 2-chlorophenol; 3-chlorophenol; and 4-chlorophenol.

Further, the isomerization processes of the present invention generally provide conversions of 2,4-dichlorophenol of at least about 10%, at least about 15%, at least about 20%, or at least about 25%. The level of conversion of 2,4-dichlorophenol may change over the life of the zeolite catalyst. For example, it has been observed that high conversions (e.g., greater than 40%) can be obtained when using fresh zeolite catalyst for a limited amount of time-on-stream. As time-on-stream increases, the catalyst may deactivate (e.g., by coking) to a certain extent which reduces conversion. However, it has been observed that the catalyst can be stable for an extended period of time (e.g. 4 to 5 days) without significant deactivation after reaching the steady state. Eventually, the catalyst may need to be regenerated when an acceptable conversion cannot be maintained. Thus, conversion of 2,4-dichlorophenol can be dependent upon the length of time-on-stream for a given catalyst charge. Accordingly, at some point in the time-on-stream for the catalyst, the conversion of 2,4-dichlorophenol can be in the range of from about 10% to about 65%, from about 10% to about 60%, from about 10% to about 50%, from about 10% to about 45%, from about 15% to about 65%, from about 15% to about 60%, from about 15% to about 50%, from about 20% to about 65%, from about 20% to about 60%, from about 20% to about 50%, or from about 20% to about 40%. Conversion of 2,4-dichlorophenol is defined according to equation (B):

$$\frac{\text{moles of } 2,4-DCP \text{ reacted}}{\Sigma(\text{moles of all phenols in reaction product})} \times 100\% \quad (B)$$

The sum of the moles of all phenols in the reaction product can be approximated by the sum of the moles of 2,3-dichlorophenol; 2,4-dichlorophenol; 2,5-dichlorophenol; 2,6-dichlorophenol; 3,4-dichlorophenol; 2-chlorophenol; 3-chlorophenol; and 4-chlorophenol.

The isomerization reaction may generate various off-target phenols such as 3,4-dichlorophenol; 2,6-dichlorophenol; 2-chlorophenol; 3-chlorophenol; and 4-chlorophenol. Accordingly, the isomerization reaction product can include one or more off-target phenols selected from the group consisting 3,4-dichlorophenol, 2,6-dichlorophenol, 4-chlorophenol, 3-chlorophenol, 2-chlorophenol, and mixtures thereof. 3,4-Dichlorophenol has been found to be one of the primary off-target phenols that is produced. The molar yield of 3,4-dichlorophenol in the isomerization reaction product can be typically less than about 5%, less than about 3%, less than about 1%, or between about 1% and about 5%.

Monochlorophenols are also another primary off-target product. The sum of molar yields of 2-chlorophenol, 3-chlorophenol, and 4-chlorophenol can be less than about less than about 5%, less than about 3%, less than about 1%, or between about 1% and about 5%.

The isomerization processes of the present invention can also include a catalyst regeneration step in which after a period of use on-stream, the zeolite catalyst is calcined in air at elevated temperatures (e.g., at least about 500° C., or from about 500° C. to about 600° C.). In some cases, it has been found that regenerating the zeolite catalyst with steam at high temperatures, for example at about 700° C. or higher, negatively impacts both conversion of 2,4-dichlorophenol and selectivity for 2,5-dichlorophenol of the regenerated catalyst. Without being bound by theory, it is thought that these negative impacts are caused by the loss of the active acid sites through a dealumination process. Dealumination is believed to increase the concentration of defect (inactive) sites and can result in the increase of the $SiO_2/Al_2O_3$ ratio.

Applicants have also discovered that the zeolite catalyst used in isomerization processes of the present invention can alternatively be regenerated using a relatively low temperature rejuvenation process. Thus, another process of the present invention for producing 2,5-dichlorophenol comprises contacting a feed comprising 2,4-dichlorophenol with a zeolite catalyst in acid form in an isomerization zone to isomerize at least a portion of the 2,4-dichlorophenol to 2,5-dichlorophenol; suspending contact of the feed comprising 2,4-dichlorophenol with the zeolite catalyst; and contacting the zeolite catalyst with steam at a temperature from about 250° C. to about 375° C. to rejuvenate the catalyst. The temperature of the steam can be in the range of from about 250° C. to about 375° C., from about 270° C. to about 350° C., from about 280° C. to about 325° C., or from about 290° C. to about 310° C. (e.g., about 300° C.). Also, the temperature of the steam can be the same or approximately the same (+/−5% or 10%) temperature as the catalyst temperature during the isomerization reaction.

Suspending contact with the feed can be performed in several ways. For example, the feed to the isomerization zone can be stopped and then the steam can be fed to the isomerization zone to contact the zeolite catalyst with the steam. Alternatively, to suspend contact with the feed, the zeolite catalyst can be removed from the isomerization zone and then contacted with steam. Following rejuvenation, the zeolite catalyst can be purged with an inert gas such as nitrogen. Also, after rejuvenation, the zeolite catalyst can be redeployed in the isomerization zone (i.e., restarting contact of the feed stream comprising 2,4-dichlorophenol).

Any features or aspects described herein with respect to the isomerization processes of the present invention can be used either singularly or in combination. For example, one isomerization process for producing 2,5-dichlorophenol in accordance with the present invention comprises contacting a feed (gas or liquid) comprising 2,4-dichlorophenol with a zeolite catalyst in acid form (e.g., a HZSM-5 zeolite) in an isomerization zone to isomerize at least a portion of the 2,4-dichlorophenol to 2,5-dichlorophenol, wherein the zeolite catalyst has a $SiO_2/Al_2O_3$ mole ratio of no greater than about 35:1 (or from about 20:1 to about 35:1) and the isomerization is conducted at a temperature of from about 250° C. to about 550° C., from about 275° C. to about 550°

C., from about 200° C. to about 450° C., from about 250° C. to about 375° C., from about 270° C. to about 350° C., from about 280° C. to about 325° C., or from about 290° C. to about 310° C.

Furthermore, for example, isomerization process for producing 2,5-dichlorophenol in accordance with the present invention comprises contacting a feed (gas or liquid) comprising 2,4-dichlorophenol with a zeolite catalyst in acid form (e.g., a HZSM-5 zeolite) in an isomerization zone to isomerize at least a portion of the 2,4-dichlorophenol to 2,5-dichlorophenol wherein the process includes one or more of the following features:

the zeolite catalyst has a $SiO_2/Al2O_3$ mole ratio of no greater than about 35:1.

the zeolite catalyst comprises a desilicated zeolite catalyst having a meso-macro pore volume (>20 Å to 2500 Å) that is at least about 50%, at least about 75%, at least about 100%, at least about 125%, at least about 150%, at least about 175%, at least about 200%, at least about 225%, at least about 250%, at least about 275%, or at least about 300% greater than the meso-macro pore volume of the initial zeolite catalyst before desilication;

the zeolite catalyst (or desilicated zeolite catalyst) has a meso-macro pore volume that is at least about 0.15 $cm^3/g$, at least about 0.175 $cm^3/g$, at least about 0.2 $cm^3/g$, at least about 0.225 $cm^3/g$, or at least about 0.25 $cm^3/g$;

the feed comprising 2,4-dichlorophenol further comprises water (e.g., steam);

the feed comprising 2,4-dichlorophenol further comprises 3,4-dichlorophenol; and/or the process further comprises suspending contact of the feed comprising 2,4-dichlorophenol with the zeolite catalyst and contacting the zeolite catalyst with steam at a temperature from about 250° C. to about 375° C. to rejuvenate the catalyst.

Preparation of 2,5-dichlorophenol

Additional processes in accordance with the present invention are directed to preparing 2,5-dichlorophenol from 1,4-dichlorobenzene. In general, these processes include hydroxylating 1,4-dichlorobenzene with an oxidizing agent in the presence of a zeolite catalyst in a hydroxylation zone to form a reaction product comprising 2,5-dichlorophenol. The reaction proceeds according to the scheme shown below.

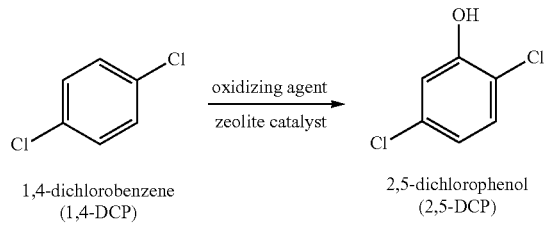 [SMILES: Clc1ccc(Cl)cc1 ; Oc1cc(Cl)ccc1Cl]

1,4-dichlorobenzene (1,4-DCP)

2,5-dichlorophenol (2,5-DCP)

Generally, the zeolite catalyst can be a metal-promoted zeolite or zeolite in acid form. Metal-promoted zeolites include, for example, titanium silicates such as TS-1 and TS-PQ, vanadium-containing zeolites such as V-Beta, and metal-promoted alumino-silicates such as Fe-ZSM-5 and Fe-ZSM-11. Suitable zeolites, which can be metal-promoted or in acid form, include pentasil and faujasite zeolites such as zeolite Beta, ZSM type zeolites, zeolite Y, and mixtures thereof. Acid form ZSM type zeolites include, for example, HZSM-5 and HZSM-11. In various hydroxylation processes of the present invention, the zeolite includes a metal-promoted alumino-silicate, particularly Fe-ZSM-5.

It has been found that in some processes when iron-promoted zeolites, particularly Fe-ZSM-5, are used, then the catalyst activity and selectivity for 2,5-dichlorophenol is significantly increased. The iron loading of the catalyst is thought to be one important factor in achieving increased activity and selectivity. The iron loading is typically less than about 2 wt. %, less than about 1 wt. %, less than about 0.8 wt. %, less than about 0.5 wt. %, or less than about 0.1 wt. % of the total catalyst weight. The iron loading can be in the range of from about 0.01 wt. % to about 2 wt. %, from about 0.05 wt. % to about 2 wt. %, from about 0.01 wt. % to about 1 wt. %, from about 0.05 wt. % to about 1 wt. %, from about 0.05 wt. % to about 0.5 wt. %, or from about 0.01 wt. % to about 0.2 wt. % of the total catalyst weight.

One aspect of the zeolite catalyst is the mole ratio of $SiO_2/Al_2O_3$. In various hydroxylation processes, the $SiO_2/Al_2O_3$ mole ratio can be at least about 20:1, at least about 23:1, at least about 30:1, or at least about 50:1. The $SiO_2/Al_2O_3$ mole ratio can be in the range of from about 20:1 to about 1000:1, from about 20:1 to about 500:1, from about 23:1 to about 500:1, from about 23:1 to about 350:1, from about 30:1 to about 350:1, from about 30:1 to about 280:1, from about 50:1 to about 350:1, or from about 80:1 to about 280:1.

It has also been found that the activation temperature and method can impact the performance of the zeolite catalyst. In some instances, it has been observed that higher calcination temperatures of the fresh zeolite catalyst prior to use or after regeneration beneficially reduces the isomerization and decomposition of the 2,5-dichlorophenol product to off-target reaction products such as 2,4-dichlorophenol and monochlorophenols. In some instances, it has been observed that the catalyst activated either at a higher temperature or at slightly lower temperature by steam may beneficially increase the stability of the catalyst during the hydroxylation reaction. Without being bound by theory, it is believed that the steam activation of the catalyst may create meso-porosity in the zeolite structure, which prevents the catalyst from deactivating by coking. Accordingly, in processes of the present invention, the zeolite can be first calcined, then activated and calcined again prior to use.

For example, in one catalyst preparation method, the zeolite (e.g. $NH_4$-ZSM-5) can be first calcined in air to convert to the zeolite to the acid form of the catalyst (i.e. H-ZSM-5). The first calcination can be conducted at a temperature that is at least about 500° C., at least about 600° C., at least about 700° C., at least about 800° C., or at least about 900° C. A metal-promoted zeolite (e.g. Fe-ZSM-5) can be prepared from an ion-exchange of the catalyst in acid form (i.e. H-ZSM-5) and can be calcined at a temperature that is at least about 500° C., at least about 600° C., at least about 700° C., at least about 800° C., or at least about 900° C. The calcination temperature can be in the range of from about 500° C. to about 1000° C., from about 600° C. to about 1000° C., from about 700° C. to about 1000° C., from about 800° C. to about 1000° C., or from about 900° C. to about 1000° C., from about 500° C. to about 900° C., from about 500° C. to about 800° C., from about 500° C. to about 700° C., from about 520° C. to about 600° C., from about 530° C. to 580° C., or from about 540° C. to 560° C. The zeolite (e.g. Fe-ZSM-5) can then be activated using steam or argon gas at a temperature that is at least about 600° C., at least about 700° C., at least about 800° C., or at least about 900° C. The activation of the catalyst under an argon gas can be at a temperature in the range of from about 800° C. to about 1000° C., or from about 850° C. to about 950° C. The activation of the catalyst with steam under an argon gas can be at a temperature in the range of from about 600° C. to about 800° C., or from about 650° C. to about 700° C. Following activation, the catalyst is finally calcined under a nitrogen gas prior to use at a temperature that is at least about 600° C., at least about 700° C., at least about 800° C., or at least about 900° C. The calcination temperature can be in the range of from about 600° C. to about 1000° C., from about 600° C. to about 900° C., from about 700° C. to about 800° C., or from about 740° C. to about 760° C.

The hydroxylation processes of the present invention can be conducted over a wide temperature range. Generally, gas comprising the 1,4-dichlorobenzene is contacted with the catalyst at a temperature in the range of from about 250° C. to about 550° C., from about 275° C. to about 500° C., from about 275° C. to about 400° C., from about 275° C. to about 375° C., from about 300° C. to about 500° C., from about 300° C. to about 450° C., or from about 350° C. to about 400° C. In some instances, applicants have discovered that when the catalyst temperature is controlled in a certain range, the conversion of 1,4-dichlorobenzene can be improved and competitive isomerization of 1,4-dichlorobenzene (e.g., to 1,3-dichlorobenzene) can be beneficially suppressed while still maintaining a high selectivity for the conversion to 2,5-dichlorophenol. In particular, these advantages may be achieved in some processes when the temperature of the catalyst is in the range of from about 350° C. to about 450° C., from about 375° C. to about 425° C., or from about 385° C. to about 415° C.

Various oxidizing agents may be used in the hydroxylation processes of the present invention. Suitable oxidizing agents include hydrogen peroxide, molecular oxygen, mixture of oxygen/hydrogen, mixture of oxygen/ammonia, and nitrous oxide. In various processes, it has been found that the use of nitrous oxide as an oxidizing agent is particularly beneficial.

A molar excess of oxidizing agent (e.g., nitrous oxide) to 1,4-dichlorobenzene can be used in the hydroxylation reaction. In some instances, a limited molar amount of oxidizing agent to 1,4-dichlorobenzed can be used to improve the selectivity of 2,5-dichlorophenol formation and suppress other off-target reaction products such as 2,4-dichlorophenol and monochlorophenols. The mole ratio of oxidizing agent to 1,4-dichlorobenzene can be at least about 0.25:1, at least about 0.5:1, at least about 1:1, at least about 2:1, at least about 3:1, at least about 4:1, or at least about 5:1. The mole ratio of oxidizing agent to 1,4-dichlorobenzene can be in the range of from about 0.25:1 to about 10:1, from 0.5:1 to about 8:1, from 1:1 to about 5:1, from about 2:1 to about 10:1, from about 2:1 to about 5:1, from about 3:1 to about 10:1, or from about 3:1 to about 5:1.

As described, the hydroxylation processes of the present invention generally provide improved selectivity for 2,5-dichlorophenol. Typically, the selectivity of the hydroxylation of 1,4-dichlorobenzene to 2,5-dichlorophenol is at least about 50%, at least about 60%, at least about 70%, at least about 80%, at least about 85%, at least about 90%, or at least about 95%. The selectivity of the hydroxylation of 1,4-dichlorobenzene to 2,5-dichlorophenol can be from about 50% to about 99%, from about 50% to about 90%, from about 60% to about 99%, from about 60% to about 95%, from about 60% to about 90%, from about 70% to about 99%, from about 70% to about 95%, from about 70% to about 90%, or from about 75% to about 95%.

Selectivity for 2,5-dichlorophenol in the hydroxylation reaction is defined according to equation (C):

$$2,5-DCP \text{ selectivity} = \frac{\text{moles of } 2,5-DCP}{\Sigma(\text{moles of all benzenes and phenols except } 1,4-DCB)} \times 100\% \quad (C)$$

The sum of the moles of all benzenes and phenols in the reaction product except 1,4-dichlorobenzene can be approximated by the sum of the moles of 1,2-dichlorobenzene; 1,3-dichlorobenzene; 2,4-dichlorophenol; 2,5-dichlorophenol; 2-chlorophenol; 3-chlorophenol; and 4-chlorophenol.

The level of selectivity for 2,5-dichlorobenzene may change over the life of the zeolite catalyst. For example, in some cases, improved selectivity has been observed when the zeolite catalyst has been aged (i.e., used on stream) for limited amount time-on-stream. The reason for this is unknown, but one theory is that the active sites causing lower selectivity might deactivate first.

Further, the hydroxylation processes of the present invention generally provide conversions of 1,4-dichlorobenzene of at least about 5%, at least about 10%, at least about 15%, or at least about 20%. Accordingly, at some point in the time-on-stream for the catalyst, the conversion of 1,4-dichlorobenzene can range from about 5% to about 50%, from about 5% to about 40%, from about 5% to about 30%, from about 10% to about 50%, from about 10% to about 40%, from about 10% to about 30%, from about 15% to about 50%, from about 15% to about 40%, from about 15% to about 30%, from about 20% to about 50%, from about 20% to about 40%, or from about 20% to about 30%. Conversion of 1,4-dichlorobenzene is defined according to equation (D):

$$\frac{\text{moles of } 1,4-DCB \text{ reacted}}{\Sigma(\text{moles of all benzenes and phenols in reaction product})} \times 100\% \quad (D)$$

The sum of the moles of all benzenes and phenols in the reaction product can be approximated by the sum of the moles of 1,2-dichlorobenzene; 1,3-dichlorobenzene; 1,4-dichlorobenzene; 2,4-dichlorophenol; 2,5-dichlorophenol; 2-chlorophenol; 3-chlorophenol; and 4-chlorophenol.

The hydroxlyation reaction may generate various off-target phenols such as 1,2-dichlorobenzene; 1,3-dichlorobenzene; 2,4-dichlorophenol; 2-chlorophenol; 3-chlorophenol; and 4-chlorophenol. Accordingly, the hydroxlyation reaction product can include one or more off-target phenols selected from the group consisting 1,2-dichlorobenzene; 1,3-dichlorobenzene; 2,4-dichlorophenol; 2-chlorophenol; 3-chlorophenol; and 4-chlorophenol and mixtures thereof. Under various conditions, 2,4-dichlorophenol has been found to be one of the primary off-target phenols that is produced. The molar yield of 2,4-dichlorophenol in the hydroxylation reaction product is typically less than about 40%, less than about 35%, less than about 30%, less than about 25%, less than about 20%, less than about 15%, less than about 10%, less than about 5%, or less than about 1%. The molar yield of 2,4-dichlorophenol in the hydroxylation reaction product can range from about 0.01% to about 40%, from about 0.01% to about 35%, from about 0.01% to about 25%, from about 0.1% to about 20%, from about 0.5% to about 40%, from about 0.5% to about 35%, from about 0.01% to about 15%, from about 0.01% to about 10%, from about 0.01% to about 5%, from about 0.1% to about 1%, from about 0.5% to about 10%, or from about 0.5% to about 5%.

Monochlorophenols are also another primary off-target product that can be produce in the hydroxylation reaction. In some instances, the sum of molar yields of 2-chlorophenol, 3-chlorophenol, and 4-chlorophenol is less than about 10%, less than about 5%, or less than about 1%. The sum of molar yields of 2-chlorophenol, 3-chlorophenol, and 4-chlorophenol in the hydroxylation reaction product can also be in the range of from about 0.1% and about 10% or from about 1% to about 5%.

The hydroxylation reaction can be conducted in an inert atmosphere such as nitrogen or argon gas. In some cases, it has been found that reducing the oxygen concentration beneficially suppresses the formation of monochlorophenols. Accordingly, the hydroxylation reaction can be conducted in atmosphere that is essentially free of oxygen.

As time-on-stream increases, the catalyst may deactivate to a certain extent which may reduce catalyst activity. Eventually, the catalyst may need to be regenerated when an acceptable conversion cannot be maintained. Thus, the hydroxylation processes of the present invention can also include a catalyst regeneration step in which after a period of use the zeolite catalyst is calcined at elevated temperatures (e.g., at least about 400° C. or at least about 500° C.) to regenerate the catalyst.

Hydroxylation processes of the present invention can further comprise separating at least a portion of the 2,5-dichlorophenol from other reaction product constituents. Processes for separating 2,5-dichlorophenol from mixtures include those described in U.S. Pat. Nos. 2,708,209 and 3,462,498, which are incorporated herein by reference. Additionally or alternatively, the hydroxylation processes of the present invention can further comprise the step of separating at least a portion of the 2,4-dichlorophenol from other reaction product constituents. One process for separating 2,4-dichlorophenol from a mixture is described in U.S. Pat. No. 5,118,876, which is incorporated herein by reference.

Separation of 2,5-dichlorophenol from the hydroxylation reaction product or conversely, separation 2,4-dichlorophenol from the hydroxylation reaction product produces a fraction that is enriched in 2,4-dichlorophenol. This fraction can be introduced to an isomerization process to further convert the 2,4-dichlorophenol to 2,5-dichlorophenol. Thus, the hydroxylation processes of the present invention can further comprise isomerizing at least a portion of the 2,4-dichlorophenol obtained in the hydroxylation process. In various processes of the present invention, isomerizing the 2,4-dichlorophenol obtained in the hydroxylation process is conducted according to the isomerization processes of the present invention described herein.

Accordingly, another process of the present invention for producing 2,5-dichlorophenol comprises hydroxylating 1,4-dichlorobenzene with an oxidizing agent in the presence of a first zeolite catalyst in a hydroxylation zone to form a hydroxylation reaction product comprising 2,5-dichlorophenol and 2,4-dichlorophenol; separating at least a portion of the 2,4-dichlorophenol from the hydroxylation reaction product to form a fraction comprising 2,4-dichlorophenol; and contacting the fraction comprising 2,4-dichlorophenol with a second zeolite catalyst in acid form to isomerize at least a portion of the 2,4-dichlorophenol to 2,5-dichlorophenol.

Production of 3,6-dichloro-2-methoxybenzoic acid 2,5-Dichlorophenol produced in accordance with any of the processes described herein can be further converted to 3,6-dichloro-2-methoxybenzoic acid (dicamba) and salts or esters thereof. U.S. Pat. No. 3,013,054, which is incorporated herein by reference, describes one process for the production of 3,6-dichloro-2-methoxybenzoic acid. In general, this process involves carboxylating the 2,5-dichlorophenol to produce 2-hydroxy-3,6-dichlorobenzoic acid followed by methylating the 2-hydroxy-3,6-dichlorobenzoic acid to 3,6-dichloro-2-methoxybenzoic acid. Thus, the hydroxylation and isomerization processes of the present invention can be further combined with various processes for producing 3,6-dichloro-2-methoxybenzoic acid.

Any features described herein with respect to the processes of the present invention can be used either singularly or in combination.

Having described the invention in detail, it will be apparent that modifications and variations are possible without departing from the scope of the invention defined in the appended claims.

EXAMPLES

The following non-limiting examples are provided to further illustrate the present invention.

Example 1: High-Performance Liquid Chromatography ("HPLC") Analytical Methods

A. HPLC Method for Determination of Chlorinated Phenols

HPLC analysis used to monitor the compositions of isomerization reaction was conducted on an Agilent 1260 Infinity Analytical HPLC System equipped with a diode array UV detector and monitored at 220 nm. The column was a X-Bridge C18, 4.6×150 mm, 3.5 micron with a pre-column filter and the column temperature was at 30° C. The HPLC was conducted at a flow rate of 2 mL/minute of mobile phase A (85% water, 15% acetonitrile) and mobile phase B (100% acetonitrile) as described in Tables 1-A1 and 1-A2 below:

TABLE 1-A1

HPLC Method for Determination of Chlorinated Phenols

| TIME | % MPA | % MPB |
|---|---|---|
| 0.00 | 85 | 15 |
| 17.50 | 85 | 15 |
| 17.51 | 5 | 95 |
| 20.00 | 5 | 95 |
| 20.10 | 85 | 15 |
| 24.00 | 85 | 15 |

TABLE 1-A2

Retention Times of Monochlorophenols and Dichlorophenols by Chlorinated Phenol Method

| Monochlorophenols | Retention Time (minute) | Dichlorophenols | Retention Time (minute) |
|---|---|---|---|
| 2-Chlorophenol | 4.89 | 2,6-Dichlorophenol | 9.54 |
| 4-Chlorophenol | 6.13 | 2,3-Dichlorophenol | 12.12 |
| 3-Chlorophenol | 6.56 | 2,5-Dichlorophenol | 13.45 |
|  |  | 2,4-Dichlorophenol | 14.50 |
|  |  | 3,4-Dichlorophenol | 15.71 |

B. HPLC Method for Determination of Chlorinated Benzenes

HPLC analyses used to monitor the compositions of hydroxylation reaction were conducted with a combination of both chlorinated benzene method and the aforementioned chlorinated phenol method. The chlorinated benzene HPLC method was conducted on an Agilent 1260 Infinity Analytical HPLC System equipped with a diode array UV detector and monitored at 220 nm. The column was an X-Bridge C18, 4.6×150 mm, 3.5 micron with a pre-column filter and the column temperature was at 30° C. The HPLC was conducted at a flow rate of 1.5 mL/minute of mobile phase A (85% water, 15% acetonitrile) and mobile phase B (100% acetonitrile) as described in Tables 1-B1 and 1-B2 below:

TABLE 1-B1

HPLC Method for Determination of Chlorinated Benzenes

| TIME | % MPA | % MPB |
|---|---|---|
| 0.00 | 56 | 44 |
| 8.00 | 56 | 44 |
| 8.10 | 5 | 95 |
| 10.00 | 5 | 95 |
| 10.10 | 56 | 44 |
| 12.00 | 56 | 44 |

TABLE 1-B2

Retention Times of Dichlorobenzenes by Chlorinated Benzene Method

| Dichlorobenzenes | Retention Time (minute) |
|---|---|
| 1,4-Dichlorobenzene | 6.71 |
| 1,3-Dichlorobenzene | 7.24 |

Example 2: Isomerization of 2,4-Dichlorophenol to 2,5-Dichlorophenol with Calcined Zeolites at Various $SiO_2/Al_2O_3$ Mole Ratios Commercial zeolites (e.g., $NH_4$—ZSM-5) at various $SiO_2/Al_2O_3$ mole ratios were acquired from a zeolite vendor. These materials were then calcined in air at 550° C. or 900° C. for 24 hours to remove any organic template and to convert the zeolites to acid (proton) form (i.e., HZSM-5). The HZSM-5 zeolites at various $SiO_2/Al_2O_3$ mole ratios were charged to a fixed bed reactor vessel and held at approximately 300-310° C. 2,4-Dichlorophenol was charged into a vapor generator. By bubbling nitrogen through the molten 2,4-dichlorophenol at a fixed temperature, a constant vapor feed of 2,4-dichlorophenol to a reactor vessel was achieved. The partial pressure of 2,4-dichlorophenol was approximately 0.3 kPa and the total gas flow rate was 345 $cm^3$/min. The concentrations of 2,4-dichlorophenol and reaction products were measured by the chlorinated phenol HPLC method. Tables 2-A and 2-B and FIGS. 1-5 present the results from this experiment.

TABLE 2-A

Representative 2,5-DCP Selectivity and 2,4-DCP Conversion by the Chlorinated Phenol HPLC Method Exp. No. 2.1
$SiO_2/Al_2O_3$ mole ratio = 23; temperature = 300° C.;
partial pressure = 0.3 kPa; total gas flow rate = 345 cm³/min; time-on-stream = 71 hours; weight over feed = 72000
(gram of catalyst × second)/(gram of 2,4-DCP in the feed)

| Components | Area % by HPLC (%) | Selectivity (%) | Corrected Selectivity* (%) | 2,4-DCP Steady-state Conversion (%) |
|---|---|---|---|---|
| 2-CP | 0.15 | 1.61 | — | — |
| 4-CP | 0.11 | 1.01 | — | — |
| 3-CP | 0.17 | 1.71 | — | — |
| 2,6-DCP | 0.13 | 0.94 | — | — |
| 2,3-DCP | 0.10 | 0.74 | — | — |
| 2,5-DCP | 11.08 | 91.38 | 91.5 | — |
| 2,4-DCP | 87.97 | — | — | 12.0 |
| 3,4-DCP | 0.29 | 2.62 | — | — |

*2,5-DCP selectivity is corrected with impurities existed in the original 2,4-DCP starting material in the feed.

TABLE 2-B

Selectivity and Conversion vs. $SiO_2/Al_2O_3$ Ratio

| Exp. No. | $SiO_2/Al_2O_3$ mole ratio | Total Aluminum Sites (µmol/g) | Aluminum Active Sites (µmol/g) | Catalyst Temperature (° C.) | Gas Flow Rate (cm³/min) | 2,5-DCP Selectivity (%) | 2,4-DCP Steady-state Conversion (%) |
|---|---|---|---|---|---|---|---|
| 2.2 | 23 | ~1270 | ~560 | 300 | 345 | 92 | 22 |
| 2.3 | 30 | ~990 | ~600 | 300 | 345 | 91 | 32 |
| 2.4 | 50 | ~600 | ~400 | 300 | 345 | 87 | 22 |
| 2.5 | 80 | ~400 | ~260 | 300 | 245 | 76 | 18 |
| 2.6 | 280 | ~140 | ~110 | 310 | 345 | 68 | 2 |

The results show that the selectivity of the catalyst for 2,5-dichlorophenol by isomerization generally increased with the decrease in the $SiO_2/Al_2O_3$ mole ratio or as the aluminum content of the zeolite increased. These results suggest that acid sites are the active sites for the isomerization reaction. The conversion of 2,4-dichlorophenol increased systematically with increase in the aluminum concentration up to a $SiO_2/Al_2O_3$ mole ratio of 30, but the activity decreased when this ratio was further lowered to 23. When the 2,4-dichlorophenol conversion is compared against the concentration of aluminum without next-nearest-neighboring aluminum atoms, i.e., Al—O—Si—O—Al sequence, a linear correlation was observed for all samples. This suggests that the activity of the catalyst may depend on the number of acid sites that are relatively "isolated" (or do not have neighboring aluminum species); possibly because the adjacent active sites increase the activation energy for isomerization (from distorted bond angles, changing the ability to stabilize transition state) or these sites enhances adsorption of two reactant molecules and create additional steric hindrances for isomerization. Thus, it is suggested that the catalytic activity decreased from the sample with $SiO_2/Al_2O_3$ mole ratio of 30 to 23, because the number of the "active-isolated sites" decreased from approximately 600 µmol/g to 560 µmol/g, respectively (total concentration of aluminum was approximately 990 and 1270 µmol/g).

Example 3: Effect of Time-on-stream on Selectivity and Conversion of Isomerization Example 2 was repeated except a HZSM-5 catalyst having $SiO_2/Al_2O_3$ mole ratios of 30 and 50 were used. The catalyst temperature was maintained at 300° C. Extended time-on-stream was evaluated for both selectivity and conversion of the reaction. The results of this experiment are provided in Table 3.

TABLE 3

Selectivity and Conversion vs. Time-on-stream

| Exp. No. 3.1 $SiO_2/Al_2O_3$ mole ratio = 50 | | | Exp. No. 3.2 $SiO_2/Al_2O_3$ mole ratio = 30 | | |
|---|---|---|---|---|---|
| Time-on-Stream (hours) | 2,5-DCP Selectivity (%) | 2,4-DCP Conversion (%) | Time-on-Stream (hours) | 2,5-DCP Selectivity (%) | 2,4-DCP Conversion (%) |
| 2 | 87 | 41 | 2 | 91 | 52 |
| 4 | 84 | 27 | 4 | 91 | 44 |
| 8 | 84 | 20 | 8 | 90 | 35 |
| 12 | 84 | 17 | 12 | 91 | 29 |
| 24 | 83 | 13 | 23 | 91 | 24 |
| 36 | 83 | 10 | 35 | 91 | 19 |
| 49 | 83 | 9 | 49 | 91 | 16 |
| 71 | 84 | 8 | 71 | 91 | 15 |
| 80 | 84 | 9 | — | — | — |
| — | — | — | 96 | 91 | 14 |

The results show that the catalyst is consistently selective for 2,5-dichlorophenol and that conversion of 2,4-dichlorophenol is maintained over extended periods of time-on-stream. The results also show that the catalyst can be used in these reaction conditions over extended periods of time-on-stream without significant deactivation.

Example 4: Effect of 2,4-DCP Partial Pressure on Selectivity and Conversion of Isomerization Example 2 was repeated except a HZSM-5 catalyst having a $SiO_2/Al_2O_3$ mole ratio of 30 was used and 2,4-dichlorophenol partial pressure was varied from 0.05 kPa to 0.3 kPa and temperature was varied from 300° C. to 320° C. The results of this experiment are provided in Table 4.

TABLE 4

Selectivity and Conversion vs. 2,4-DCP Partial Pressure

| Exp. No. | SiO$_2$/Al$_2$O$_3$ mole ratio | Catalyst Temperature (° C.) | Gas Flow Rate (cm$^3$/min) | 2,4-DCP partial pressure (kPa) | Weight over feed (gram × sec/gram) | 2,5-DCP Selectivity (%) | 2,4-DCP Steady-state Conversion (%) |
|---|---|---|---|---|---|---|---|
| 4.1 | 30 | 300 | 345 | 0.1 | 24000 | 90 | 25 |
| 4.2 | 30 | 300 | 345 | 0.3 | 72000 | 93 | 15 |
| 4.3 | 30 | 320 | 345 | 0.05 | 24000 | 90 | 32 |
| 4.4 | 30 | 320 | 345 | 0.3 | 72000 | 92 | 17 |

Figure 6:
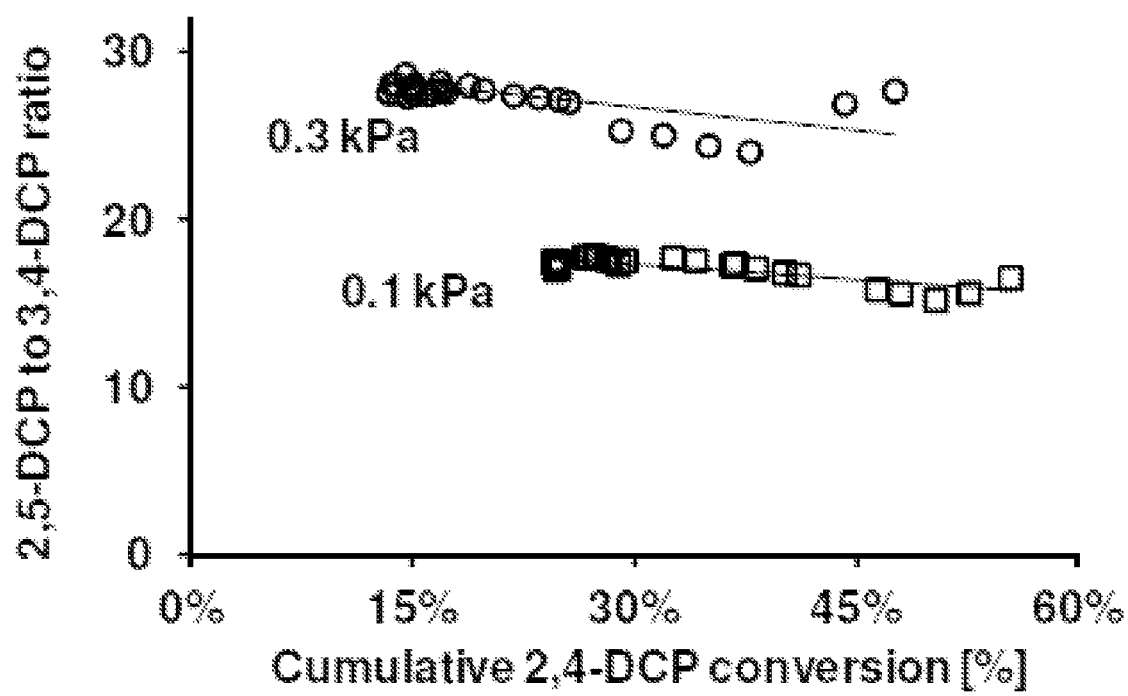
FIGS. 6 and 7 present graphs of the ratio of 2,5-dichlorophenol to 3,4-dichlorophenol as a function of cumulative 2,4-dichlorophenol conversion at various partial pressures of 2,4-dichlorophenol in the feed gas to an isomerization reactor.
Figure 7:
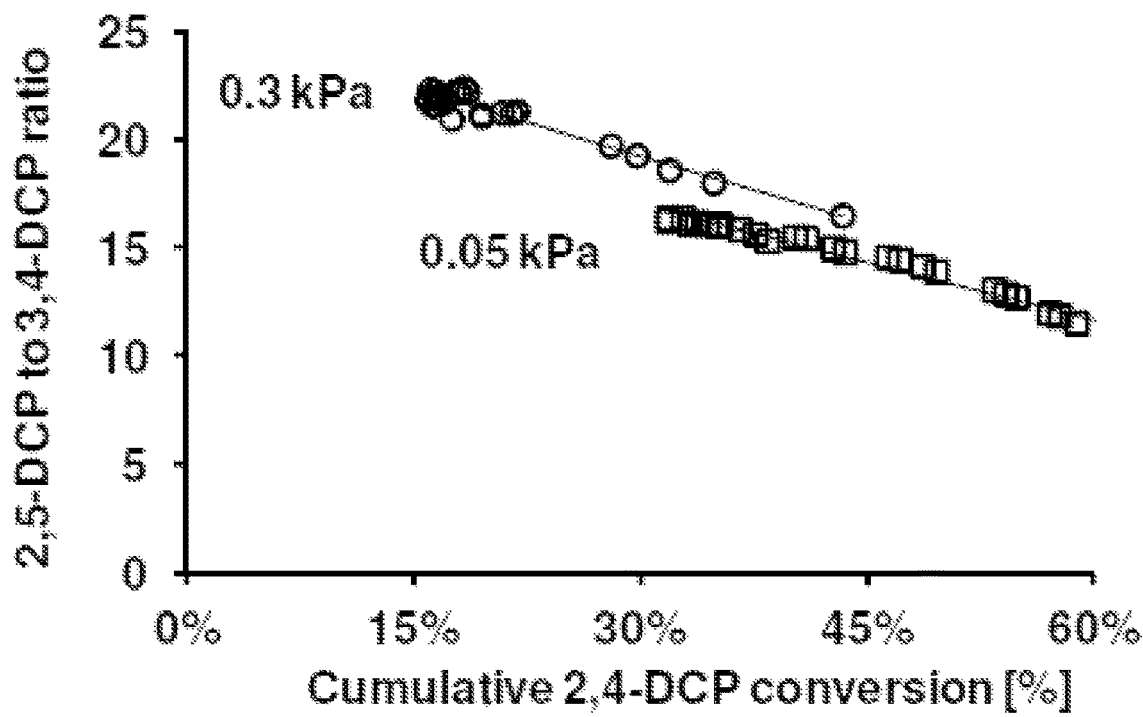
Figure 8:
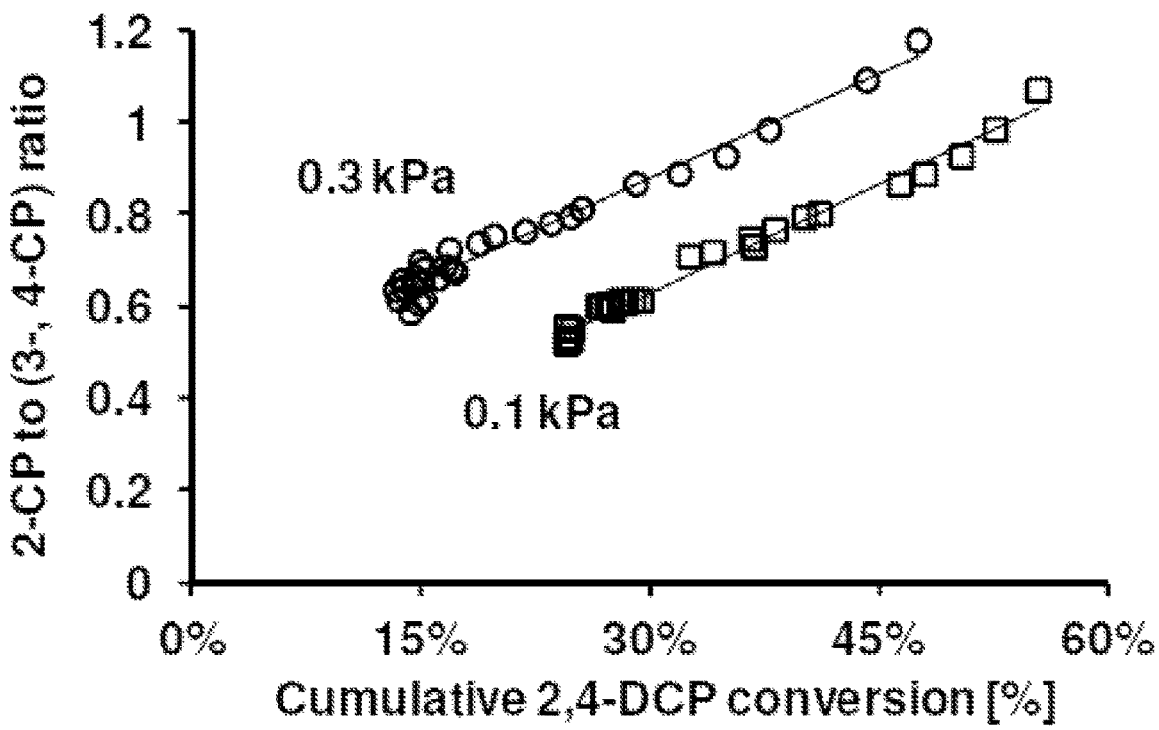
FIGS. 8 and 9 present graphs of the ratio of 2-chlorophenol to 3- and 4-chlorophenol as a function of cumulative 2,4-dichlorophenol conversion at the tested partial pressures of 2,4-dichlorophenol in the feed gas to an isomerization reactor.
Figure 9:
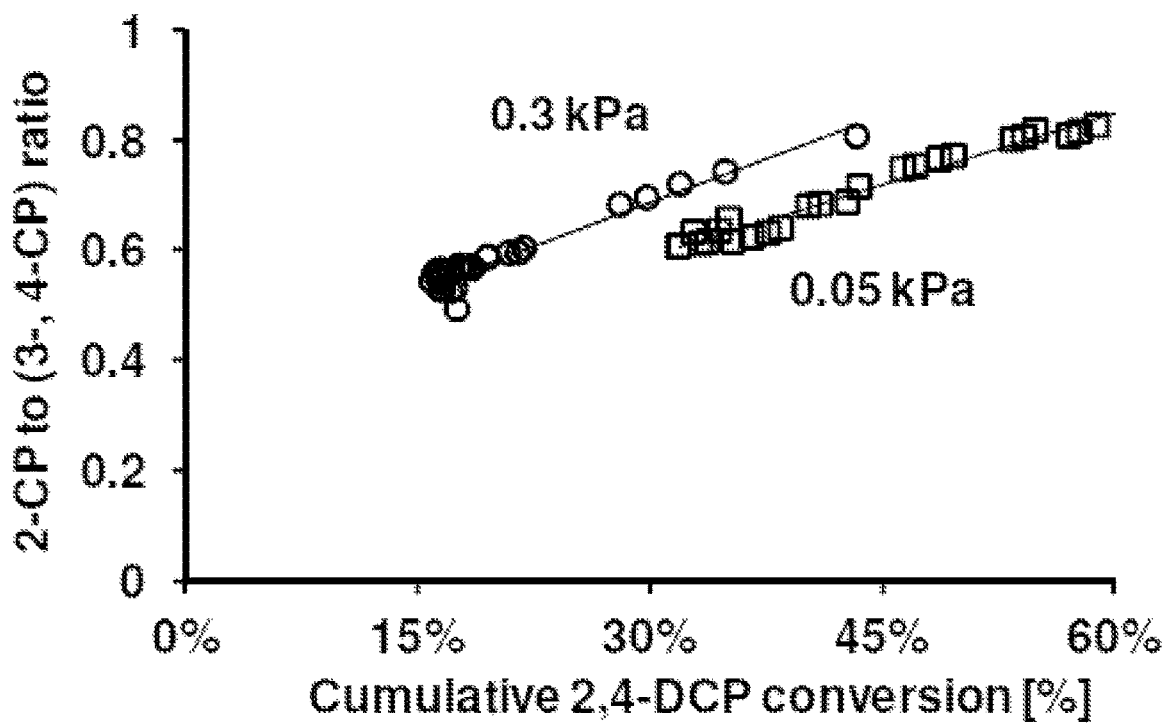

The results show that increasing the partial pressure of 2,4-dichlorophenol increased 2,5-dichlorophenol selectivity. FIGS. 6 and 7 show the ratio of 2,5-dichlorophenol to 3,4-dichlorophenol at the tested partial pressures of 2,4-dichlorophenol. The ratio of 2,5-dichlorophenol to 3,4-dichlorophenol increased by increasing the 2,4-dichlorophenol partial pressure. FIGS. 8 and 9 show the ratio of 2-chlorophenol to 3- and 4-chlorophenol at the tested partial pressures of 2,4-dichlorophenol. The ratio of 2-chlorophenol to (3-chlorophenol+4-chlorophenol) also increased with increasing 2,4-dichlorophenol partial pressure.

Figure 10:
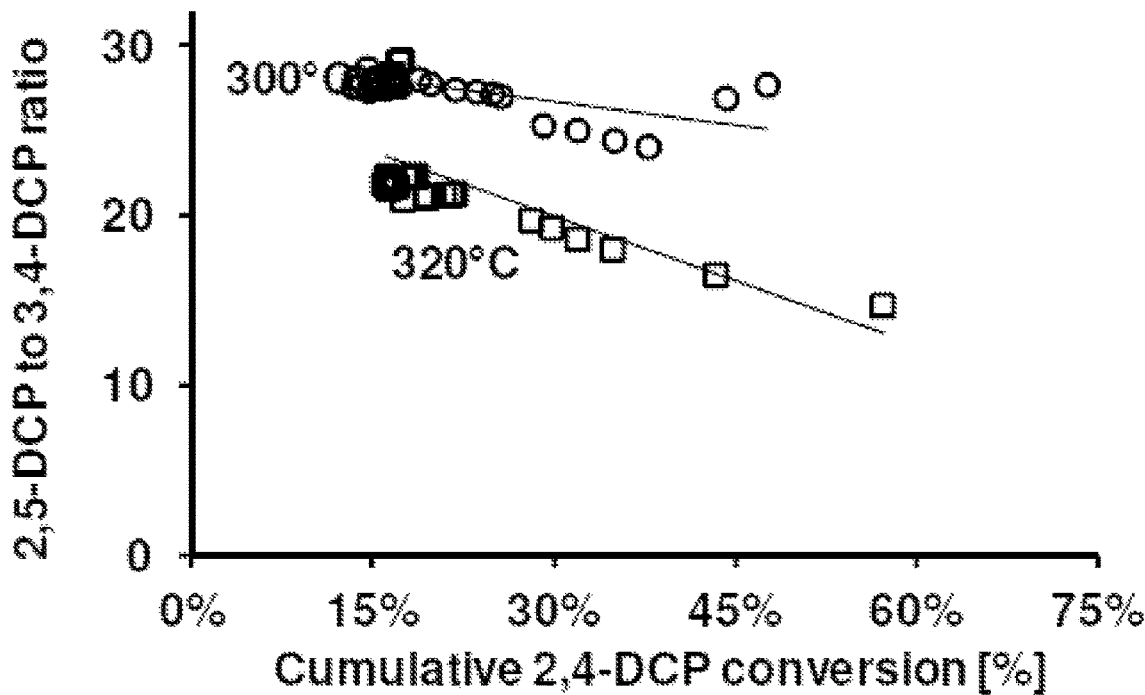
FIG. 10 presents a graph of the ratio of 2,5-dichlorophenol to 3,4-dichlorophenol as a function of cumulative 2,4-dichlorophenol conversion at various catalyst temperatures.
Figure 11:
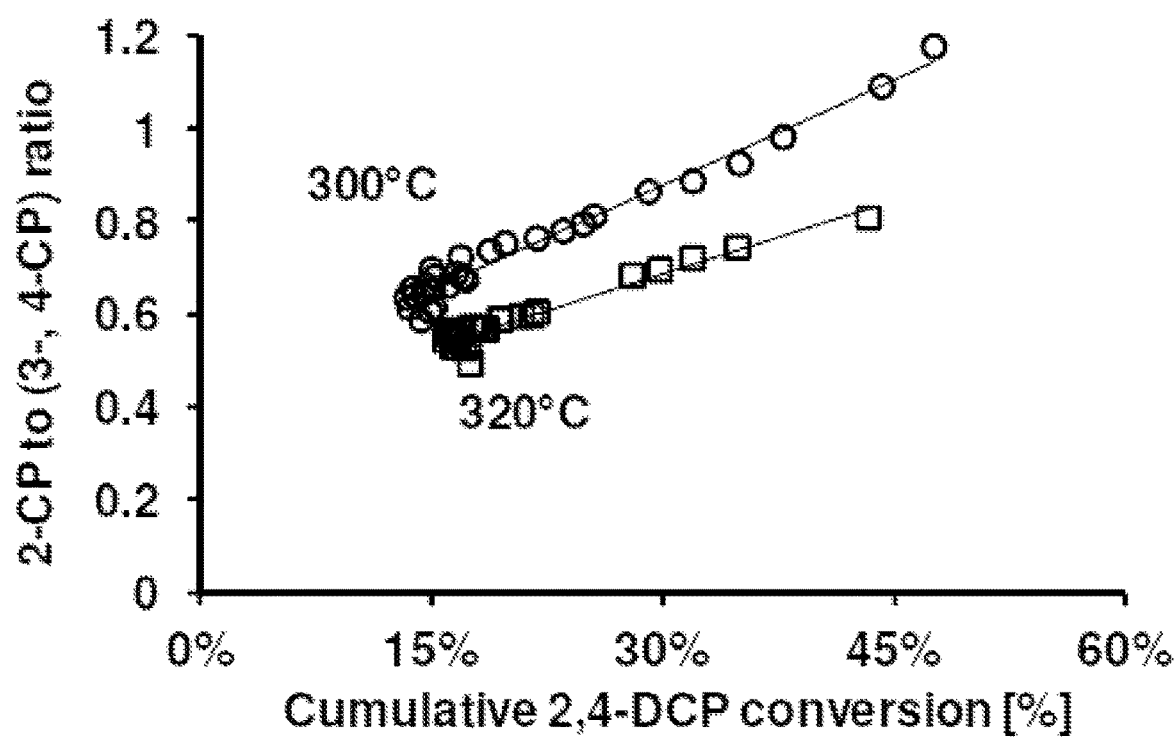
FIG. 11 presents a graphs of the ratio of 2-chlorophenol to 3- and 4-chlorophenol as a function of cumulative 2,4-dichlorophenol conversion at various catalyst temperatures.

The results show that decreasing the temperature increases the selectivity for 2,5-dichlorophenol, which may indicate that the off-target isomerization and other thermal decomposition are suppressed at lower temperatures. FIG. 10 shows the ratio of 2,5-dichlorophenol to 3,4-dichlorophenol at the tested temperatures and FIG. 11 shows the ratio of 2-chlorophenol to 3- and 4-chlorophenol at the tested temperatures. The results show that the ratio increased with decreasing reaction temperature.

Example 5: Effect of 2,4-DCP Partial Pressure on Conversion and Productivity of Isomerization Example 2 was repeated except a HZSM-5 catalyst having a SiO$_2$/Al$_2$O$_3$ mole ratio of 23 was used, temperature was 300° C., gas flow rate was varied from 173 cm$^3$/min to 345 cm$^3$/min, and 2,4-dichlorophenol partial pressure was varied from 0.26 kPa to 1.2 kPa. The 2,5-dichlorophenol steady-state formation rate is reported as mmol of 2,5-dichlorophenol over gram of catalyst over time in hours (i.e., mmol/g/h). The results of this experiment are provided in Table 5.

The results show that increasing the partial pressure of 2,4-dichlorophenol by 2-fold decreased 2,4-dichlorophenol conversion, but dramatically increased the 2,5-dichlorophenol formation rate which translated to higher productivity of 2,5-dichlorophenol. The results also show the increasing the space velocity of 2,4-dichlorophenol (i.e. gas flow rate) by 2-fold decreased 2,4-dichlorophenol conversion, but also dramatically increased the 2,5-dichlorophenol formation rate. Increased conversion is believed to benefit the process cost by reducing the amount of recycle stream. However, a higher productivity of 2,5-dichlorophenol is also desirable for efficacy of the process.

Example 6: Effect of Temperature on Selectivity, Conversion and Productivity of Isomerization Example 2 was repeated except a HZSM-5 catalyst having a SiO$_2$/Al$_2$O$_3$ mole ratio of 23 was used, gas flow rate was 173 cm$^3$/min, 2,4-dichlorophenol partial pressure was 0.59 kPa, and temperature was varied from 300° C. to 350° C. The 2,5-dichlorophenol steady-state formation rate is reported as mmol of 2,5-dichlorophenol over gram of catalyst over time in hours (i.e., mmol/g/h). The results of this experiment are provided in Table 6.

TABLE 5

Conversion and Productivity vs. 2,4-DCP Partial Pressure

SiO$_2$/Al$_2$O$_3$ mole ratio = 23; temperature = 300° C.; catalyst amount = 15 gram

| Exp. No. | Gas Flow Rate (cm$^3$/min) | 2,4-DCP partial pressure (kPa) | Time-on-stream (hour) | Weight over feed (gram × sec/gram) | Total feed in scrubber (mmol/L) | 2,5-DCP in scrubber (mmol/L) | 2,5-DCP stead-state Selectivity (%) | 2,4-DCP steady-state Conversion (%) | 2,5-DCP steady-state formation rate (mmol/g/h) |
|---|---|---|---|---|---|---|---|---|---|
| 5.1 | 173 | 1.2 | 25 | 33750 | 511 | 87 | 91 | 17 | 0.058 |
| 5.2 | 173 | 0.59 | 54 | 67500 | 513 | 95 | 90 | 18 | 0.026 |
| 5.3 | 345 | 0.59 | 25 | 67500 | 519 | 74 | 91 | 14 | 0.052 |
| 5.4 | 345 | 0.26 | 54 | 135000 | 498 | 83 | 90 | 18 | 0.026 |

TABLE 6

Selectivity, Conversion and Productivity vs. Temperature $SiO_2/Al_2O_3$ mole ratio = 23; gas flow rate = 173 cm$^3$/min;
2,4-dichlorophenol partial pressure = 0.59 kPa, catalyst amount = 15 gram

| Exp. No. | Catalyst Temperature (° C.) | Time-on-stream (hour) | Weight over feed (gram × sec/gram) | Total feed in scrubber (mmol/L) | 2,5-DCP in scrubber (mmol/L) | 2,5-DCP steady-state Selectivity (%) | 2,4-DCP steady-state Conversion (%) | 2,5-DCP steady-state formation rate (mmol/g/h) |
|---|---|---|---|---|---|---|---|---|
| 6.1 | 300 | 94 | 67500 | 648 | 107 | 90 | 18 | 0.026 |
| 6.2 | 350 | 92 | 67500 | 648 | 105 | 85 | 19 | 0.027 |

The results confirm that decreasing the temperature increases the selectivity for 2,5-dichlorophenol. The results show that the temperature did not have a significant effect on both the 2,4-dichlorophenol conversion and the 2,5-dichlorophenol formation rate. There are two isomerization reactions: (1) the forward isomerization reaction from 2,4-dichlorophenol to 2,5-dichlorophenol and (2) the reverse isomerization reaction from 2,5-dichlorophenol to 2,4-dichlorophenol. The temperature independency of conversion and formation rate has suggested that both forward and reverse isomerization reactions have similar activation energy and are locally equilibrated near the active sites, which are predominately located inside the pores of catalyst.

Example 7: Effect of Co-feeding 3,4-DCP on Selectivity of Isomerization

Example 2 was repeated except a HZSM-5 catalyst having a $SiO_2/Al_2O_3$ mole ratio of 30 was used, temperature was 300° C., feed composition was varied from approximately 100% of 2,4-dichlorphenol to a mixture of approximately 10% of 2,5-dichlorophenol and approximately 90% of 2,4-dichlorophenol to a mixture of approximately 10% of 2,5-dichlorophenol, approximately 87% of 2,4-dichlorphenol, and 2.6% of 3,4-dichlorophenol, and the partial pressure of total dichlorophenols was 0.26 kPa. The results of this experiment are provided in Table 7.

The results show that the presence of 2,5-dichlorphenol in the feed decreased the 2,5-dichlorophenol selectivity by approximately 6%. It is believe that the presence of 2,5-dichlorophenol in the feed increases the off-target isomerization to 3,4-dichlorophenol. The results show that the selectivity can be improved by co-feeding 3,4-dichlorophenol into the feed mixture containing 2,5-dichlorophenol. It is believed that co-feeding 3,4-dichlorophenol may advantageously shift the equilibrium to favor 2,5-dichlorphenol formation.

Example 8: Effect of Meso-porosity of Catalyst on Conversion of Isomerization

The commercial zeolites (e.g., $NH_4$—ZSM-5) in Example 2 were subjected to a desilication procedure or a desilication-dealumination procedure in an attempt to increase the meso-porosity of catalyst.

The catalysts were desilicated following the procedure described below. An aqueous solution of NaOH (0.2 M, 1.2 L) was prepared by using de-ionized water followed by heating to 65° C. The H-ZSM5 zeolite catalyst ($SiO_2/Al_2O_3$ mole ratio=55) (80 g) was placed in the flask with the aforementioned aqueous NaOH solution and the resulting solution was heated at 65° C. for 30 minutes. The cooled slurry was then centrifuged and washed with water, and dried. The resulting solids were placed in an aqueous solution of $(NH_4)_2SO_4$ (1 M) at a concentration of 25 mL/gram of zeolite and the solution was heated at 80° C. for 2 hours. After being separated by centrifuge, the solids were heated with another portion of $(NH_4)_2SO_4$ solution (1 M) at 80° C. for additional 2 hours. The obtained solids after centrifuge/wash cycles were dried in the oven at 80° C. These materials were then calcined in air at 550° C. for 24

TABLE 7

Selectivity vs. Composition of feed $SiO_2/Al_2O_3$ mole ratio = 30; Temperature = 300° C.;
Time-on-stream = ~95 hours

| Exp. No. | Molar Feed Composition Ratio (2,5-DCP:2,4-DCP:3,4-DCP) | Partial Pressure (kPa) | Catalyst Amount (gram) | Weight over feed (gram × sec/gram) | 2,5-DCP stead-state Selectivity (subtracted) (%) | 2,4-DCP steady-state Conversion (subtracted) (%) |
|---|---|---|---|---|---|---|
| 7.1 | 0:100:0 | 0.26 | 8 | 72000 | 91 | 15 |
| 7.2 | 10:90:0 | 0.26 | 12 | 108000 | 85 | 18 |
| 7.3 | 10:87:2.6 | 0.26 | 12 | 108000 | 89 | 19 | hours to remove any organic template and to convert the zeolites to acid (proton) form (i.e., HZSM-5).

Selected catalysts were also dealuminated following the procedure described below. A portion of the aforementioned desilicated zeolite was placed in an aqueous tartaric acid solution (1 M, 20 mL per gram of zeolite) at 60° C. for 4 hours. The solids were centrifuged and washed with deionized water several times before they were dried in an oven at 80° C. These materials were then calcined in air at 550° C. for 24 hours to remove any organic template prior to use for isomerization.

The results of surface area and porosity of commercial, desilicated, desilicated-dealuminated zeolites are provided in Table 8-A.

TABLE 8-A

Zeolite Surface Area and Porosity

| | | H-ZSM-5 Zeolite, $SiO_2/Al_2O_3$ mole ratio = 55 | | |
|---|---|---|---|---|
| | | Parent | Desil- icated | Desil- icated- Dealu- minated |
| Degas conditions (° C.) | | 350 | 350 | 350 |
| Calculated surface area ($m^2/g$) | by BET method | 429 | 438 | 444 |
| | by Langmuir method | 428 | 432 | 437 |
| Total meso-macro pore volume >20 Å to 2500 Å ($cm^3/g$) | by BJH method | 0.096 | 0.264 | 0.271 |
| H-K total micro pore volume ≤20 Å ($cm^3/g$) | | 0.172 | 0.177 | 0.179 |
| Total pore volume ($cm^3/g$) | | 0.266 | 0.441 | 0.451 |
| Median pore width (Å) | | 5.54 | 5.64 | 5.69 |

The results show that the desilication process increases the meso-porosity by about 2.75 fold comparing to parent zeolite, while maintaining the same median pore widths and micro pore volumes in all parent, desilicated, and desilicated-dealuminated zeolites. Table 8-B shows the pore volume distribution of the parent (unmodified), desilicated, and desilicated-dealuminated H-ZSM-5 zeolites.

TABLE 8-B

Pore Volume Distributions of H-ZSM-5 Zeolite, $SiO_2/Al_2O_3$ mole ratio = 55

| | Pore volume ($cm^3/g$) | | |
|---|---|---|---|
| Incremental pore diameter (Å) | Parent zeolite | Desilicated zeolite | Desilicated- Dealuminated zeolite |
| <20 | 0.172 | 0.177 | 0.179 |
| 20-40 | 0.024 | 0.033 | 0.033 |
| 40-80 | 0.011 | 0.036 | 0.036 |
| 80-150 | 0.009 | 0.048 | 0.050 |
| 150-400 | 0.015 | 0.042 | 0.045 |
| 400-1000 | 0.018 | 0.044 | 0.045 |
| 1000-2000 | 0.019 | 0.062 | 0.063 |
| 2000-3000 | 0 | 0 | 0 |
| Total pore volume ($cm^3/g$) | 0.266 | 0.441 | 0.451 |

Figure 12:
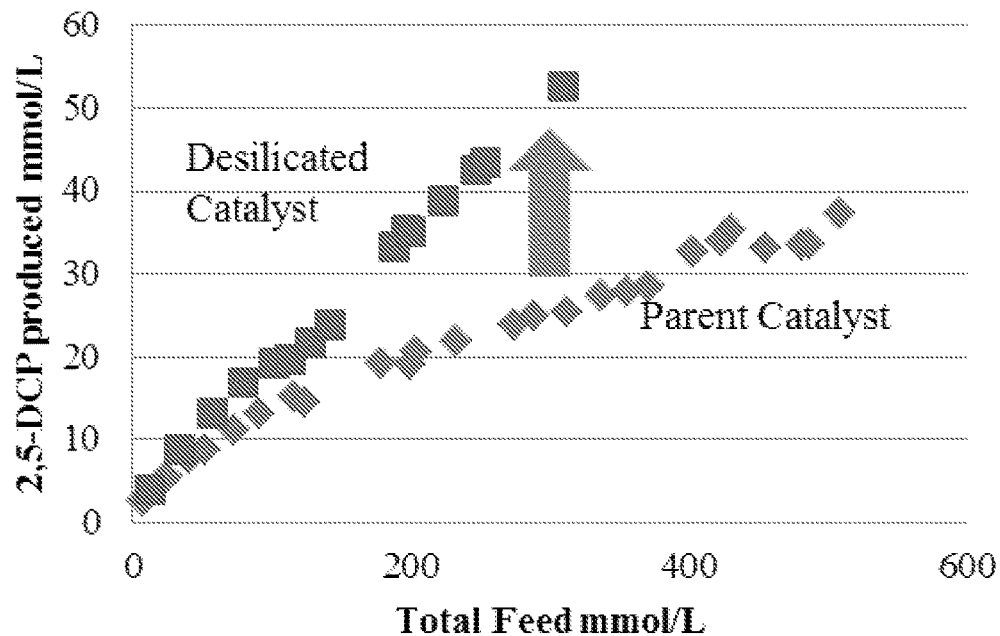
FIG. 12 shows the 2,5-dichlorophenol productivity for an unmodified ZSM-5 zeolite and desilicated ZSM-5 zeolite.
Figure 13:
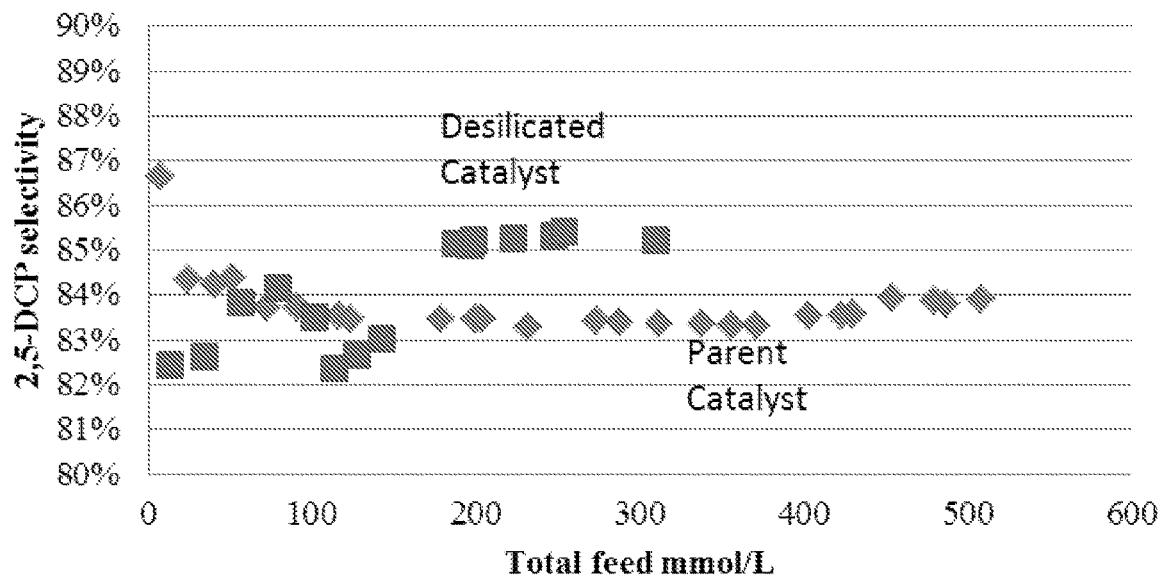
FIG. 13 shows the 2,5-dichlorophenol selectivity for an unmodified ZSM-5 zeolite and desilicated ZSM-5 zeolite.

Example 2 was repeated except parent, desilicated, and desilicated-dealuminated HZSM-5 catalysts having a $SiO_2/Al_2O_3$ mole ratio of 55 were used, temperature was 300° C., gas flow rate was 345 $cm^3$/min, and 2,4-dichlorophenol partial pressure was 0.26 kPa. The results of this experiment are provided in Table 8-C. FIGS. 12 and 13 show the 2,5-dichlorophenol productivity and selectivity for the desilicated catalyst (square) and parent catalyst (diamond).

TABLE 8-C 2,4-Dichlorophenol Conversion vs. Catalyst Porosity $SiO_2/Al_2O_3$ mole ratio = 55; Temperature = 300° C.;
gas flow rate = 345 $cm^3$/min; 2,4-dichlorophenol
partial pressure = 0.26 kPa; catalyst amount = 8 gram;
time-on-stream = 24 hours; weight over feed = 72000 (gram × sec/gram)

| Exp. No. | Type of Zeolites | Meso-micro pore volume >20 Å to 2500 Å ($cm^3/g$) | 2,5-DCP stead-state Selectivity (%) | 2,4-DCP steady-state Conversion (%) | 2,5-DCP steady-state formation rate (mmol/g/h) |
|---|---|---|---|---|---|
| 8.1 | Parent H-ZSM-5 | ~0.10 | 83 | 11 | 0.030 |
| 8.2 | Desilicated H-ZSM-5 | ~0.26 | 84 | 19 | 0.050 |
| 8.3 | Desilicated- dealuminated H-ZSM-5 | ~0.27 | 83 | 14 | 0.035 |

The results show that the 2,4-dichlorophenol conversion and the 2,5-dichlorophenol formation rate increased with the desilicated catalyst by about 2-fold, while maintaining the same 2,5-dichlorophenol selectivity. However, further dealumination of desilicated catalyst had negative effect on the 2,4-dichlorophenol conversion and the 2,5-dichlorophenol formation rate, compared to the desilicated catalyst. Similar yield between the parent and desilicated-dealuminated catalysts was observed based on similar $SiO_2/Al_2O_3$ ratios, regardless of the difference in their meso-micro pore volumes. It suggested that the increase in diffusivity and mesoporosity had only a minor influence on the 2,5-dichlorophenol yield. Although not entirely understood, it is believed that increasing of meso-pore volumes of catalyst by desilication increases the concentration of accessible active acid sites. The significantly higher yield with desilicated catalyst suggested that the acid sites in the catalyst pore mouth region are predominantly responsible for a higher yield of 2,5-dichlorophenol from isomerization of 2,4-dichlorophenol.

Example 9: Effect of Water on Selectivity, Conversion and Productivity of Isomerization Example 2 was repeated except a HZSM-5 catalyst having a $SiO_2/Al_2O_3$ mole ratio of 23 was used, temperature was 300° C., gas flow rate was 345 cm³/min, 2,4-dichlorophenol partial pressure was varied from 0.14 kPa to 0.26 kPa, and steaming was varied from no steam to periodic co-feed steam into the reactor (see Table 9-B for water co-feed regiment) in the experiment 9.2. The results of this experiment are presented in Table 9-A.

The results show that co-feeding a small amount of water decreased the 2,5-dichlorophenol selectivity and increased the off-target monochlorophenols. It is believed that water interacts with the chlorine group of phenols and accelerates the dechlorination pathway.

Figure 14:
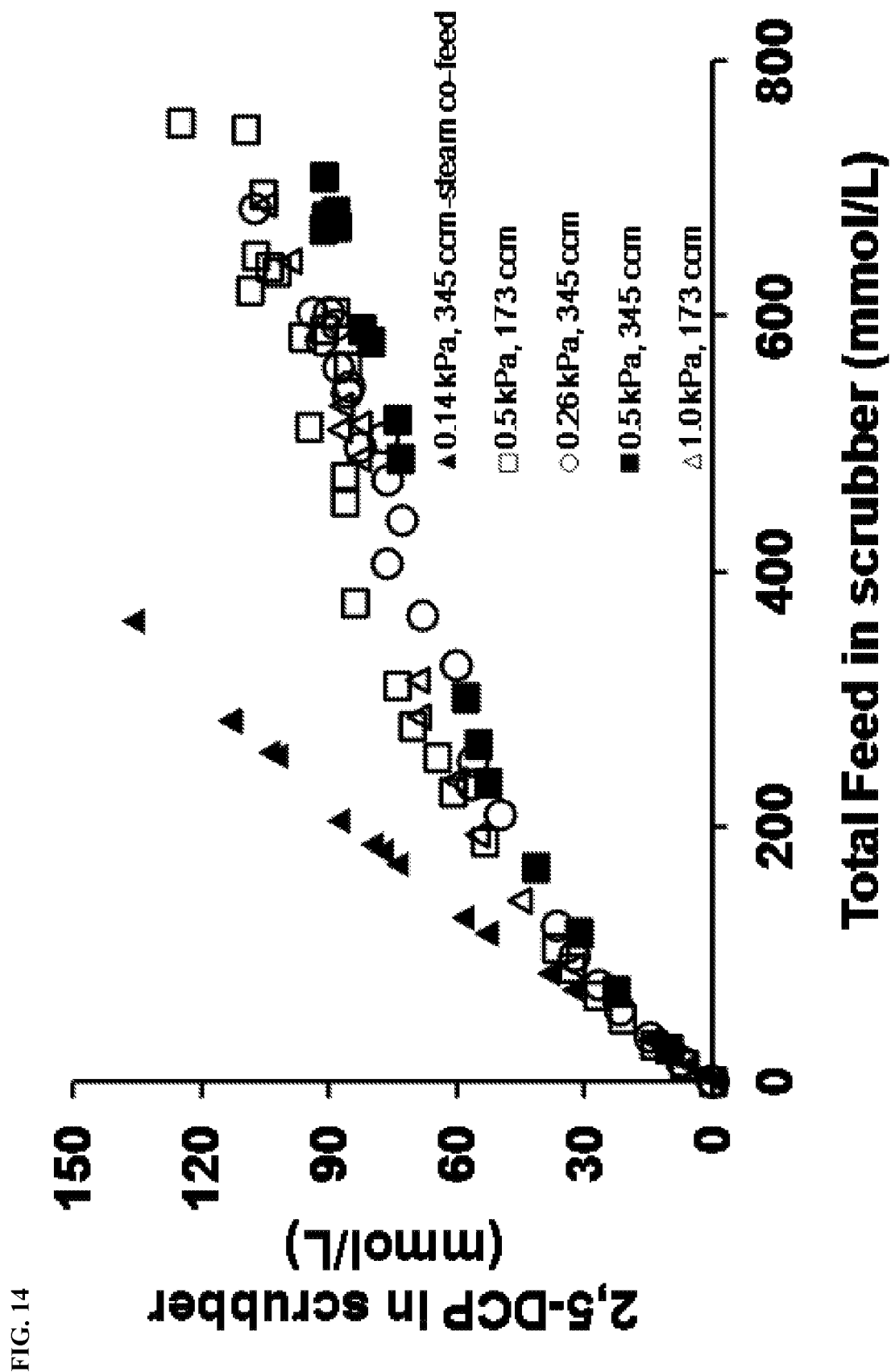
FIG. 14 shows the yield of 2,5-dichlorophenol for the reaction with and without periodic co-fed steam.

The results also show that the yield of 2,5-dichlorophenol for the reaction with the periodic co-feed steam was significantly improved. It was observed that steam appeared to prevent significant catalyst deactivation as shown in FIG. 14. The initial slopes of the 2,5-dichlorophenol per total feed in scrubber were similar for reactions with and without water at different 2,4-dichlorophenol partial pressures, but this initial slope was maintained only for the reaction with steam as a co-feed (triangle in FIG. 14). Without bound to theory, it is believed that the steam most likely reacts with or reduces the binding energies of the large aromatic species that are irreversibly bound to the active sites of catalyst under the reaction conditions, allowing the bound molecules to dissociate from the zeolite.

Example 10: Effect of Water on Rejuvenation of Catalyst and Isomerization

Figure 15:
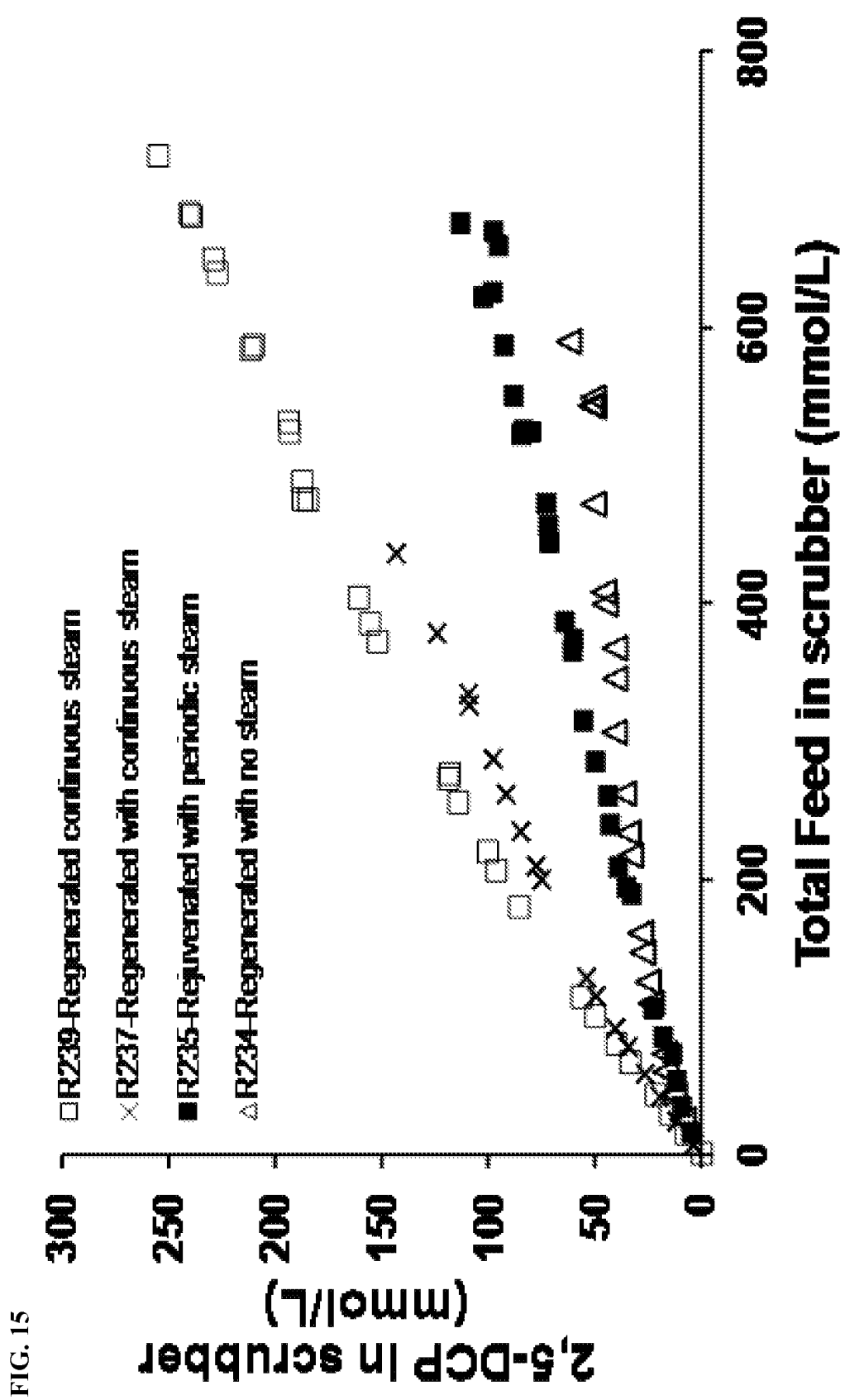
FIG. 15 shows the yield of 2,5-dichlorophenol for the reaction with and without co-fed steam.

Example 2 was repeated except a HZSM-5 catalyst having a $SiO_2/Al_2O_3$ mole ratio of 23 was used, temperature was 300° C., gas flow rate was 345 cm³/min, 2,4-dichlorophenol partial pressure was 0.26 kPa, and steaming was varied from no steam, to periodic co-feed steam (see Table 10-B for water co-feed regiment), and to continuous co-feed steam at a low level. The catalysts in Experiments 10.1, 10.2, and 10.3 were subjected to desilication at 80° C. in 0.2 M NaOH for 30 minutes, using the procedure described in Example 8. The regeneration of catalyst was carried out at 550° C. in air for 5 hours, followed by purging with $N_2$ at 550° C. for approximately 2 hours prior to use. The rejuvenation of catalyst was carried out in steam (0.06 g/min) at 300° C. for 1 hour, followed by purging with $N_2$ at 300° C. for approximately 2 hours prior to use. The results of this experiment are presented in Table 10-A and FIG. 15 show the 2,5-dichlorophenol per total feed in the scrubber for no steam (triangle), for periodic co-feed steam (solid square), for continuous co-feed steam at a 0.02 g/h rate (x), and for continuous co-feed steam at a 0.077-0.039 g/h rate (hollow square).

TABLE 9-A

Selectivity and Conversion vs. Water in the feed $SiO_2/Al_2O_3$ mole ratio = 23; temperature = 300° C., gas flow rate = 345 cm³/min; catalyst amount = 15 gram

| Exp. No. | Partial Pressure (kPa) | Weight over feed (gram × sec/gram) | Time-on-stream (hour) | Water in the feed (g/min) | Total feed in scrubber (mmol/L) | 2,5-DCP in scrubber (mmol/L) | 2,5-DCP stead-state Selectivity (%) | Mono-CP steady-state Selectivity (%) | 2,4-DCP steady-state Conversion (%) |
|---|---|---|---|---|---|---|---|---|---|
| 9.1 | 0.26 | 108000 | 36 | 0 | 366 | 68 | 90 | 6 | 21% |
| 9.2 | 0.14 | 58100 | 92 | 0.06* | 360 | 136 | 84 | 11 | 45% |

*See time in Table 9-B for water feeding over 92 hours, a total of approximately 2.1 mL of water was co-fed periodically

TABLE 9-B

Periodic Water Co-feed Regiment

| Reaction Time (Hour) | Periodical Steam at 0.06 g/min (second) |
|---|---|
| 0, 2, 4, 6, 8, 10, 12 14 | 60 |
| 23 | 150 |
| 26, 29, 32, 35, 44, 48, 51 | 90 |
| 54, 68, 71 | 180 |
| 74 | 90 |
| 77 | 180 |
| | Total amount of water: ~2.1 mL |

TABLE 10-A

Selectivity, Conversion and Productivity vs. Water in the feed
$SiO_2/Al_2O_3$ mole ratio = 23; temperature = 300° C.; gas flow rate = 345 cm³/min;
2,4-dichlorophenol partial pressure = 0.26 kPa

|  | Exp. No. | | | |
| --- | --- | --- | --- | --- |
| Reaction conditions | 10.1 | 10.2 | 10.3 | 10.4 |
| Catalyst, desilicated at 80° C. in 0.2M NaOH | yes | yes | yes | no |
| Catalyst, regenerated at 550° C. in air | yes | no | yes | yes |
| Catalyst, rejuvenated at 300° C. in steam (0.06 g/min) | no | 1 hour | no | no |
| Catalyst amount (g) | 8 | 8 | 8 | 15 |
| Water in the feed (g/hour) | 0 | periodic 0.04[a] | continuous 0.02[b] | continuous 0.077-0.039[c] |
| Weight over feed (gram × sec/gram) | 72000 | 72000 | 72000 | 108000 |
| Time-on-stream (hour) | 40 | 43 | 41 | 48 |
| Total feed in scrubber (mmol/L) | 368 | 373 | 334 | 372 |
| 2,5-DCP in scrubber (mmol/L) | 41 | 61 | 110 | 153 |
| Mono-CP steady-state selectivity (%) | 4 | 9 | 6 | 10 |
| 2,5-DCP stead-state selectivity (%) | 92 | 88 | 90 | 86 |
| 2,4-DCP steady-state conversion (%) | 12 | 19 | 37 | 48 |
| 2,5-DCP formation rate (mmol/gram/hour) | 0.033 | 0.050 | 0.096 | 0.070 |

[a]See time in Table 10-B for water feeding regiment, a total of approximately 3.3 mL of water was co-fed periodically;
[b]continuous steaming at 0.02 mL/hour, a total of approximately 1.05 mL of water was co-fed;
[c]continuous steaming at 0.077 mL/hour from 0-25 hours, changed to 0.0385 mL/hour from 25-96 hours.

TABLE 10-B

Periodic Water Co-feed Regiment in experiment 10.2

| Reaction Time (Hour) | Periodical Steam at 0.06 g/min (second) |
| --- | --- |
| 7 | 300 |
| 20, 31, 43, 55 | 600 |
| 67, 79 | 300 |
| | Total amount of water: ~3.3 mL |

The results from Experiments 10.1 and 10.2 in FIG. 15 (R234 and R235) show that the initial slopes of the 2,5-dichlorophenol per total feed in scrubber were similar for reactions with the regenerated catalyst in air at 550° C. and the rejuvenated catalyst in steam at 300° C. It demonstrated that the activity of catalyst can be fully recovered by the steam-assisted rejuvenation method. Rejuvenating the catalyst without heating the catalyst bed to an elevated temperature would reduce the utility costs considerably and increase the reactor on-stream time. Therefore, it would be more cost effective for the operation of the reactor in process.

The results confirmed that the yield of 2,5-dichlorophenol per total feed in scrubber for the reaction with the periodic co-feed steam was significantly improved compared to the reaction without steam. It was found that continuously co-feeding lower level of steam enhanced the yield of 2,5-dichlorophenol even more effectively than the periodically co-feeding, shown in Table 10-A (Experiments 10.3 and 10.2) and in FIG. 15 (R237 vs. R235). It is believed that the continuous co-feed of steam at a low level helps to maintain the active sites more efficiently than using periodic co-feed of steam at a higher level. The observed decreased selectivity was due to the formation of monochlorophenols in presence of water and was consistent with previous experiment results. However, with continue co-feed steam at a much slower rate of 0.02 g/hour, both the 2,4-dichlorophenol conversion and 2,5-dichlorophenol formation rate had about 3-fold increase with minimized loss of approximately 2% selectivity compared to the one without steam. The yield of 2,5-dichlorophenol per total feed in scrubber and 2,4-dichlorophenol conversion can be further increased with an increased amount of catalyst, shown in Table 10-A (8 gram catalyst in Experiment 10.3 vs. 15 gram catalyst in Experiment 10.4) and in FIG. 15 (R237 vs. R239). The results also show that the ratio of steam to the amount of catalyst can be an important factor to 2,5-dichlorophenol selectivity while maximizing the catalyst stability through steam cleaning. Overall, co-feeding steam during the isomerization of 2,4-dichlorophenol to 2,5-dichlorophenol was found to be an effective method to regenerate the spent catalyst, maintain catalyst activity, and increase the 2,5-dichlorophenol productivity.

Example 11: Effect of Water on Regeneration of Catalyst and Isomerization

Example 2 was repeated except a H-ZSM-5 catalyst having a $SiO_2/Al_2O_3$ mole ratio of 23, temperature was 300° C., gas flow rate was 345 cm³/min, and 2,4-dichlorophenol partial pressure was 0.26 kPa. The catalyst used in Experiment 11.2 was pretreated at 700° C. with water as steam (0.058 g/hr) under $N_2$ for 2-3 hours prior to use. The results of this experiment are presented in Table 11.

TABLE 11

Isomerization using the Catalyst Pretreated with Water $SiO_2/Al_2O_3$ mole ratio = 23; temperature = 300° C.,
gas flow rate = 345 cm³/min; 2,4-dichlorophenol partial pressure = 0.26 kPa catalyst
amount = 15 gram; weight over feed = 108000 (gram × sec/gram)

| Exp. No. | Catalyst pretreatment under $N_2$ prior to use | Time-on-stream (hour) | Total feed in scrubber (mmol/L) | 2,5-DCP in scrubber (mmol/L) | 2,5-DCP stead-state Selectivity (%) | Mono-CP steady-state Selectivity (%) | 2,4-DCP steady-state Conversion (%) | 2,5-DCP steady-state formation rate (mmol/g/h) |
|---|---|---|---|---|---|---|---|---|
| 11.1 | No water | 84 | 684 | 108 | 90 | 6 | 18 | 0.032 |
| 11.2 | Water* | 85 | 707 | 47 | 80 | 14 | 8 | 0.011 |

*water as steam (0.058 g/hr) under $N_2$ at 700° C. for 2-3 hours

The results show that the yield of 2,5-dichlorophenol over the total feed in the scrubber, the 2,4-dichlorophenol conversion, and the formation rate of 2,5-dichlorophenol decreased significantly by using the catalyst that was pretreated with water under $N_2$ at 700° C. for several hours. The decrease of both the 2,4-dichlorophenol conversion and the 2,5-dichlorophenol selectivity, caused by the water pretreatment of catalyst, was most likely resulted from the loss of the active acid sites by dealumination. The dealumination was believed to subsequently increase the concentration of defect (inactive) sites and potentially resulted in the increase of the $SiO_2/Al_2O_3$ ratio. The decreased active sites contributed to the decrease of the 2,5-dichlorophenol selectivity and favored the formation of off-target monochlorophenols. As discussed previously in Example 9, water remained in the catalyst might also accelerate the dechlorination pathway by interacting with the chlorine group of phenols.

To maintain the desired isomerization results with reproducible 2,5-dichlorophenol selectivity, 2,4-dichlorophenol conversion and 2,5-dichlorophenol yield, it is important to keep water/steam out during the generation of catalysts at a higher temperature (e.g. 700° C.) prior to use.

Figure 16:
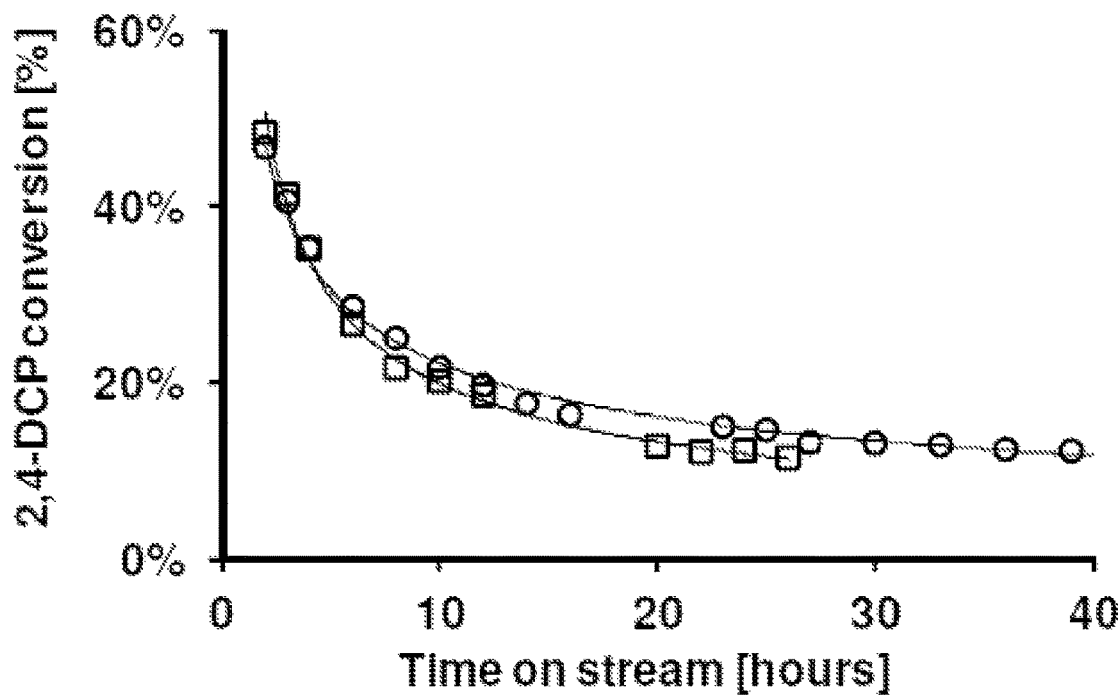
FIG. 16 shows the 2,4-dichlorophenol conversion for the fresh catalyst (square) and regenerated catalyst (circle) as a function of time on stream.
Figure 17:
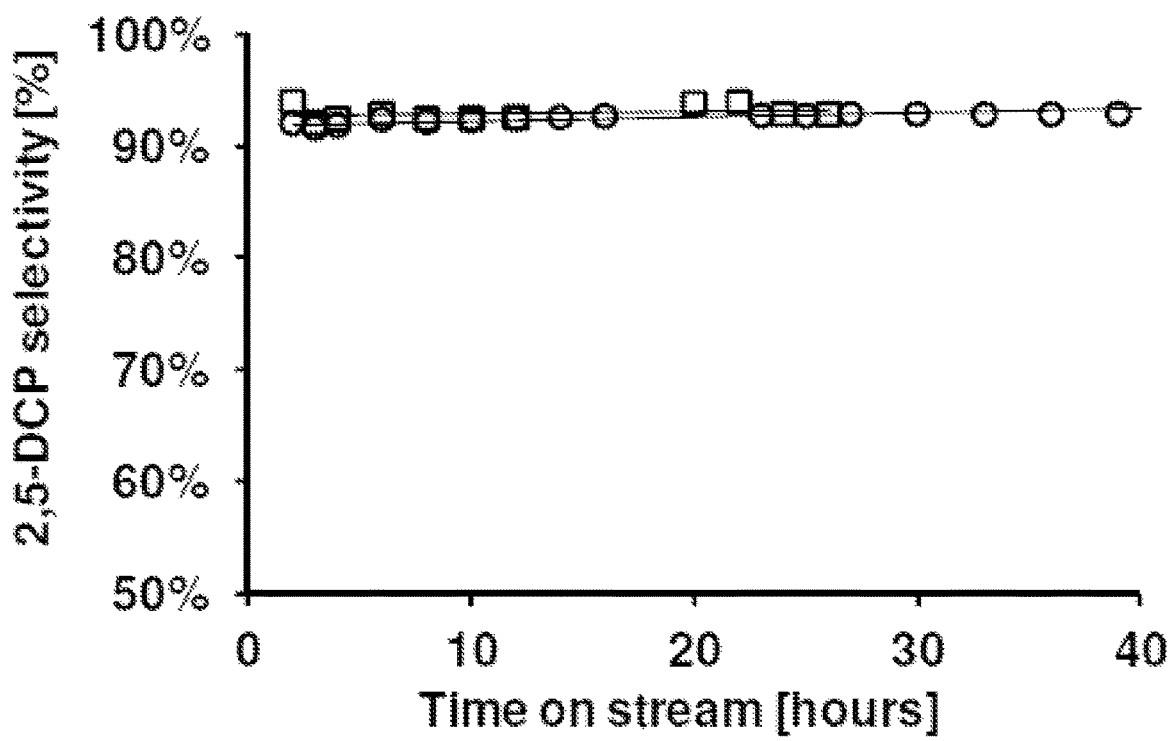
FIG. 17 shows the 2,5-dichlorophenol selectivity for the fresh catalyst (square) and regenerated catalyst (circle) as a function of time-on-stream.

Example 12: Effect of Regenerated Catalysts on Selectivity and Conversion of Isomerization Catalysts used in Example 2 were regenerated in-situ by air calcination at 550° C. Example 2 was repeated except the regenerated catalysts were used. FIG. 16 shows the 2,4-dichlorophenol conversion for the fresh catalyst (square) and regenerated catalyst (circle) as a function of time-on-stream. FIG. 17 shows the 2,5-dichlorophenol selectivity for the fresh catalyst (square) and regenerated catalyst (circle) as a function of time-on-stream. The results show that the regenerated catalyst performed closely to that of the fresh catalyst.

Example 13: Preparation of Catalysts for Hydroxylation of 1,4-Dichlorobenzene

Commercial zeolites (e.g., $NH_4$-ZSM-5) at various $SiO_2/Al_2O_3$ mole ratio ratios were acquired from a zeolite vendor. These materials were then calcined in air at 550° C. for 24 hours to remove any organic template and to convert the zeolites to acid (proton) form (i.e., HZSM-5). In some instances, iron was ion exchanged to the zeolite pores using $Fe(NO_3)_3$ in water by first stirring at room temperature for 4 hours and then heating the mixture at about 80° C. for about 12 hours. The cooled slurry was then centrifuged and washed with water, and dried under vacuum at approximately 70° C. in the presence of $N_2$ gas for about 12 hours.

The dried material was pelletized and was calcined at 550° C. in air for 24 hours before subsequent high temperature activation.

The high temperature activation of the catalysts was carried out either under argon gas up to 950° C. for 4-8 hours, or combined with steam using argon gas as a carrier at about 650° C.

In any cases of hydroxylation reactions, all zeolite catalysts were calcined in the reactor in-situ in nitrogen at 750° C. for 2 hours and then cooled to room temperature in about 12 hours prior to use.

Example 14: Hydroxylation of 1,4-Dichlorobenzene

Figure 18:
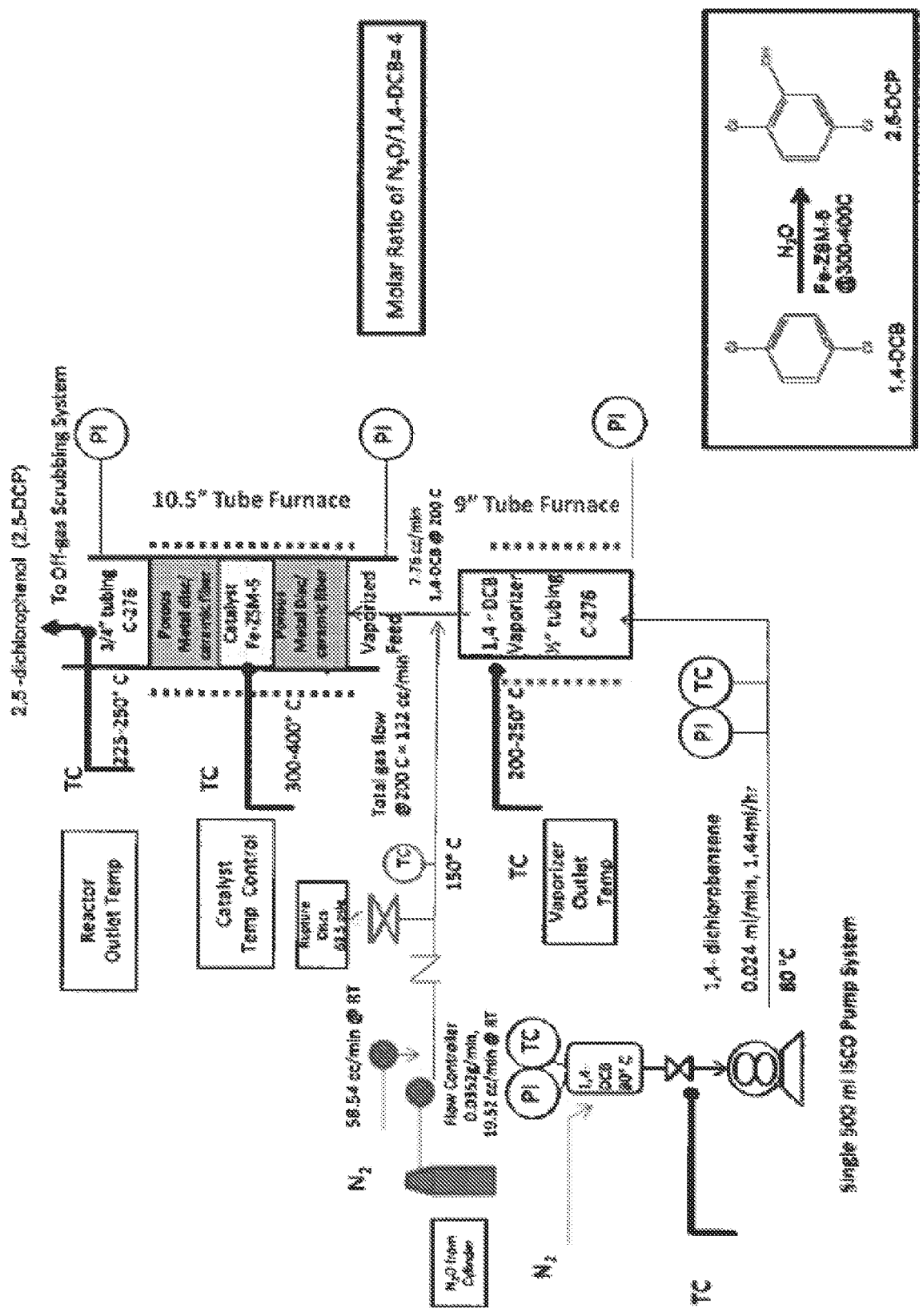
FIG. 18 shows the reactor setup for various experiments described in certain Examples.

After high temperature calcination of the zeolite catalysts in the reactor, gaseous 1,4-dichlorobenzene and $N_2O$ were fed to the reactor as described in Example 13. The reactor setup is shown in FIG. 18. The feed rate for 1,4-dichlorobenzene was 7.75 cm³/min at 200° C. The feed rate for the oxidizing agent $N_2O$ in $N_2$ was 132 cm³/min at 200° C. The gas-phase reactor temperature set points ranged from 350° C. to 400° C. and the $N_2O$ to 1,4-dichlorobenzene molar ratio was set at 4.

The first runs compared the performance of ZSM-5 ($SiO_2/Al_2O_3$ molar ratio=80) and a corresponding iron-exchanged material (with nominal $Fe_2O_3$ loading=0.4 wt %). The results indicated about a 10-fold increase in activity to dichlorophenol with the iron-exchanged ZSM-5 along with a selectivity for 2,5-dichlorophenol at about 75%. The hydroxylation activity was also observed to be sensitive to iron loading. In subsequent runs, the iron-exchanged ZSM-5 catalysts with nominal $Fe_2O_3$ loadings of 0.8 wt. % and 0.08 wt. % were tested. Selectivity for 2,5-dichlorophenol for these catalysts ranged from 75-90%. These results are shown in Tables 14-A, 14-B, and 14-C. Steaming and high-temperature treatment with the same $Fe_2O_3$ loading seemed to generate more stable activity as shown by runs 13 and 14 of Table 14-B.

TABLE 14-A

Catalyst $Fe_2O_3$ loading vs. Conversion $SiO_2/Al_2O_3$ molar ratio = 80;
$N_2O$ = 20 cm³/min; $N_2$ = 59 cm³/min;
activated by calcination at 900° C. in argon

| Exp. No. | Catalyst | $Fe_2O_3$ loading (wt %) | Catalyst amount (g) | Reactor temperature (° C.) | 1,4-DCB Conversion (%) |
|---|---|---|---|---|---|
| 14.1 | fresh | 0 | 3.25 | 350 | ~0.0 |
| 14.2 | spent | 0 | 3.25 | 350 | ~0.3 |
| 14.3 | spent | 0 | 3.25 | 400 | ~0.4 |

TABLE 14-A-continued

Catalyst $Fe_2O_3$ loading vs. Conversion $SiO_2/Al_2O_3$ molar ratio = 80;
$N_2O$ = 20 cm³/min; $N_2$ = 59 cm³/min;
activated by calcination at 900° C. in argon

| Exp. No. | Catalyst | $Fe_2O_3$ loading (wt %) | Catalyst amount (g) | Reactor temperature (° C.) | 1,4-DCB Conversion (%) |
|---|---|---|---|---|---|
| 14.4 | spent | 0 | 3.25 | 450 | ~0.5 |
| 14.5 | fresh | 0.40 | 2.6 | 400 | 4.6 |
| 14.6 | spent | 0.40 | 2.6 | 400 | 2.8 |

TABLE 14-B

Activation Method of Catalyst vs. Conversion $SiO_2/Al_2O_3$ molar ratio = 80,
$Fe_2O_3$ loading = 0.40 wt %, reactor temperature = 400° C.,
$N_2O$ = 20 cm³/min, $N_2$ = 59 cm³/min, catalyst amount = 2.6 gram

| Exp. No. | Catalyst | Activation Method | 1,4-DCB Conversion (%) |
|---|---|---|---|
| 14.5 | fresh | Calcined at 900° C. in argon | 4.6 |
| 14.6 | spent | Calcined at 900° C. in argon | 2.8 |
| 14.7 | fresh | Steamed at 650° C., then calcined at 900° C. in argon | 4.9 |
| 14.8 | spent | Steamed at 650° C., then calcined at 900° C. in argon | 7.5 |

TABLE 14-C

Catalyst $Fe_2O_3$ loading Amount vs. Selectivity and Conversion $SiO_2/Al_2O_3$ molar ratio = 80,
reactor temperature = 400° C., $N_2O$ = 20 cm³/min,
$N_2$ = 59 cm³/min, catalyst amount = 2.6 gram,
activated by calcination at 900° C. in argon

| Exp. No. | Catalyst | $Fe_2O_3$ loading (wt %) | 2,5-DCP Selectivity (%) | 1,4-DCB Conversion (%) |
|---|---|---|---|---|
| 14.9 | fresh | 0.80 | 77.9 | 1.6 |
| 14.10 | spent | 0.80 | 78.3 | 1.7 |
| 14.11 | fresh | 0.08 | 74.7 | 10.2 |
| 14.12 | spent | 0.08 | 91.0 | 2.1 |

In another set of runs, a zeolite catalyst (with nominal $Fe_2O_3$ loading of 0.08 wt %) was re-used four times with a total on-stream time of about 26 hours. A 2,5-dichlorophenol selectivity of approximately 90% was achieved throughout the run, although the reactor flow was blocked in the first day (Experiment 14.13), which compromised catalyst performance. A conversion of about 7% was still observed at the end of day 2 (Experiment 14.14). The results for these runs are shown in Table 14-D.

TABLE 14-D

Catalyst Re-usage vs. Selectivity and Conversion $SiO_2/Al_2O_3$ molar ratio = 80; $Fe_2O_3$ loading = 0.08 wt %;
reactor temperature = 400° C.;
$N_2O$ = 20 cm³/min; $N_2$ = 59 cm³/min;
catalyst amount = 2.6 gram; activated by calcination
at 900° C. in argon

| | Exp. No. | Catalyst | Time-on-stream (hour) | | | | | |
|---|---|---|---|---|---|---|---|---|
| | | | 1 | 2 | 3 | 4 | 5 | 6 |
| 2,5-DCP Selectivity (%) | 14.13* | fresh | 81.7 | 84.7 | — | — | — | — |
| | 14.14 | spent | 86.6 | 87.2 | 87.5 | 87.5 | 87.8 | 88.1 |
| | 14.15 | spent | 100.0 | 85.8 | — | 87.1 | 87.7 | 88.0 |
| | 14.16 | spent | 100.0 | 100.0 | 100.0 | 87.9 | 88.9 | 88.6 |
| | 14.17 | spent | — | 100.0 | 100.0 | 100.0 | 89.2 | 89.2 |
| 1,4-DCB Conversion (%) | 14.13* | fresh | 1.0 | 1.8 | — | — | — | — |
| | 14.14 | spent | 3.4 | 4.9 | 5.6 | 7.0 | 6.8 | 6.9 |
| | 14.15 | spent | 1.0 | 1.1 | — | 0.6 | 0.6 | 0.6 |
| | 14.16 | spent | 0.3 | 0.2 | 0.2 | 0.2 | 0.2 | 0.2 |
| | 14.17 | spent | — | 0.1 | 0.1 | 0.1 | 0.1 | 0.1 |

Example 15: Hydroxylation of 1,4-Dichlorobenzene at Various Catalyst Conditions

Example 14 was repeated except that catalyst calcination temperature, $SiO_2/Al_2O_3$ molar ratio, and $Fe_2O_3$ loading were varied. Table 15 presents the results of these runs.

TABLE 15

Compositions of Hydroxylation at Various Catalyst Conditions

| Exp. No. | Catalyst Calcination Temperature (° C.) | $SiO_2/Al_2O_3$ mole ratio | $Fe_2O_3$ loading (wt. %) | 2,5-DCP (%) | 2,4-DCP (%) | 3-CP (%) | 4-CP (%) | 2-CP (%) |
|---|---|---|---|---|---|---|---|---|
| 27 | 550 | 23 | 0 | 90.81 | 6.55 | 1.47 | 0 | 0.86 |
| 36-a | 500 | 30 | 0 | 85.38 | 11.96 | 1.41 | 0 | 1.14 |
| 34-a | 550 | 50 | 0 | 88.10 | 7.43 | 2.51 | 0 | 1.53 |
| 17 | 550 | 80 | 0 | 94.09 | 1.59 | 3.11 | 0.34 | 0.22 |
| 16 | 550 | 280 | 0 | 97.30 | 0.27 | 1.87 | 0 | 0 |
| 19 | 550 | 80 | 0 | 94.09 | 1.59 | 3.11 | 0.34 | 0.22 |
| 36 | 900 | 80 | 0 | 96.31 | 0.38 | 2.51 | 0.08 | 0.05 |
| 39 | 500 | 30 | 0 | 85.38 | 11.96 | 1.41 | 0 | 1.14 |
| 24 | 900 | 30 | 0 | 88.67 | 10.03 | 0.77 | 0 | 0.33 |
| 25 | 550 | 280 | 0.32 | 93.10 | 0.29 | 5.96 | 0 | 0.18 |
| 22 | 550 | 280 | 0.16 | 95.65 | 0 | 4.09 | 0 | 0 |
| 18 | 900 | 280 | 0 | 96.31 | 0.38 | 2.51 | 0.08 | 0.05 |
| 20 | 900 | 280 | 0.16 | 95.31 | 0.18 | 4.10 | 0 | 0.08 |
| 25 | 900 | 280 | 0.32 | 95.64 | 0 | 4.05 | 0 | 0 |

TABLE 15-continued

Compositions of Hydroxylation at Various Catalyst Conditions

| Exp. No. | Catalyst Calcination Temperature (° C.) | SiO$_2$/Al$_2$O$_3$ mole ratio | Fe$_2$O$_3$ loading (wt. %) | 2,5-DCP (%) | 2,4-DCP (%) | 3-CP (%) | 4-CP (%) | 2-CP (%) |
|---|---|---|---|---|---|---|---|---|
| 41 | 550 | 200 | 0.08 | 95.07 | 1.22 | 3.08 | 0 | 0.33 |
| 31 | 550 | 200 | 0.16 | 93.08 | 0.70 | 5.46 | 0 | 0.37 |
| 37 | 550 | 200 | 0.24 | 92.75 | 0.65 | 5.75 | 0 | 0.30 |
| 32 | 550 | 200 | 0.32 | 93.07 | 0.43 | 5.90 | 0 | 0.17 |
| 45 | 550 | 350 | 0.16 | 98.17 | 0 | 1.67 | 0 | 0 |

Example 16: Hydroxylation of 1,4-Dichlorobenzene at Various Reactor Conditions

Example 14 was repeated except that catalyst temperature (reaction temperature), carrier gas, and residence time were varied. Table 16 presents the results of these runs.

TABLE 16

Compositions of Hydroxylation at Various Reactor Conditions

| | Experiment Number | | | | | | | | |
|---|---|---|---|---|---|---|---|---|---|
| | 1 | 2 | 3 | 4 | 5 | 6 | 7 | 8 | 9 |
| Starting Material | 2,5-DCP | 2,5-DCP | 2,5-DCP | 2,5-DCP | 2,5-DCP | 2,5-DCP | 2,5-DCP | 2,4-DCP | 1,4-DCP |
| Temperature (° C.) | 370 | 290 | 310 | 305 | 370 | 370 | 330 | 330 | 330 |
| Time (min) | 30 | No hold | No hold | 5 | 30 | 15 | 15 | 15 | 15 |
| Headspace | Air | Argon | Argon | Argon | Argon | Argon | Argon | Argon | Argon |
| GC-EC Results (Mol %) | | | | | | | | | |
| 1,3-DCB | 0.00 | 0.00 | 0.00 | 0.00 | 0.00 | 0.00 | 0.00 | 0.00 | 0.11 |
| 1,4-DCB | 1.32 | 0.10 | 0.12 | 0.10 | 0.13 | 0.11 | 0.05 | 0.00 | 98.78 |
| 1,2-DCB | 0.19 | 0.42 | 0.43 | 0.57 | 0.41 | 0.12 | 0.12 | 0.95 | 0.42 |
| 2,4-DCP | 0.00 | 0.00 | 0.00 | 0.00 | 0.00 | 0.00 | 0.00 | 99.05 | 0.45 |
| 2,5-DP | 68.03 | 99.47 | 99.30 | 98.78 | 75.64 | 83.80 | 93.79 | 0.00 | 0.05 |
| 1,2,4-TCB | 0.59 | 0.01 | 0.15 | 0.02 | 0.18 | 0.09 | 0.02 | 0.00 | 0.00 |
| 3-CP | 29.87 | 0.00 | 0.00 | 0.55 | 23.64 | 15.88 | 6.01 | 0.00 | 0.19 |
| % degradation | 31.97 | 0.53 | 0.70 | 1.22 | 24.36 | 16.20 | 6.21 | 0.95 | 1.22 |

Example 17: Hydroxylation of 1,4-Dichlorobenzene at Various Temperatures

Example 14 was repeated except that catalyst bed temperature profile was varied. When the bed temperature was held at about 395° C., the conversion of 1,4-dichlorobenzene was over 20% by suppressing the isomerization. Isomerization was found to be not only a competitive reaction to 1,4-dichlorobenzene conversion to 2,5-dichlorophenol, but also negatively impacted the longer-term performance of the catalyst. In Experiment 17.1-17.3 & 17.4-17.6, two catalysts were prepared from the same precursor the same way (i.e., 900° C. calcined in argon for 4 hrs) but catalyst bed temperature profiles were different. As a result, 1,4-dichlorobenzene isomerization of 6.34% was observed in Experiment 17.1; while it was zero in Experiment 17.4. The resulting impact on 1,4-dichlorobenzene to 2,5-dichlorophenol conversion was significant. In Experiment 17.1, 1,4-dichlorobenzene conversion was about 20% (hr 3-5) versus 41% in Experiment 17.4 (hr 3-6); while selectivity stayed the same at about 66%. Results for these runs are shown in Table 17.

TABLE 17

Reaction Temperature, Selectivity and Conversion

SiO$_2$/Al$_2$O$_3$ molar ratio = 80; Fe$_2$O$_3$ loading = 0.08 wt %;
N$_2$O = 20 cm$^3$/min; N$_2$ = 59 cm$^3$/min;
catalyst amount = 2.6 gram; activated by calcination at 900° C. in argon

| | Exp. No. | Catalyst | Reactor temperature (° C.) | Time-on-stream (hour) | | | | | |
|---|---|---|---|---|---|---|---|---|---|
| | | | | 1 | 2 | 3 | 4 | 5 | 6 |
| Isomerization (%) | 17.1 | fresh | 370 | 6.3 | 3.6 | 3.4 | 2.4 | 2.2 | — |
| | 17.2 | spent | 340-360 | 0.0 | — | 0.0 | 0.0 | 0.0 | 0.0 |

TABLE 17-continued

Reaction Temperature, Selectivity and Conversion

SiO$_2$/Al$_2$O$_3$ molar ratio = 80; Fe$_2$O$_3$ loading = 0.08 wt %;
N$_2$O = 20 cm$^3$/min; N$_2$ = 59 cm$^3$/min;
catalyst amount = 2.6 gram; activated by calcination at 900° C. in argon

| | Exp. No. | Catalyst | Reactor temperature (° C.) | Time-on-stream (hour) | | | | | |
|---|---|---|---|---|---|---|---|---|---|
| | | | | 1 | 2 | 3 | 4 | 5 | 6 |
| | 17.3 | spent | 340-360 | 0.0 | 0.0 | 0.0 | 0.0 | 0.0 | 0.0 |
| | 17.4 | fresh | 340-360 | 0.0 | 0.7 | 0.2 | 0.2 | 0.1 | 0.1 |
| | 17.5 | spent | 345-365 | 0.0 | 0.0 | 0.0 | 0.0 | 0.0 | 0.0 |
| | 17.6 | spent | 350-365 | 0.0 | 0.0 | 0.0 | 0.0 | 0.0 | 0.0 |
| 2,5-DCP | 17.1 | fresh | 370 | 100.0 | 100.0 | 66.3 | 66.1 | 66.2 | — |
| Selectivity | 17.2 | spent | 340-360 | 100.0 | — | 73.3 | 70.7 | 70.2 | 70.0 |
| (%) | 17.3 | spent | 340-360 | 80.8 | 76.6 | 74.6 | 73.8 | 73.4 | 72.9 |
| | 17.4 | fresh | 340-360 | 82.5 | 72.7 | 67.1 | 66.3 | 66.0 | 65.7 |
| | 17.5 | spent | 345-365 | 73.7 | 70.9 | 71.3 | 69.7 | 69.2 | 69.2 |
| | 17.6 | spent | 350-365 | 81.2 | 80.5 | 78.5 | 80.5 | 80.9 | 81.0 |
| 1,4-DCB | 17.1 | fresh | 370 | 5.8 | 7.6 | 18.9 | 20.9 | 21.0 | — |
| Conversion | 17.2 | spent | 340-360 | 4.3 | — | 5.2 | 8.4 | 8.7 | 8.9 |
| (%) | 17.3 | spent | 340-360 | 2.7 | 3.1 | 3.6 | 3.8 | 4.4 | 4.4 |
| | 17.4 | fresh | 340-360 | 51.9 | 55.7 | 49.1 | 42.3 | 37.7 | 34.7 |
| | 17.5 | spent | 345-365 | 12.3 | 9.5 | 6.8 | 10.7 | 11.1 | 11.8 |
| | 17.6 | spent | 350-365 | 0.6 | 0.5 | 1.7 | 2.4 | 2.8 | 3.4 |

A trend of increasing selectivity for 2,5-dichlorophenol was observed when time-on-stream continued to run. In both series (Experiment 17.1-17.3 & 17.4-17.6), 2,5-dichlorophenol selectivity was found to increase as the catalysts aged. The reason for this observation is not known, but it is hypothesized, that the active sites causing lower selectivity might deactivate first.

Figure 19:
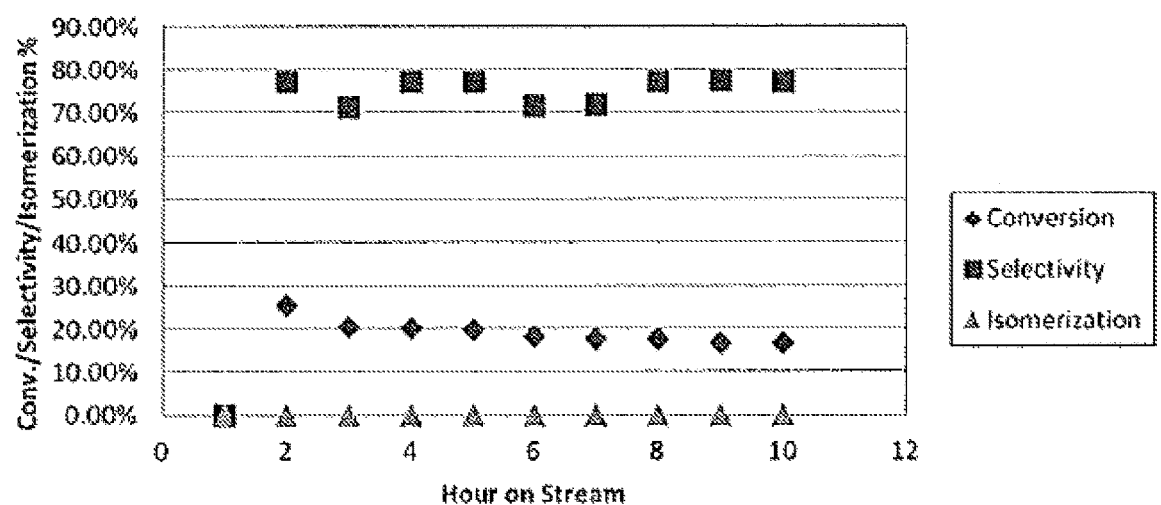
FIG. 19 presents various results from the experiments described in Example 17.

In another series, dichlorobenzene to dichlorophenol conversion at 395° C. was observed over an extended time-on-stream to evaluate longer-term performance of the catalyst. A total of ten hours on-stream was carried out. A steady-state conversion of 1,4-dichlorobenzene to 2,5-dichlorophenol of about 19% was observed with selectivity at about 75%. In this series, dichlorobenzene isomerization was totally suppressed. See FIG. 19.

Embodiments

For further illustration, additional non-limiting embodiments of the present disclosure are set forth below.

For example, embodiment A1 is a process for producing 2,5-dichlorophenol, the process comprising:
contacting a feed comprising 2,4-dichlorophenol with a zeolite catalyst in acid form in an isomerization zone to isomerize at least a portion of the 2,4-dichlorophenol to 2,5-dichlorophenol, wherein the zeolite catalyst has a SiO$_2$/Al$_2$O$_3$ mole ratio of no greater than about 35:1.

Embodiment A2 is the process of embodiment A1 wherein the SiO$_2$/Al$_2$O$_3$ mole ratio is no greater than about 30:1.

Embodiment A3 is the process of embodiment A1 or A2 wherein the SiO$_2$/Al$_2$O$_3$ mole ratio is from about 23:1 to about 35:1, from about 20:1 to about 30:1, or from about 23:1 to about 30:1.

Embodiment A4 is the process of any one of embodiments A1 to A3 wherein the SiO$_2$/Al$_2$O$_3$ mole ratio is about 23:1.

Embodiment A5 is the process of any one of embodiments A1 to A4 wherein the zeolite catalyst comprises a medium or large pore-size zeolite.

Embodiment A6 is the process of any one of embodiments A1 to A5 wherein the zeolite catalyst comprises a pentasil zeolite.

Embodiment A7 is the process of any one of embodiments A1 to A6 wherein the zeolite catalyst comprises a ZSM zeolite.

Embodiment A8 is the process of any one of embodiments A1 to A7 wherein the zeolite catalyst comprises a HZSM-5 zeolite.

Embodiment A9 is the process of any one of embodiments A1 to A8 wherein the zeolite catalyst comprises a HZSM-11 zeolite.

Embodiment A10 is the process of any one of embodiments A1 to A9 wherein the zeolite catalyst comprises zeolite Beta.

Embodiment A11 is the process of any one of embodiments A1 to A10 wherein the zeolite catalyst comprises a faujasite zeolite.

Embodiment A12 is the process of any one of embodiments A1 to A11 wherein the zeolite catalyst comprises zeolite Y.

Embodiment A13 is the process of any one of embodiments A1 to A12 wherein the zeolite catalyst comprises a boron-promoted zeolite or a metal-promoted zeolite selected from the group consisting of titanium-silicates, alumino-silicates, iron-silicates, and gallium-silicate.

Embodiment A14 is the process of any one of embodiments A1 to A13 wherein the zeolite catalyst comprises at least one alumino-silicate zeolite selected from the group consisting of ZSM, Beta, Y zeolites, and mixtures thereof.

Embodiment A15 is the process of any one of embodiments A1 to A14 wherein the isomerization is conducted at a catalyst temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C.

to about 350° C., from about 280° C. to about 325° C., or from about 290° C. to about 310° C.

Embodiment A16 is the process of any one of embodiments A1 to A15 wherein the selectivity of the isomerization of 2,4-dichlorophenol to 2,5-dichlorophenol is at least about 50%, at least about 60%, at least about 70%, at least about 80%, at least about 85%, at least about 90%, or at least about 95%.

Embodiment A17 is the process of any one of embodiments A1 to A15 wherein the selectivity of the isomerization of 2,4-dichlorophenol to 2,5-dichlorophenol is from about 50% to about 99%, from about 70% to about 99%, from about 70% to about 97%, from about 70% to about 95%, from about 80% to about 99%, from about 80% to about 97%, from about 80% to about 95%, from about 85% to about 97%, from about 85% to about 95%, or from about 90% to about 97%.

Embodiment A18 is the process of any one of embodiments A1 to A17 wherein the conversion of the 2,4-dichlorophenol is at least about 10%, at least about 15%, at least about 20%, or at least about 25%.

Embodiment A19 is the process of any one of embodiments A1 to A17 wherein the conversion of the 2,4-dichlorophenol is in the range of from about 10% to about 65%, from about 10% to about 60%, from about 10% to about 50%, from about 10% to about 45%, from about 15% to about 65%, from about 15% to about 60%, from about 15% to about 50%, from about 20% to about 65%, from about 20% to about 60%, from about 20% to about 50%, or from about 20% to about 40%.

Embodiment A20 is the process of any one of embodiments A1 to A19 wherein the feed comprises a feed gas comprising 2,4-dichlorophenol and the partial pressure of 2,4-dichlorophenol in the feed gas is at least about 0.05 kPa, at least about 0.5 kPa, or at least about 1 kPa.

Embodiment A21 is the process of any one of embodiments A1 to A19 wherein the feed comprises a feed gas comprising 2,4-dichlorophenol and the partial pressure of 2,4-dichlorophenol in the feed gas is from about 0.05 kPa to about 10 kPa, from about 0.5 kPa to about 10 kPa, or from about 1 kPa to about 10 kPa.

Embodiment A22 is the process of any one of embodiments A1 to A21 wherein the number of active aluminum sites on the zeolite catalyst is greater than about 500 µmol/g, greater than about 550 µmol/g, or greater than about 580 µmol/g.

Embodiment A23 is the process of any one of embodiments A1 to A21 wherein the number of active aluminum sites on the zeolite catalyst is from about 500 µmol/g to about 650 µmol/g, from about 550 µmol/g to about 650 µmol/g, from about 580 µmol/g to about 650 µmol/g, or from about 580 µmol/g to about 600 µmol/g.

Embodiment A24 is the process of any one of embodiments A1 to A23 wherein the zeolite catalyst is calcined at a temperature of at least about 450° C., at least about 500° C., at least about 510° C., at least about 520° C., at least about 530° C., at least about 540° C., or at least about 550° C.

Embodiment A25 is the process of any one of embodiments A1 to A23 wherein the zeolite catalyst is calcined at a temperature in the range of from about 500° C. to about 1000° C., from about 500° C. to about 900° C., from about 500° C. to about 800° C., from about 500° C. to about 700° C., from about 520° C. to about 600° C., from about 530° C. to 580° C., or from about 540° C. to 560° C.

Embodiment A26 is the process of any one of embodiments A1 to A25 wherein the molar yield of 3,4-dichlorophenol is less than about 5%, less than about 3%, less than about 1%, or between about 1% and about 5%.

Embodiment A27 is the process of any one of embodiment A1 to A26 wherein the sum of molar yields of 2-chlorophenol, 3-chlorophenol, and 4-chlorophenol is less than about 5%, less than about 3%, less than about 1%, or between about 1% and about 5%.

Embodiment A28 is the process of any one of embodiments A1 to A27 further comprising regenerating the zeolite catalyst.

Embodiment A29 is the process of any one of embodiments A1 to A28 wherein the feed comprising 2,4-dichlorophenol is supplied to the isomerization zone as a liquid.

Embodiment A30 is the process of any one of embodiments A1 to A28 wherein the feed comprising 2,4-dichlorophenol is supplied to the isomerization zone as a gas.

Embodiment A31 is the process of any one of embodiments A1 to A30 wherein the isomerization zone comprises a fixed-bed comprising the zeolite catalyst.

Embodiment A32 is the process of any one of embodiments A1 to A31 wherein the mass of catalyst divided by the mass flow rate of 2,4-dichlorophenol in the feed to the isomerization zone is at least about 1000 g·s/g, at least about 5000 g·s/g, at least about 10000 g·s/g, at least about 20000 g·s/g, at least about 50000 g·s/g, or at least about 70000 g·s/g.

Embodiment A33 is the process of any one of embodiments A1 to A31 wherein the mass of catalyst divided by the mass flow rate of 2,4-dichlorophenol in the feed to the isomerization zone is from about 1000 g·s/g to about 150000 g·s/g, from about 5000 g·s/g to about 150000 g·s/g, from about 10000 g·s/g to about 150000 g·s/g, from about 20000 g·s/g to about 150000 g·s/g, from about 20000 g·s/g to about 120000 g·s/g, from about 20000 g·s/g to about 100000 g·s/g, or from about 20000 g·s/g to about 70000 g·s/g.

Embodiment A34 is the process of any one of embodiments A1 to A33 further comprising feeding water to the isomerization zone.

Embodiment A35 is the process of embodiment A34 wherein the water is fed continuously to the isomerization zone.

Embodiment A36 is the process of embodiment A34 wherein the water is fed intermittently to the isomerization zone.

Embodiment A37 is the process of any one of embodiments A34 to A36 wherein the weight ratio of catalyst to water per hour is at least about 150:1, at least about 200:1, at least about 300:1, or at least about 400:1.

Embodiment A38 is the process of any one of embodiments A34 to A36 wherein the weight ratio of catalyst to water per hour is from about 150:1 to about 500:1, from about 150:1 to about 400:1, from about 200:1 to about 500:1, or from about 200:1 to about 400:1.

Embodiment A39 is process of any one of embodiments A34 to A38 wherein the weight ratio of 2,4-dichlorophenol in the feed to water per hour is at least about 5:1, at least about 10:1, at least about 15:1, or at least about 20:1.

Embodiment A40 is the process of any one of embodiments A34 to A38 wherein the weight ratio of 2,4-dichlorophenol in the feed to water per hour is from about 5:1 to about 30:1, from about 5:1 to about 25:1, from about 5:1 to about 20:1, or from about 10:1 to about 20:1.

Embodiment A41 is the process of any one of embodiments A34 to A40 wherein the water is fed to the isomerization zone as steam.

Embodiment A42 is the process of embodiment A41 wherein the steam fed to the isomerization zone is at a temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment A43 is the process of any one of embodiments A1 to A42 wherein the zeolite catalyst has a meso-macro pore volume that is at least about 0.15 cm$^3$/g, at least about 0.175 cm$^3$/g, at least about 0.2 cm$^3$/g, at least about 0.225 cm$^3$/g, or at least about 0.25 cm$^3$/g.

Embodiment A44 is the process of any one of embodiments A1 to A42 wherein the meso-macro pore volume of the zeolite catalyst is from about 0.15 cm$^3$/g to about 0.3 cm$^3$/g, from about 0.175 cm$^3$/g to about 0.3 cm$^3$/g, from about 0.2 cm$^3$/g to about 0.3 cm$^3$/g, from about 0.225 cm$^3$/g to about 0.3 cm$^3$/g, or from about 0.25 cm$^3$/g to about 0.3 cm$^3$/g.

Embodiment A45 is the process of any one of embodiments A1 to A44 further comprising feeding 3,4-dichlorophenol to the isomerization zone.

Embodiment A46 is the process of embodiment A45 wherein the mole ratio of 2,4-dichlorophenol to 3,4-dichlorophenol in the feed is at least about 10:1, at least about 15:1, at least about 20:1, at least about 30:1, or at least about 40:1.

Embodiment A47 is the process of embodiment A45 wherein the mole ratio of 2,4-dichlorophenol to 3,4-dichlorophenol in the feed is from about 10:1 to about 50:1, from about 10:1 to about 40:1, from about 10:1 to about 30:1, from about 10:1 to about 20:1, from about 15:1 to about 50:1, from about 15:1 to about 40:1, from about 15:1 to about 30:1, from about 15:1 to about 20:1, from about 20:1 to about 50:1, from about 20:1 to about 40:1, or from about 20:1 to about 30:1.

Embodiment A48 is the process of any one of embodiments A1 to A47 further comprising:
  suspending contact of the feed comprising 2,4-dichlorophenol with the zeolite catalyst; and
  contacting the zeolite catalyst with steam at a temperature from about 250° C. to about 375° C. to rejuvenate the catalyst.

Embodiment A49 is the process of embodiment A48 wherein the temperature of the steam is from about 250° C. to about 375° C., from about 270° C. to about 350° C., from about 280° C. to about 325° C., or from about 290° C. to about 310° C.

Embodiment A50 is the process of embodiment A48 or A49 wherein the process further comprises contacting of the feed stream comprising 2,4-dichlorophenol with the rejuvenated zeolite catalyst.

Embodiment A51 is the process of any one of embodiments A48 to A50 wherein the zeolite catalyst is contacted with steam after the contact of the feed comprising 2,4-dichlorophenol is suspended.

Embodiment B1 is a process for producing 2,5-dichlorophenol, the process comprising:
  contacting a feed comprising 2,4-dichlorophenol and water with a zeolite catalyst in acid form in an isomerization zone to isomerize at least a portion of the 2,4-dichlorophenol to 2,5-dichlorophenol.

Embodiment B2 is the process of embodiment B1 wherein the water is fed continuously to the isomerization zone.

Embodiment B3 is the process of embodiment B1 wherein the water is fed intermittently to the isomerization zone.

Embodiment B4 is the process of any one of embodiments B1 to B3 wherein the weight ratio of catalyst to water per hour is at least about 150:1, at least about 200:1, at least about 300:1, or at least about 400:1.

Embodiment B5 is the process of any one of embodiments B1 to B3 wherein the weight ratio of catalyst to water per hour is from about 150:1 to about 500:1, from about 150:1 to about 400:1, from about 200:1 to about 500:1, or from about 200:1 to about 400:1.

Embodiment B6 is the process of any one of embodiments B1 to B5 wherein the weight ratio of 2,4-dichlorophenol in the feed to water per hour is at least about 5:1, at least about 10:1, at least about 15:1, or at least about 20:1.

Embodiment B7 is the process of any one of embodiments B1 to B5 wherein the weight ratio of 2,4-dichlorophenol in the feed to water per hour is from about 5:1 to about 30:1, from about 5:1 to about 25:1, from about 5:1 to about 20:1, or from about 10:1 to about 20:1.

Embodiment B8 is the process of any one of embodiments B1 to B7 wherein the water is fed to the isomerization zone as steam.

Embodiment B9 is the process of embodiment B8 wherein the steam fed to the isomerization zone is at a temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment B10 is the process of any one of embodiments B1 to B9 wherein the SiO$_2$/Al$_2$O$_3$ mole ratio is no greater than about 35:1.

Embodiment B11 is the process of any one of embodiments B1 to B10 wherein the SiO$_2$/Al$_2$O$_3$ mole ratio is no greater than about 30:1.

Embodiment B12 is the process of any one of embodiments B1 to B9 wherein the SiO$_2$/Al$_2$O$_3$ mole ratio is from about 23:1 to about 35:1, from about 20:1 to about 30:1, or from about 23:1 to about 30:1.

Embodiment B13 is the process of any one of embodiment B1 to B9 wherein the SiO$_2$/Al$_2$O$_3$ mole ratio is about 23:1.

Embodiment B14 is the process of any one of embodiments B1 to B13 wherein the zeolite catalyst comprises a medium or large pore-size zeolite.

Embodiment B15 is the process of any one of embodiments B1 to B14 wherein the zeolite catalyst comprises a pentasil zeolite.

Embodiment B16 is the process of any one of embodiments B1 to B15 wherein the zeolite catalyst comprises a ZSM zeolite.

Embodiment B17 is the process of any one of embodiments B1 to B16 wherein the zeolite catalyst comprises a HZSM-5 zeolite.

Embodiment B18 is the process of any one of embodiments B1 to B17 wherein the zeolite catalyst comprises a HZSM-11 zeolite.

Embodiment B19 is the process of any one of embodiments B1 to B18 wherein the zeolite catalyst comprises zeolite Beta.

Embodiment B20 is the process of any one of embodiments B1 to B19 wherein the zeolite catalyst comprises a faujasite zeolite.

Embodiment B21 is the process of any one of embodiments B1 to B20 wherein the zeolite catalyst comprises zeolite Y.

Embodiment B22 is the process of any one of embodiments B1 to B21 wherein the zeolite catalyst comprises a boron-promoted zeolite or a metal-promoted zeolite selected from the group consisting of titanium-silicates, alumino-silicates, iron-silicates, and gallium-silicate.

Embodiment B23 is the process of any one of embodiments B1 to B22 wherein the zeolite catalyst comprises at least one alumino-silicate zeolite selected from the group consisting of ZSM, Beta, Y zeolites, and mixtures thereof.

Embodiment B24 is the process of any one of embodiments B1 to B23 wherein the isomerization is conducted at a catalyst temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment B25 is the process of any one of embodiments B1 to B24 wherein the selectivity of the isomerization of 2,4-dichlorophenol to 2,5-dichlorophenol is at least about 50%, at least about 60%, at least about 70%, at least about 80%, at least about 85%, at least about 90%, or at least about 95%.

Embodiment B26 is the process of any one of embodiments B1 to B24 wherein the selectivity of the isomerization of 2,4-dichlorophenol to 2,5-dichlorophenol is from about 50% to about 99%, from about 70% to about 99%, from about 70% to about 97%, from about 70% to about 95%, from about 80% to about 99%, from about 80% to about 97%, from about 80% to about 95%, from about 85% to about 97%, from about 85% to about 95%, or from about 90% to about 97%.

Embodiment B27 is the process of any one of embodiments B1 to B26 wherein the conversion of the 2,4-dichlorophenol is at least about 10%, at least about 15%, at least about 20%, or at least about 25%.

Embodiment B28 is the process of any one of embodiments B1 to B26 wherein the conversion of the 2,4-dichlorophenol is in the range of from about 10% to about 65%, from about 10% to about 60%, from about 10% to about 50%, from about 10% to about 45%, from about 15% to about 65%, from about 15% to about 60%, from about 15% to about 50%, from about 20% to about 65%, from about 20% to about 60%, from about 20% to about 50%, or from about 20% to about 40%.

Embodiment B29 is the process of any one of embodiments B1 to B28 wherein the feed comprises a feed gas comprising 2,4-dichlorophenol and the partial pressure of 2,4-dichlorophenol in the feed gas is at least about 0.05 kPa, at least about 0.5 kPa, or at least about 1 kPa.

Embodiment B30 is the process of any one of embodiments B1 to B28 wherein the feed comprises a feed gas comprising 2,4-dichlorophenol and the partial pressure of 2,4-dichlorophenol in the feed gas is from about 0.05 kPa to about 10 kPa, from about 0.5 kPa to about 10 kPa, or from about 1 kPa to about 10 kPa.

Embodiment B31 is the process of any one of embodiments B1 to B30 wherein the number of active aluminum sites on the zeolite catalyst is greater than about 500 μmol/g, greater than about 550 μmol/g, or greater than about 580 μmol/g.

Embodiment B32 is the process of any one of embodiments B1 to B30 wherein the number of active aluminum sites on the zeolite catalyst is from about 500 μmol/g to about 650 μmol/g, from about 550 μmol/g to about 650 μmol/g, from about 580 μmol/g to about 650 μmol/g, or from about 580 μmol/g to about 600 μmol/g.

Embodiment B33 is the process of any one of embodiments B1 to B32 wherein the zeolite catalyst is calcined at a temperature of at least about 450° C., at least about 500° C., at least about 510° C., at least about 520° C., at least about 530° C., at least about 540° C., or at least about 550° C.

Embodiment B34 is the process of any one of embodiments B1 to B32 wherein the zeolite catalyst is calcined at a temperature in the range of from about 500° C. to about 1000° C., from about 500° C. to about 900° C., from about 500° C. to about 800° C., from about 500° C. to about 700° C., from about 520° C. to about 600° C., from about 530° C. to 580° C., or from about 540° C. to 560° C.

Embodiment B35 is the process of any one of embodiments B1 to B34 wherein the molar yield of 3,4-dichlorophenol is less than about 5%, less than about 3%, less than about 1%, or between about 1% and about 5%.

Embodiment B36 is the process of any one of embodiments B1 to B35 wherein the sum of molar yields of 2-chlorophenol, 3-chlorophenol, and 4-chlorophenol is less than about 5%, less than about 3%, less than about 1%, or between about 1% and about 5%.

Embodiment B37 is the process of any one of embodiments B1 to B36 further comprising regenerating the zeolite catalyst.

Embodiment B38 is the process of any one of embodiment B1 to B37 wherein the feed comprising 2,4-dichlorophenol is supplied to the isomerization zone as a liquid.

Embodiment B39 is the process of any one of embodiments B1 to B37 wherein the feed comprising 2,4-dichlorophenol is supplied to the isomerization zone as a gas.

Embodiment B40 is the process of any one of embodiments B1 to B39 wherein the isomerization zone comprises a fixed-bed comprising the zeolite catalyst.

Embodiment B41 is the process of any one of embodiments B1 to B40 wherein the mass of catalyst divided by the mass flow rate of 2,4-dichlorophenol in the feed to the isomerization zone is at least about 1000 g·s/g, at least about 5000 g·s/g, at least about 10000 g·s/g, at least about 20000 g·s/g, at least about 50000 g·s/g, or at least about 70000 g·s/g.

Embodiment B42 is the process of any one of embodiments B1 to B40 wherein the mass of catalyst divided by the mass flow rate of 2,4-dichlorophenol in the feed to the isomerization zone is from about 1000 g·s/g to about 150000 g·s/g, from about 5000 g·s/g to about 150000 g·s/g, from about 10000 g·s/g to about 150000 g·s/g, from about 20000 g·s/g to about 150000 g·s/g, from about 20000 g·s/g to about 120000 g·s/g, from about 20000 g·s/g to about 100000 g·s/g, or from about 20000 g·s/g to about 70000 g·s/g.

Embodiment B43 is the process of any one of embodiments B1 to B42 wherein the zeolite catalyst has a meso-macro pore volume that is at least about 0.15 cm$^3$/g, at least about 0.175 cm$^3$/g, at least about 0.2 cm$^3$/g, at least about 0.225 cm$^3$/g, or at least about 0.25 cm$^3$/g.

Embodiment B44 is the process of any one of embodiments B1 to B42 wherein the meso-macro pore volume of the zeolite catalyst is from about 0.15 cm$^3$/g to about 0.3 cm$^3$/g, from about 0.175 cm$^3$/g to about 0.3 cm$^3$/g, from about 0.2 cm$^3$/g to about 0.3 cm$^3$/g, from about 0.225 cm$^3$/g to about 0.3 cm$^3$/g, or from about 0.25 cm$^3$/g to about 0.3 cm$^3$/g.

Embodiment B45 is the process of any one of embodiments B1 to B44 further comprising feeding 3,4-dichlorophenol to the isomerization zone.

Embodiment B46 is the process of embodiment B45 wherein the mole ratio of 2,4-dichlorophenol to 3,4-dichlorophenol in the feed is at least about 10:1, at least about 15:1, at least about 20:1, at least about 30:1, or at least about 40:1.

Embodiment B47 is the process of embodiment B46 wherein the mole ratio of 2,4-dichlorophenol to 3,4-dichlorophenol in the feed is from about 10:1 to about 50:1, from about 10:1 to about 40:1, from about 10:1 to about 30:1, from about 10:1 to about 20:1, from about 15:1 to about 50:1, from about 15:1 to about 40:1, from about 15:1 to about 30:1, from about 15:1 to about 20:1, from about 20:1 to about 50:1, from about 20:1 to about 40:1, or from about 20:1 to about 30:1.

Embodiment B48 it the process of any one of embodiments B1 to B47 further comprising:
  suspending contact of the feed comprising 2,4-dichlorophenol with the zeolite catalyst; and
  contacting the zeolite catalyst with steam at a temperature from about 250° C. to about 375° C. to rejuvenate the catalyst.

Embodiment B49 is the process of embodiment B48 wherein the temperature of the steam is from about 250° C. to about 375° C., from about 270° C. to about 350° C., from about 280° C. to about 325° C., or from about 290° C. to about 310° C.

Embodiment B50 is the process of embodiment B48 or B49 wherein the process further comprises contacting of the feed stream comprising 2,4-dichlorophenol with the rejuvenated zeolite catalyst.

Embodiment B51 is the process of any one of embodiments B48 to B50 wherein the zeolite catalyst is contacted with steam after the contact of the feed comprising 2,4-dichlorophenol is suspended.

Embodiment B52 is the process of any one of embodiments B1 to B51 wherein the zeolite catalyst comprises a desilicated zeolite catalyst.

Embodiment B53 is the process of embodiment B52 wherein the desilicated zeolite catalyst has a meso-macro pore volume (attributable to pores that have diameters greater than 20 Å up to 2500 Å) that is at least about 50%, at least about 75%, at least about 100%, at least about 125%, at least about 150%, at least about 175%, at least about 200%, at least about 225%, at least about 250%, at least about 275%, or at least about 300% greater than the meso-macro pore volume of the initial zeolite catalyst before desilication.

Embodiment B54 is the process of embodiment B52 wherein the meso-macro pore volume (attributable to pores that have diameters greater than 20 Å up to 2500 Å) of the desilicated zeolite catalyst is from about 50% to about 500%, from about 50% to about 400%, from about 50% to about 300%, from about 100% to about 500%, from about 100% to 400%, from about 100% to about 300%, from about 200% to about 500%, from about 200% to about 400%, or from about 200% to about 300% greater than the meso-macro pore volume of the initial zeolite catalyst before desilication.

Embodiment B55 is the process of any one of embodiments B52 to B54 wherein the desilicated zeolite catalyst has a SiO$_2$/Al$_2$O$_3$ mole ratio of no greater than about 80:1, no greater than about 60:1, or no greater than about 55:1.

Embodiment B56 is the process of any one of embodiments B52 to B54 wherein the desilicated zeolite catalyst has a SiO$_2$/Al$_2$O$_3$ mole ratio of from about 23:1 to about 80:1; from about 23:1 to about 60:1; or from about 23:1 to about 55:1.

Embodiment B57 is the process of any one of embodiments B52 to B54 wherein the desilicated zeolite catalyst has a SiO$_2$/Al$_2$O$_3$ mole ratio of no greater than about 55:1 and a meso-macro pore volume that is at least about 0.15 cm$^3$/g, at least about 0.175 cm$^3$/g, at least about 0.2 cm$^3$/g, at least about 0.225 cm$^3$/g, or at least about 0.25 cm$^3$/g.

Embodiment B58 is the process of embodiment B57 wherein the meso-macro pore volume of the desilicated zeolite catalyst is from about 0.15 cm$^3$/g to about 0.3 cm$^3$/g, from about 0.175 cm$^3$/g to about 0.3 cm$^3$/g, from about 0.2 cm$^3$/g to about 0.3 cm$^3$/g, from about 0.225 cm$^3$/g to about 0.3 cm$^3$/g, or from about 0.25 cm$^3$/g to about 0.3 cm$^3$/g.

Embodiment C1 is a process for producing 2,5-dichlorophenol, the process comprising:
  contacting a feed comprising 2,4-dichlorophenol with a desilicated zeolite catalyst in acid form in an isomerization zone to isomerize at least a portion of the 2,4-dichlorophenol to 2,5-dichlorophenol, wherein the desilicated zeolite catalyst has a meso-macro pore volume (attributable to pores that have diameters greater than 20 Å up to 2500 Å) that is at least about 50%, at least about 75%, at least about 100%, at least about 125%, at least about 150%, at least about 175%, at least about 200%, at least about 225%, at least about 250%, at least about 275%, or at least about 300% greater than the meso-macro pore volume of the initial zeolite catalyst before desilication.

Embodiment C2 is the process of embodiment C1 wherein the meso-macro pore volume (attributable to pores that have diameters greater than 20 Å up to 2500 Å) of the desilicated zeolite catalyst is from about 50% to about 500%, from about 50% to about 400%, from about 50% to about 300%, from about 100% to about 500%, from about 100% to 400%, from about 100% to about 300%, from about 200% to about 500%, from about 200% to about 400%, or from about 200% to about 300% greater than the meso-macro pore volume of the initial zeolite catalyst before desilication.

Embodiment C3 is the process of embodiment C1 or C2 wherein the desilicated zeolite catalyst has a SiO$_2$/Al$_2$O$_3$ mole ratio of no greater than about 80:1, no greater than about 60:1, or no greater than about 55:1.

Embodiment C4 is the process of embodiment C1 or C2 wherein the desilicated zeolite catalyst has a SiO$_2$/Al$_2$O$_3$ mole ratio of from about 23:1 to about 80:1; from about 23:1 to about 60:1; or from about 23:1 to about 55:1.

Embodiment C5 is the process of embodiment C1 or C2 wherein the desilicated zeolite catalyst has a $SiO_2/Al_2O_3$ mole ratio of no greater than about 55:1 and a meso-macro pore volume that is at least about 0.15 cm³/g, at least about 0.175 cm³/g, at least about 0.2 cm³/g, at least about 0.225 cm³/g, or at least about 0.25 cm³/g.

Embodiment C6 is the process of embodiment C5 wherein the meso-macro pore volume of the desilicated zeolite catalyst is from about 0.15 cm³/g to about 0.3 cm³/g, from about 0.175 cm³/g to about 0.3 cm³/g, from about 0.2 cm³/g to about 0.3 cm³/g, from about 0.225 cm³/g to about 0.3 cm³/g, or from about 0.25 cm³/g to about 0.3 cm³/g.

Embodiment C7 is a process for producing 2,5-dichlorophenol, the process comprising:
contacting a feed comprising 2,4-dichlorophenol with a zeolite catalyst in acid form in an isomerization zone to isomerize at least a portion of the 2,4-dichlorophenol to 2,5-dichlorophenol, wherein the zeolite catalyst has a meso-macro pore volume that is at least about 0.15 cm³/g, at least about 0.175 cm³/g, at least about 0.2 cm³/g, at least about 0.225 cm³/g, or at least about 0.25 cm³/g.

Embodiment C8 is the process of embodiment C7 wherein the meso-macro pore volume of the zeolite catalyst is from about 0.15 cm³/g to about 0.3 cm³/g, from about 0.175 cm³/g to about 0.3 cm³/g, from about 0.2 cm³/g to about 0.3 cm³/g, from about 0.225 cm³/g to about 0.3 cm³/g, or from about 0.25 cm³/g to about 0.3 cm³/g.

Embodiment C9 is the process of embodiment C7 or C8 wherein the zeolite catalyst has a $SiO_2/Al_2O_3$ mole ratio of no greater than about 80:1, no greater than about 60:1, or no greater than about 55:1.

Embodiment C10 is the process of embodiment C7 or C8 wherein the zeolite catalyst has a SiO2/Al2O3 mole ratio of from about 23:1 to about 80:1; from about 23:1 to about 60:1; or from about 23:1 to about 55:1.

Embodiment C11 is the process of any one of embodiments C1 to C10 wherein the water is fed continuously to the isomerization zone.

Embodiment C12 is the process of any one of embodiments C1 to C10 wherein the water is fed intermittently to the isomerization zone.

Embodiment C13 is the process of any one of embodiments C1 to C12 wherein the weight ratio of catalyst to water per hour is at least about 150:1, at least about 200:1, at least about 300:1, or at least about 400:1.

Embodiment C14 is the process of any one of embodiments C1 to C12 wherein the weight ratio of catalyst to water per hour is from about 150:1 to about 500:1, from about 150:1 to about 400:1, from about 200:1 to about 500:1, or from about 200:1 to about 400:1.

Embodiment C15 is the process of any one of embodiments C1 to C14 wherein the zeolite catalyst comprises a pentasil zeolite.

Embodiment C16 is the process of any one of embodiments C1 to C15 wherein the zeolite catalyst comprises a ZSM zeolite.

Embodiment C17 is the process of any one of embodiments C1 to C16 wherein the zeolite catalyst comprises a HZSM-5 zeolite.

Embodiment C18 is the process of any one of embodiments C1 to C17 wherein the zeolite catalyst comprises a HZSM-11 zeolite.

Embodiment C19 is the process of any one of embodiments C1 to C18 wherein the zeolite catalyst comprises zeolite Beta.

Embodiment C20 is the process of any one of embodiments C1 to C19 wherein the zeolite catalyst comprises a faujasite zeolite.

Embodiment C21 is the process of any one of embodiments C1 to C20 wherein the zeolite catalyst comprises zeolite Y.

Embodiment C22 is the process of any one of embodiments C1 to C21 wherein the zeolite catalyst comprises a boron-promoted zeolite or a metal-promoted zeolite selected from the group consisting of titanium-silicates, alumino-silicates, iron-silicates, and gallium-silicate.

Embodiment C23 is the process of any one of embodiments C1 to C22 wherein the zeolite catalyst comprises at least one alumino-silicate zeolite selected from the group consisting of ZSM, Beta, Y zeolites, and mixtures thereof.

Embodiment C24 is the process of any one of embodiments C1 to C23 wherein the isomerization is conducted at a catalyst temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment C25 is the process of any one of embodiments C1 to C24 wherein the selectivity of the isomerization of 2,4-dichlorophenol to 2,5-dichlorophenol is at least about 50%, at least about 60%, at least about 70%, at least about 80%, at least about 85%, at least about 90%, or at least about 95%.

Embodiment C26 is the process of any one of embodiments C1 to C24 wherein the selectivity of the isomerization of 2,4-dichlorophenol to 2,5-dichlorophenol is from about 50% to about 99%, from about 70% to about 99%, from about 70% to about 97%, from about 70% to about 95%, from about 80% to about 99%, from about 80% to about 97%, from about 80% to about 95%, from about 85% to about 97%, from about 85% to about 95%, or from about 90% to about 97%.

Embodiment C27 is the process of any one of embodiments C1 to C26 wherein the conversion of the 2,4-dichlorophenol is at least about 10%, at least about 15%, at least about 20%, or at least about 25%.

Embodiment C28 is the process of any one of embodiments C1 to C26 wherein the conversion of the 2,4-dichlorophenol is in the range of from about 10% to about 65%, from about 10% to about 60%, from about 10% to about 50%, from about 10% to about 45%, from about 15% to about 65%, from about 15% to about 60%, from about 15% to about 50%, from about 20% to about 65%, from about 20% to about 60%, from about 20% to about 50%, or from about 20% to about 40%.

Embodiment C29 is the process of any one of embodiments C1 to C28 wherein the feed comprises a feed gas comprising 2,4-dichlorophenol and the partial pressure of 2,4-dichlorophenol in the feed gas is at least about 0.05 kPa, at least about 0.5 kPa, or at least about 1 kPa.

Embodiment C30 is the process of any one of embodiments C1 to C28 wherein the feed comprises a feed gas comprising 2,4-dichlorophenol and the partial pressure of 2,4-dichlorophenol in the feed gas is from about 0.05 kPa to about 10 kPa, from about 0.5 kPa to about 10 kPa, or from about 1 kPa to about 10 kPa.

Embodiment C31 is the process of any one of embodiments C1 to C30 wherein the number of active aluminum sites on the zeolite catalyst is greater than about 500 μmol/g, greater than about 550 μmol/g, or greater than about 580 μmol/g.

Embodiment C32 is the process of any one of embodiments C1 to C30 wherein the number of active aluminum sites on the zeolite catalyst is from about 500 μmol/g to about 650 μmol/g, from about 550 μmol/g to about 650 μmol/g, from about 580 μmol/g to about 650 μmol/g, or from about 580 μmol/g to about 600 μmol/g.

Embodiment C33 is the process of any one of embodiments C1 to C32 wherein the zeolite catalyst is calcined at a temperature of at least about 450° C., at least about 500° C., at least about 510° C., at least about 520° C., at least about 530° C., at least about 540° C., or at least about 550° C.

Embodiment C34 is the process of any one of embodiments C1 to C32 wherein the zeolite catalyst is calcined at a temperature in the range of from about 500° C. to about 1000° C., from about 500° C. to about 900° C., from about 500° C. to about 800° C., from about 500° C. to about 700° C., from about 520° C. to about 600° C., from about 530° C. to 580° C., or from about 540° C. to 560° C.

Embodiment C35 is the process of any one of embodiments C1 to C34 wherein the molar yield of 3,4-dichlorophenol is less than about 5%, less than about 3%, less than about 1%, or between about 1% and about 5%.

Embodiment C36 is the process of any one of embodiments C1 to C35 wherein the sum of molar yields of 2-chlorophenol, 3-chlorophenol, and 4-chlorophenol is less than about 5%, less than about 3%, less than about 1%, or between about 1% and about 5%.

Embodiment C37 is the process of any one of embodiments C1 to C36 further comprising regenerating the zeolite catalyst.

Embodiment C38 is the process of any one of embodiments C1 to C37 wherein the feed comprising 2,4-dichlorophenol is supplied to the isomerization zone as a liquid.

Embodiment C39 is the process of any one of embodiments C1 to C37 wherein the feed comprising 2,4-dichlorophenol is supplied to the isomerization zone as a gas.

Embodiment C40 is the process of any one of embodiments C1 to C39 wherein the isomerization zone comprises a fixed-bed comprising the zeolite catalyst.

Embodiment C41 is the process of any one of embodiments C1 to C40 wherein the mass of catalyst divided by the mass flow rate of 2,4-dichlorophenol in the feed to the isomerization zone is at least about 1000 g·s/g, at least about 5000 g·s/g, at least about 10000 g·s/g, at least about 20000 g·s/g, at least about 50000 g·s/g, or at least about 70000 g·s/g.

Embodiment C42 is the process of any one of embodiments C1 to C40 wherein the mass of catalyst divided by the mass flow rate of 2,4-dichlorophenol in the feed to the isomerization zone is from about 1000 g·s/g to about 150000 g·s/g, from about 5000 g·s/g to about 150000 g·s/g, from about 10000 g·s/g to about 150000 g·s/g, from about 20000 g·s/g to about 150000 g·s/g, from about 20000 g·s/g to about 120000 g·s/g, from about 20000 g·s/g to about 100000 g·s/g, or from about 20000 g·s/g to about 70000 g·s/g.

Embodiment C43 is the process of any one of embodiments C1 to C42 wherein the zeolite catalyst has a meso-macro pore volume that is from about 0.15 cm³/g to about 0.3 cm³/g.

Embodiment C44 is the process of any one of embodiments C1 to C42 wherein the meso-macro pore volume of the zeolite catalyst is from about 0.2 cm³/g to about 0.3 cm³/g.

Embodiment C45 is the process of any one of embodiments C1 to C44 further comprising feeding 3,4-dichlorophenol to the isomerization zone.

Embodiment C46 is the process of embodiment C45 wherein the mole ratio of 2,4-dichlorophenol to 3,4-dichlorophenol in the feed is at least about 10:1, at least about 15:1, at least about 20:1, at least about 30:1, or at least about 40:1.

Embodiment C47 is the process of embodiment C46 wherein the mole ratio of 2,4-dichlorophenol to 3,4-dichlorophenol in the feed is from about 10:1 to about 50:1, from about 10:1 to about 40:1, from about 10:1 to about 30:1, from about 10:1 to about 20:1, from about 15:1 to about 50:1, from about 15:1 to about 40:1, from about 15:1 to about 30:1, from about 15:1 to about 20:1, from about 20:1 to about 50:1, from about 20:1 to about 40:1, or from about 20:1 to about 30:1.

Embodiment C48 is the process of any one of embodiments C1 to C47 further comprising:
  suspending contact of the feed comprising 2,4-dichlorophenol with the zeolite catalyst; and
  contacting the zeolite catalyst with steam at a temperature from about 250° C. to about 375° C. to rejuvenate the catalyst.

Embodiment C49 is the process of embodiment C48 wherein the temperature of the steam is from about 250° C. to about 375° C., from about 270° C. to about 350° C., from about 280° C. to about 325° C., or from about 290° C. to about 310° C.

Embodiment C50 is the process of embodiment C48 or C49 wherein the process further comprises contacting of the feed stream comprising 2,4-dichlorophenol with the rejuvenated zeolite catalyst.

Embodiment C51 is the process of any one of embodiments C48 to C50 wherein the zeolite catalyst is contacted with steam after the contact of the feed comprising 2,4-dichlorophenol is suspended.

Embodiment C52 is the process of any one of embodiments C1 to C51 further comprising feeding water to the isomerization zone.

Embodiment C53 is the process of embodiment C52 wherein the weight ratio of 2,4-dichlorophenol in the feed to water per hour is at least about 5:1, at least about 10:1, at least about 15:1, or at least about 20:1.

Embodiment C54 is the process of embodiment C52 wherein the weight ratio of 2,4-dichlorophenol in the feed to water per hour is from about 5:1 to about 30:1, from about 5:1 to about 25:1, from about 5:1 to about 20:1, or from about 10:1 to about 20:1.

Embodiment C55 is the process of any one of embodiments C52 to C54 wherein the water is fed to the isomerization zone as steam.

Embodiment C56 is the process of embodiment C55 wherein the steam fed to the isomerization zone is at a temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment D1 is a process for producing 2,5-dichlorophenol, the process comprising:
  contacting a feed comprising 2,4-dichlorophenol and 3,4-dichlorophenol with a zeolite catalyst in acid form in an isomerization zone to isomerize at least a portion of the 2,4-dichlorophenol to 2,5-dichlorophenol.

Embodiment D2 is the process of embodiment D1 wherein the $SiO_2/Al_2O_3$ mole ratio is no greater than about 35:1 or no greater than about 30:1.

Embodiment D3 is the process of embodiment D1 or D2 wherein the $SiO_2/Al_2O_3$ mole ratio is from about 23:1 to about 35:1, from about 20:1 to about 30:1, or from about 23:1 to about 30:1.

Embodiment D4 is the process of any one of embodiments D1 to D3 wherein the $SiO_2/Al_2O_3$ mole ratio is about 23:1.

Embodiment D5 is the process of any one of embodiments D1 to D4 wherein the zeolite catalyst comprises a medium or large pore-size zeolite.

Embodiment D6 is the process of any one of embodiments D1 to D5 wherein the zeolite catalyst comprises a pentasil zeolite.

Embodiment D7 is the process of any one of embodiments D1 to D6 wherein the zeolite catalyst comprises a ZSM zeolite.

Embodiment D8 is the process of any one of embodiments D1 to D7 wherein the zeolite catalyst comprises a HZSM-5 zeolite.

Embodiment D9 is the process of any one of embodiments D1 to D8 wherein the zeolite catalyst comprises a HZSM-11 zeolite.

Embodiment D10 is the process of any one of embodiments D1 to D9 wherein the zeolite catalyst comprises zeolite Beta.

Embodiment D11 is the process of any one of embodiments D1 to D10 wherein the zeolite catalyst comprises a faujasite zeolite.

Embodiment D12 is the process of any one of embodiments D1 to D11 wherein the zeolite catalyst comprises zeolite Y.

Embodiment D13 is the process of any one of embodiments D1 to D12 wherein the zeolite catalyst comprises a boron-promoted zeolite or a metal-promoted zeolite selected from the group consisting of titanium-silicates, alumino-silicates, iron-silicates, and gallium-silicate.

Embodiment D14 is the process of any one of embodiments D1 to D13 wherein the zeolite catalyst comprises at least one alumino-silicate zeolite selected from the group consisting of ZSM, Beta, Y zeolites, and mixtures thereof.

Embodiment D15 is the process of any one of embodiments D1 to D14 wherein the isomerization is conducted at a catalyst temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment D16 is the process of any one of embodiments D1 to D15 wherein the selectivity of the isomerization of 2,4-dichlorophenol to 2,5-dichlorophenol is at least about 50%, at least about 60%, at least about 70%, at least about 80%, at least about 85%, at least about 90%, or at least about 95%.

Embodiment D17 is the process of any one of embodiments D1 to D15 wherein the selectivity of the isomerization of 2,4-dichlorophenol to 2,5-dichlorophenol is from about 50% to about 99%, from about 70% to about 99%, from about 70% to about 97%, from about 70% to about 95%, from about 80% to about 99%, from about 80% to about 97%, from about 80% to about 95%, from about 85% to about 97%, from about 85% to about 95%, or from about 90% to about 97%.

Embodiment D18 is the process of any one of embodiments D1 to D17 wherein the conversion of the 2,4-dichlorophenol is at least about 10%, at least about 15%, at least about 20%, or at least about 25%.

Embodiment D19 is the process of any one of embodiments D1 to D17 wherein the conversion of the 2,4-dichlorophenol is in the range of from about 10% to about 65%, from about 10% to about 60%, from about 10% to about 50%, from about 10% to about 45%, from about 15% to about 65%, from about 15% to about 60%, from about 15% to about 50%, from about 20% to about 65%, from about 20% to about 60%, from about 20% to about 50%, or from about 20% to about 40%.

Embodiment D20 is the process of any one of embodiments D1 to D19 wherein the feed comprises a feed gas comprising 2,4-dichlorophenol and the partial pressure of 2,4-dichlorophenol in the feed gas is at least about 0.05 kPa, at least about 0.5 kPa, or at least about 1 kPa.

Embodiment D21 is the process of any one of embodiments D1 to D19 wherein the feed comprises a feed gas comprising 2,4-dichlorophenol and the partial pressure of 2,4-dichlorophenol in the feed gas is from about 0.05 kPa to about 10 kPa, from about 0.5 kPa to about 10 kPa, or from about 1 kPa to about 10 kPa.

Embodiment D22 is the process of any one of embodiments D1 to D21 wherein the number of active aluminum sites on the zeolite catalyst is greater than about 500 µmol/g, greater than about 550 µmol/g, or greater than about 580 µmol/g.

Embodiment D23 is the process of any one of embodiments D1 to D21 wherein the number of active aluminum sites on the zeolite catalyst is from about 500 µmol/g to about 650 µmol/g, from about 550 µmol/g to about 650 µmol/g, from about 580 µmol/g to about 650 µmol/g, or from about 580 µmol/g to about 600 µmol/g.

Embodiment D24 is the process of any one of embodiments D1 to D23 wherein the zeolite catalyst is calcined at a temperature of at least about 450° C., at least about 500° C., at least about 510° C., at least about 520° C., at least about 530° C., at least about 540° C., or at least about 550° C.

Embodiment D25 is the process of any one of embodiments D1 to D23 wherein the zeolite catalyst is calcined at a temperature in the range of from about 500° C. to about 1000° C., from about 500° C. to about 900° C., from about 500° C. to about 800° C., from about 500° C. to about 700°

C., from about 520° C. to about 600° C., from about 530° C. to 580° C., or from about 540° C. to 560° C.

Embodiment D26 is the process of any one of embodiments D1 to D25 wherein the molar yield of 3,4-dichlorophenol is less than about 5%, less than about 3%, less than about 1%, or between about 1% and about 5%.

Embodiment D27 is the process of any one of embodiments D1 to D26 wherein the sum of molar yields of 2-chlorophenol, 3-chlorophenol, and 4-chlorophenol is less than about 5%, less than about 3%, less than about 1%, or between about 1% and about 5%.

Embodiment D28 is the process of any one of embodiments D1 to D27 further comprising regenerating the zeolite catalyst.

Embodiment D29 is the process of any one of embodiments D1 to D28 wherein the feed comprising 2,4-dichlorophenol is supplied to the isomerization zone as a liquid.

Embodiment D30 is the process of any one of embodiments D1 to D28 wherein the feed comprising 2,4-dichlorophenol is supplied to the isomerization zone as a gas.

Embodiment D31 is the process of any one of embodiments D1 to D30 wherein the isomerization zone comprises a fixed-bed comprising the zeolite catalyst.

Embodiment D32 is the process of any one of embodiments D1 to D31 wherein the mass of catalyst divided by the mass flow rate of 2,4-dichlorophenol in the feed to the isomerization zone is at least about 1000 g·s/g, at least about 50000 g·s/g, at least about 10000 g·s/g, at least about 20000 g·s/g, at least about 50000 g·s/g, or at least about 70000 g·s/g.

Embodiment D33 is the process of any one of embodiments D1 to D31 wherein the mass of catalyst divided by the mass flow rate of 2,4-dichlorophenol in the feed to the isomerization zone is from about 1000 g·s/g to about 150000 g·s/g, from about 5000 g·s/g to about 150000 g·s/g, from about 10000 g·s/g to about 150000 g·s/g, from about 20000 g·s/g to about 150000 g·s/g, from about 20000 g·s/g to about 120000 g·s/g, from about 20000 g·s/g to about 100000 g·s/g, or from about 20000 g·s/g to about 70000 g·s/g.

Embodiment D34 is the process of any one of embodiments D1 to D33 further comprising feeding water to the isomerization zone.

Embodiment D35 is the process of embodiment D34 wherein the water is fed continuously to the isomerization zone.

Embodiment D36 is the process of embodiment D34 wherein the water is fed intermittently to the isomerization zone.

Embodiment D37 is the process of any one of embodiments D34 to D36 wherein the weight ratio of catalyst to water per hour is at least about 150:1, at least about 200:1, at least about 300:1, or at least about 400:1.

Embodiment D38 is the process of any one of embodiments D34 to D36 wherein the weight ratio of catalyst to water per hour is from about 150:1 to about 500:1, from about 150:1 to about 400:1, from about 200:1 to about 500:1, or from about 200:1 to about 400:1.

Embodiment D39 is the process of any one of embodiments D34 to D38 wherein the weight ratio of 2,4-dichlorophenol in the feed to water per hour is at least about 5:1, at least about 10:1, at least about 15:1, or at least about 20:1.

Embodiment D40 is the process of any one of embodiments D34 to D38 wherein the weight ratio of 2,4-dichlorophenol in the feed to water per hour is from about 5:1 to about 30:1, from about 5:1 to about 25:1, from about 5:1 to about 20:1, or from about 10:1 to about 20:1.

Embodiment D41 is the process of any one of embodiments D34 to D40 wherein the water is fed to the isomerization zone as steam.

Embodiment D42 is the process of embodiment D41 wherein the steam fed to the isomerization zone is at a temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment D43 is the process of any one of embodiments D1 to D42 wherein the zeolite catalyst has a meso-macro pore volume that is at least about 0.15 cm$^3$/g, at least about 0.175 cm$^3$/g, at least about 0.2 cm$^3$/g, at least about 0.225 cm$^3$/g, or at least about 0.25 cm$^3$/g.

Embodiment D44 is the process of any one of embodiments D1 to D42 wherein the meso-macro pore volume of the zeolite catalyst is from about 0.15 cm$^3$/g to about 0.3 cm$^3$/g, from about 0.175 cm$^3$/g to about 0.3 cm$^3$/g, from about 0.2 cm$^3$/g to about 0.3 cm$^3$/g, from about 0.225 cm$^3$/g to about 0.3 cm$^3$/g, or from about 0.25 cm$^3$/g to about 0.3 cm3/g.

Embodiment D45 is the process of any one of embodiments D1 to D44 wherein the mole ratio of 2,4-dichlorophenol to 3,4-dichlorophenol in the feed is at least about 10:1, at least about 15:1, at least about 20:1, at least about 30:1, or at least about 40:1.

Embodiment D46 is the process of any one of embodiments D1 to D44 wherein the mole ratio of 2,4-dichlorophenol to 3,4-dichlorophenol in the feed is from about 10:1 to about 50:1, from about 10:1 to about 40:1, from about 10:1 to about 30:1, from about 10:1 to about 20:1, from about 15:1 to about 50:1, from about 15:1 to about 40:1, from about 15:1 to about 30:1, from about 15:1 to about 20:1, from about 20:1 to about 50:1, from about 20:1 to about 40:1, or from about 20:1 to about 30:1.

Embodiment D47 is the process of any one of embodiments D1 to D46 further comprising:
  suspending contact of the feed comprising 2,4-dichlorophenol with the zeolite catalyst; and
  contacting the zeolite catalyst with steam at a temperature from about 250° C. to about 375° C. to rejuvenate the catalyst.

Embodiment D48 is the process of embodiment D47 wherein the temperature of the steam is from about 250° C. to about 375° C., from about 270° C. to about 350° C., from about 280° C. to about 325° C., or from about 290° C. to about 310° C.

Embodiment D49 is the process of embodiment D47 or D48 wherein the process further comprises contacting of the feed stream comprising 2,4-dichlorophenol with the rejuvenated zeolite catalyst.

Embodiment D50 is the process of any one of embodiments D47 to D49 wherein the zeolite catalyst is contacted with steam after the contact of the feed comprising 2,4-dichlorophenol is suspended.

Embodiment D51 is the process of any one of embodiments D1 to D50 wherein the zeolite catalyst comprises a desilicated zeolite catalyst.

Embodiment D52 is the process of embodiment D51 wherein the desilicated zeolite catalyst has a meso-macro pore volume (attributable to pores that have diameters greater than 20 Å up to 2500 Å) that is at least about 50%, at least about 75%, at least about 100%, at least about 125%, at least about 150%, at least about 175%, at least about 200%, at least about 225%, at least about 250%, at least about 275%, or at least about 300% greater than the meso-macro pore volume of the initial zeolite catalyst before desilication.

Embodiment D53 is the process of embodiment D51 wherein the meso-macro pore volume (attributable to pores that have diameters greater than 20 Å up to 2500 Å) of the desilicated zeolite catalyst is from about 50% to about 500%, from about 50% to about 400%, from about 50% to about 300%, from about 100% to about 500%, from about 100% to 400%, from about 100% to about 300%, from about 200% to about 500%, from about 200% to about 400%, or from about 200% to about 300% greater than the meso-macro pore volume of the initial zeolite catalyst before desilication.

Embodiment D54 is the process of any one of embodiments D51 to D53 wherein the desilicated zeolite catalyst has a $SiO_2/Al_2O_3$ mole ratio of no greater than about 80:1, no greater than about 60:1, or no greater than about 55:1.

Embodiment D55 is the process of any one of embodiments D51 to D53 wherein the desilicated zeolite catalyst has a $SiO_2/Al_2O_3$ mole ratio of from about 23:1 to about 80:1; from about 23:1 to about 60:1; or from about 23:1 to about 55:1.

Embodiment D56 is the process of any one of embodiments D51 to D53 wherein the desilicated zeolite catalyst has a $SiO_2/Al_2O_3$ mole ratio of no greater than about 55:1 and a meso-macro pore volume that is at least about 0.15 $cm^3/g$, at least about 0.175 $cm^3/g$, at least about 0.2 $cm^3/g$, at least about 0.225 $cm^3/g$, or at least about 0.25 $cm^3/g$.

Embodiment D57 is the process of embodiment D56 wherein the meso-macro pore volume of the desilicated zeolite catalyst is from about 0.15 $cm^3/g$ to about 0.3 $cm^3/g$, from about 0.175 $cm^3/g$ to about 0.3 $cm^3/g$, from about 0.2 $cm^3/g$ to about 0.3 $cm^3/g$, from about 0.225 $cm^3/g$ to about 0.3 $cm^3/g$, or from about 0.25 $cm^3/g$ to about 0.3 $cm^3/g$.

Embodiment E1 is a process for producing 2,5-dichlorophenol, the process comprising:
  contacting a feed comprising 2,4-dichlorophenol with a zeolite catalyst in acid form in an isomerization zone to isomerize at least a portion of the 2,4-dichlorophenol to 2,5-dichlorophenol;
  suspending contact of the feed comprising 2,4-dichlorophenol with the zeolite catalyst; and
  contacting the zeolite catalyst with steam at a temperature from about 250° C. to about 375° C. to rejuvenate the catalyst.

Embodiment E2 is the process of embodiment E1 wherein the $SiO_2/Al_2O_3$ mole ratio is no greater than about 35:1 or no greater than about 30:1.

Embodiment E3 is the process of embodiment E1 or E2 wherein the $SiO_2/Al_2O_3$ mole ratio is from about 23:1 to about 35:1, from about 20:1 to about 30:1, or from about 23:1 to about 30:1.

Embodiment E4 is the process of any one of embodiments E1 to E3 wherein the $SiO_2/Al_2O_3$ mole ratio is about 23:1.

Embodiment E5 is the process of any one of embodiments E1 to E4 wherein the zeolite catalyst comprises a medium or large pore-size zeolite.

Embodiment E6 is the process of any one of embodiments E1 to E5 wherein the zeolite catalyst comprises a pentasil zeolite.

Embodiment E7 is the process of any one of embodiments E1 to E6 wherein the zeolite catalyst comprises a ZSM zeolite.

Embodiment E8 is the process of any one of embodiments E1 to E7 wherein the zeolite catalyst comprises a HZSM-5 zeolite.

Embodiment E9 is the process of any one of embodiments E1 to E8 wherein the zeolite catalyst comprises a HZSM-11 zeolite.

Embodiment E10 is the process of any one of embodiments E1 to E9 wherein the zeolite catalyst comprises zeolite Beta.

Embodiment E11 is the process of any one of embodiments E1 to E10 wherein the zeolite catalyst comprises a faujasite zeolite.

Embodiment E12 is the process of any one of embodiments E1 to E11 wherein the zeolite catalyst comprises zeolite Y.

Embodiment E13 is the process of any one of embodiments E1 to E12 wherein the zeolite catalyst comprises a boron-promoted zeolite or a metal-promoted zeolite selected from the group consisting of titanium-silicates, alumino-silicates, iron-silicates, and gallium-silicate.

Embodiment E14 is the process of any one of embodiments E1 to E13 wherein the zeolite catalyst comprises at least one alumino-silicate zeolite selected from the group consisting of ZSM, Beta, Y zeolites, and mixtures thereof.

Embodiment E15 is the process of any one of embodiments E1 to E14 wherein the isomerization is conducted at a catalyst temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment E16 is the process of any one of embodiments E1 to E15 wherein the selectivity of the isomerization of 2,4-dichlorophenol to 2,5-dichlorophenol is at least about 50%, at least about 60%, at least about 70%, at least about 80%, at least about 85%, at least about 90%, or at least about 95%.

Embodiment E17 is the process of any one of embodiments E1 to E15 wherein the selectivity of the isomerization of 2,4-dichlorophenol to 2,5-dichlorophenol is from about 50% to about 99%, from about 70% to about 99%, from about 70% to about 97%, from about 70% to about 95%, from about 80% to about 99%, from about 80% to about 97%, from about 80% to about 95%, from about 85% to about 97%, from about 85% to about 95%, or from about 90% to about 97%.

Embodiment E18 is the process of any one of embodiments E1 to E17 wherein the conversion of the 2,4-dichlorophenol is at least about 10%, at least about 15%, at least about 20%, or at least about 25%.

Embodiment E19 is the process of any one of embodiments E1 to E17 wherein the conversion of the 2,4-dichlorophenol is in the range of from about 10% to about 65%, from about 10% to about 60%, from about 10% to about 50%, from about 10% to about 45%, from about 15% to about 65%, from about 15% to about 60%, from about 15% to about 50%, from about 20% to about 65%, from about 20% to about 60%, from about 20% to about 50%, or from about 20% to about 40%.

Embodiment E20 is the process of any one of embodiments E1 to E19 wherein the feed comprises a feed gas comprising 2,4-dichlorophenol and the partial pressure of 2,4-dichlorophenol in the feed gas is at least about 0.05 kPa, at least about 0.5 kPa, or at least about 1 kPa.

Embodiment E21 is the process of any one of embodiments E1 to E19 wherein the feed comprises a feed gas comprising 2,4-dichlorophenol and the partial pressure of 2,4-dichlorophenol in the feed gas is from about 0.05 kPa to about 10 kPa, from about 0.5 kPa to about 10 kPa, or from about 1 kPa to about 10 kPa.

Embodiment E22 is the process of any one of embodiments E1 to E21 wherein the number of active aluminum sites on the zeolite catalyst is greater than about 500 µmol/g, greater than about 550 µmol/g, or greater than about 580 µmol/g.

Embodiment E23 is the process of any one of embodiments E1 to E21 wherein the number of active aluminum sites on the zeolite catalyst is from about 500 µmol/g to about 650 µmol/g, from about 550 µmol/g to about 650 µmol/g, from about 580 µmol/g to about 650 µmol/g, or from about 580 µmol/g to about 600 µmol/g.

Embodiment E24 is the process of any one of embodiments E1 to E23 wherein the zeolite catalyst is calcined at a temperature of at least about 450° C., at least about 500° C., at least about 510° C., at least about 520° C., at least about 530° C., at least about 540° C., or at least about 550° C.

Embodiment E25 is the process of any one of embodiments E1 to E23 wherein the zeolite catalyst is calcined at a temperature in the range of from about 500° C. to about 1000° C., from about 500° C. to about 900° C., from about 500° C. to about 800° C., from about 500° C. to about 700° C., from about 520° C. to about 600° C., from about 530° C. to 580° C., or from about 540° C. to 560° C.

Embodiment E26 is the process of any one of embodiments E1 to E25 wherein the molar yield of 3,4-dichlorophenol is less than about 5%, less than about 3%, less than about 1%, or between about 1% and about 5%.

Embodiment E27 is the process of any one of embodiments E1 to E26 wherein the sum of molar yields of 2-chlorophenol, 3-chlorophenol, and 4-chlorophenol is less than about 5%, less than about 3%, less than about 1%, or between about 1% and about 5%.

Embodiment E28 is the process of any one of embodiments E1 to E27 further comprising regenerating the zeolite catalyst.

Embodiment E29 is the process of any one of embodiments E1 to E28 wherein the feed comprising 2,4-dichlorophenol is supplied to the isomerization zone as a liquid.

Embodiment E30 is the process of any one of embodiments E1 to E28 wherein the feed comprising 2,4-dichlorophenol is supplied to the isomerization zone as a gas.

Embodiment E31 is the process of any one of embodiments E1 to E30 wherein the isomerization zone comprises a fixed-bed comprising the zeolite catalyst.

Embodiment E32 is the process of any one of embodiments E1 to E31 wherein the mass of catalyst divided by the mass flow rate of 2,4-dichlorophenol in the feed to the isomerization zone is at least about 1000 g·s/g, at least about 5000 g·s/g, at least about 10000 g·s/g, at least about 20000 g·s/g, at least about 50000 g·s/g, or at least about 70000 g·s/g.

Embodiment E33 is the process of any one of embodiments E1 to E31 wherein the mass of catalyst divided by the mass flow rate of 2,4-dichlorophenol in the feed to the isomerization zone is from about 1000 g·s/g to about 150000 g·s/g, from about 5000 g·s/g to about 150000 g·s/g, from about 10000 g·s/g to about 150000 g·s/g, from about 20000 g·s/g to about 150000 g·s/g, from about 20000 g·s/g to about 120000 g·s/g, from about 20000 g·s/g to about 100000 g·s/g, or from about 20000 g·s/g to about 70000 g·s/g.

Embodiment E34 is the process of any one of embodiments E1 to E33 further comprising feeding water to the isomerization zone.

Embodiment E35 is the process of embodiment E34 wherein the water is fed continuously to the isomerization zone.

Embodiment E36 is the process of embodiment E34 wherein the water is fed intermittently to the isomerization zone.

Embodiment E37 is the process of any one of embodiments E34 to E36 wherein the weight ratio of catalyst to water per hour is at least about 150:1, at least about 200:1, at least about 300:1, or at least about 400:1.

Embodiment E38 is the process of any one of embodiments E34 to E36 wherein the weight ratio of catalyst to water per hour is from about 150:1 to about 500:1, from about 150:1 to about 400:1, from about 200:1 to about 500:1, or from about 200:1 to about 400:1.

Embodiment E39 is the process of any one of embodiments E34 to E38 wherein the weight ratio of 2,4-dichlorophenol in the feed to water per hour is at least about 5:1, at least about 10:1, at least about 15:1, or at least about 20:1.

Embodiment E40 is the process of any one of embodiments E34 to E38 wherein the weight ratio of 2,4-dichlorophenol in the feed to water per hour is from about 5:1 to about 30:1, from about 5:1 to about 25:1, from about 5:1 to about 20:1, or from about 10:1 to about 20:1.

Embodiment E41 is the process of any one of embodiments E34 to E40 wherein the water is fed to the isomerization zone as steam.

Embodiment E42 is the process of embodiment E41 wherein the steam fed to the isomerization zone is at a temperature of from about 220° C. to about 550° C., from about 220° C. to about 350° C., from about 220° C. to about 300° C., from about 220° C. to about 290° C., from about 220° C. to about 285° C., from about 250° C. to about 550° C., from about 250° C. to about 350° C., from about 250° C. to about 300° C., from about 250° C. to about 290° C., from about 250° C. to about 285° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

Embodiment E43 is the process of any one of embodiments E1 to E42 wherein the zeolite catalyst has a meso-macro pore volume that is at least about 0.15 cm³/g, at least about 0.175 cm³/g, at least about 0.2 cm³/g, at least about 0.225 cm³/g, or at least about 0.25 cm³/g.

Embodiment E44 is the process of any one of embodiments E1 to E42 wherein the meso-macro pore volume of the zeolite catalyst is from about 0.15 cm$^3$/g to about 0.3 cm$^3$/g, from about 0.175 cm$^3$/g to about 0.3 cm$^3$/g, from about 0.2 cm$^3$/g to about 0.3 cm$^3$/g, from about 0.225 cm$^3$/g to about 0.3 cm$^3$/g, or from about 0.25 cm$^3$/g to about 0.3 cm$^3$/g.

Embodiment E45 is the process of any one of embodiments E1 to E44 further comprising feeding 3,4-dichlorophenol to the isomerization zone.

Embodiment E46 is the process of embodiment E45 wherein the mole ratio of 2,4-dichlorophenol to 3,4-dichlorophenol in the feed is at least about 10:1, at least about 15:1, at least about 20:1, at least about 30:1, or at least about 40:1.

Embodiment E47 is the process of embodiment E46 wherein the mole ratio of 2,4-dichlorophenol to 3,4-dichlorophenol in the feed is from about 10:1 to about 50:1, from about 10:1 to about 40:1, from about 10:1 to about 30:1, from about 10:1 to about 20:1, from about 15:1 to about 50:1, from about 15:1 to about 40:1, from about 15:1 to about 30:1, from about 15:1 to about 20:1, from about 20:1 to about 50:1, from about 20:1 to about 40:1, or from about 20:1 to about 30:1.

Embodiment E48 is the process of any one of embodiments E1 to E47 wherein the temperature of the steam in the rejuvenation step is from about 250° C. to about 375° C., from about 270° C. to about 350° C., from about 280° C. to about 325° C., or from about 290° C. to about 310° C.

Embodiment E49 is the process of any one of embodiments E1 to E48 wherein the process further comprises contacting of the feed stream comprising 2,4-dichlorophenol with the rejuvenated zeolite catalyst.

Embodiment E50 is the process of any one of embodiments E1 to E49 wherein the zeolite catalyst is contacted with steam after the contact of the feed comprising 2,4-dichlorophenol is suspended.

Embodiment E51 is the process of any one of embodiments E1 to E50 wherein the zeolite catalyst comprises a desilicated zeolite catalyst.

Embodiment E52 is the process of embodiment E51 wherein the desilicated zeolite catalyst has a meso-macro pore volume (attributable to pores that have diameters greater than 20 Å up to 2500 Å) that is at least about 50%, at least about 75%, at least about 100%, at least about 125%, at least about 150%, at least about 175%, at least about 200%, at least about 225%, at least about 250%, at least about 275%, or at least about 300% greater than the meso-macro pore volume of the initial zeolite catalyst before desilication.

Embodiment E53 is the process of embodiment E51 wherein the meso-macro pore volume (attributable to pores that have diameters greater than 20 Å up to 2500 Å) of the desilicated zeolite catalyst is from about 50% to about 500%, from about 50% to about 400%, from about 50% to about 300%, from about 100% to about 500%, from about 100% to 400%, from about 100% to about 300%, from about 200% to about 500%, from about 200% to about 400%, or from about 200% to about 300% greater than the meso-macro pore volume of the initial zeolite catalyst before desilication.

Embodiment E54 is the process of any one of embodiments E51 to E53 wherein the desilicated zeolite catalyst has a SiO$_2$/Al$_2$O$_3$ mole ratio of no greater than about 80:1, no greater than about 60:1, or no greater than about 55:1.

Embodiment E55 is the process of any one of embodiments E51 to E53 wherein the desilicated zeolite catalyst has a SiO$_2$/Al$_2$O$_3$ mole ratio of from about 23:1 to about 80:1; from about 23:1 to about 60:1; or from about 23:1 to about 55:1.

Embodiment E56 is the process of any one of embodiments E51 to E53 wherein the desilicated zeolite catalyst has a SiO$_2$/Al$_2$O$_3$ mole ratio of no greater than about 55:1 and a meso-macro pore volume that is at least about 0.15 cm$^3$/g, at least about 0.175 cm$^3$/g, at least about 0.2 cm$^3$/g, at least about 0.225 cm$^3$/g, or at least about 0.25 cm$^3$/g.

Embodiment E57 is the process of embodiment E56 wherein the meso-macro pore volume of the desilicated zeolite catalyst is from about 0.15 cm$^3$/g to about 0.3 cm$^3$/g, from about 0.175 cm$^3$/g to about 0.3 cm$^3$/g, from about 0.2 cm$^3$/g to about 0.3 cm$^3$/g, from about 0.225 cm$^3$/g to about 0.3 cm$^3$/g, or from about 0.25 cm$^3$/g to about 0.3 cm3/g.

Embodiment F1 is a process for producing 2,5-dichlorophenol, the process comprising:
hydroxylating 1,4-dichlorobenzene with an oxidizing agent in the presence of a first zeolite catalyst in a hydroxylation zone to form a hydroxylation reaction product comprising 2,5-dichlorophenol and 2,4-dichlorophenol;
separating at least a portion of the 2,4-dichlorophenol from the hydroxylation reaction product to form a fraction comprising 2,4-dichlorophenol; and
contacting the fraction comprising 2,4-dichlorophenol with a second zeolite catalyst in acid form in an isomerization zone to isomerize at least a portion of the 2,4-dichlorophenol to 2,5-dichlorophenol.

Embodiment F2 is the process of embodiment F1 wherein the oxidizing agent is selected from the group consisting of hydrogen peroxide, molecular oxygen, mixture of oxygen/hydrogen, mixture of oxygen/ammonia, and nitrous oxide.

Embodiment F3 is the process of embodiment F1 or F2 wherein the oxidizing agent comprises nitrous oxide.

Embodiment F4 is the process of any one of embodiments F1 to F3 wherein the mole ratio of oxidizing agent to 1,4-dichlorobenzene is at least about 0.25:1, at least about 0.5:1, at least about 1:1, at least about 2:1, at least about 3:1, at least about 4:1, or at least about 5:1.

Embodiment F5 is the process of any one of embodiments F1 to F3 wherein the mole ratio of oxidizing agent to 1,4-dichlorobenzene is in the range of from about 0.25:1 to about 10:1, from 0.5:1 to about 8:1, from 1:1 to about 5:1, from about 2:1 to about 10:1, from about 2:1 to about 5:1, from about 3:1 to about 10:1, or from about 3:1 to about 5:1.

Embodiment F6 is the process of any one of embodiments F1 to F5 wherein the first zeolite catalyst comprises a metal-promoted zeolite or zeolite in acid form.

Embodiment F7 is the process of any one of embodiments F1 to F6 wherein the first zeolite catalyst comprises a metal-promoted zeolite selected from the group consisting of titanium silicates, alumino-silicates, and vanadium-containing alumino-silicates.

Embodiment F8 is the process of any one of embodiments F1 to F7 wherein the first zeolite catalyst comprises at least one alumino-silicate zeolite selected from the group consisting of ZSM, Beta, Y zeolites, and mixtures thereof.

Embodiment F9 is the process of any one of embodiments F1 to F8 wherein the first zeolite catalyst comprises a metal-promoted alumino-silicate zeolite.

Embodiment F10 is the process of any one of embodiments F1 to F9 wherein the first zeolite catalyst comprises an iron-promoted alumino-silicate zeolite.

Embodiment F11 is the process of any one of embodiments F1 to F10 wherein the first zeolite catalyst comprises a Fe-ZSM-5 zeolite.

Embodiment F12 is the process of any one of embodiments F1 to F11 wherein the first zeolite catalyst comprises a HZSM-5 or HZSM-11 zeolite.

Embodiment F13 is the process of any one of embodiments F1 to F12 wherein the first zeolite catalyst comprises an iron-promoted zeolite.

Embodiment F14 is the process of embodiment F13 wherein the iron loading of the iron-promoted zeolite is less than about 2 wt. %, less than about 1 wt. %, less than about 0.8 wt. %, less than about 0.5 wt. %, or less than about 0.1 wt. % of the total catalyst weight.

Embodiment F15 is the process of embodiment F13 wherein the iron loading of the iron-promoted zeolite is in the range of from about 0.01 wt. % to about 2 wt. %, from about 0.05 wt. % to about 2 wt. %, from about 0.01 wt. % to about 1 wt. %, from about 0.05 wt. % to about 1 wt. %, from about 0.05 wt. % to about 0.5 wt. %, or from about 0.01 wt. % to about 0.2 wt. % of the total catalyst weight.

Embodiment F16 is the process of any one of embodiments F1 to F15 wherein the first zeolite catalyst has $SiO_2/Al_2O_3$ mole ratio is at least about 20:1, at least about 23:1, at least about 30:1, or at least about 50:1.

Embodiment F17 is the process of any one of embodiments F1 to F15 wherein the first zeolite catalyst has a $SiO_2/Al_2O_3$ mole ratio that is in the range of from about 20:1 to about 1000:1, from about 23:1 to about 500:1, from about 23:1 to about 350:1, from about 30:1 to about 350:1, from about 30:1 to about 280:1, from about 50:1 to about 350:1, or from about 80:1 to about 280:1.

Embodiment F18 is the process of any one of embodiments F1 to F17 wherein the first zeolite catalyst is calcined at a temperature that is at least about 500° C., at least about 600° C., at least about 700° C., at least about 800° C., or at least about 900° C.

Embodiment F19 is the process of any one of embodiments F1 to F17 wherein the first zeolite catalyst is calcined at a temperature in the range of from about 500° C. to about 1000° C., 500° C. to about 1000° C., from about 600° C. to about 1000° C., from about 700° C. to about 1000° C., from about 800° C. to about 1000° C., or from about 900° C. to about 1000° C., from about 500° C. to about 900° C., from about 500° C. to about 800° C., from about 500° C. to about 700° C., from about 520° C. to about 600° C., from about 530° C. to about 580° C., or from about 540° C. to about 560° C.

Embodiment F20 is the process of any one of embodiments F1 to F19 wherein the first zeolite catalyst is activated at a temperature that is at least about 600° C., at least about 700° C., at least about 800° C., or at least about 900° C.

Embodiment F21 is the process of any one of embodiments F1 to F20 wherein the first zeolite catalyst is activated under an argon gas at a temperature in the range of from about 800° C. to about 1000° C., or from about 850° C. to about 950° C.

Embodiment F22 is the process of any one of embodiments F1 to F20 wherein the first zeolite catalyst is activated with steam under an argon gas at a temperature in the range of from about 600° C. to about 800° C., or from about 650° C. to about 700° C.

Embodiment F23 is the process of any one of embodiments F20 to F22 wherein the first zeolite catalyst is calcined following activation and prior to use at a temperature that is at least about 600° C., at least about 700° C., at least about 800° C., or at least about 900° C.

Embodiment F24 is the process of any one of embodiments F20 to F22 wherein the first zeolite catalyst is calcined following activation and prior to use at a temperature that is in the range of from about 600° C. to about 1000° C., from about 600° C. to about 900° C., from about 700° C. to about 800° C., or from about 740° C. to about 760° C.

Embodiment F25 is the process of any one of embodiments F1 to F24 wherein a feed gas comprising the 1,4-dichlorobenzene is contacted with the first zeolite catalyst in the hydroxylation zone at a temperature in the range of from about 250° C. to about 550° C., from about 275° C. to about 500° C., from about 275° C. to about 400° C., from about 275° C. to about 375° C., from about 300° C. to about 500° C., from about 300° C. to about 450° C., or from about 350° C. to about 400° C.

Embodiment F26 is the process of any one of embodiments F1 to F24 wherein a feed gas comprising the 1,4-dichlorobenzene is contacted with the first zeolite catalyst in the hydroxylation zone at a temperature in the range of from about 350° C. to about 450° C., from about 375° C. to about 425° C., or from about 385° C. to about 415° C.

Embodiment F27 is the process of any one of embodiments F1 to F26 wherein the selectivity of the hydroxylation of 1,4-dichlorobenzene to 2,5-dichlorophenol is at least about 50%, at least about 60%, at least about 70%, at least about 80%, at least about 85%, at least about 90%, or at least about 95%.

Embodiment F28 is the process of any one of embodiments F1 to F26 wherein the selectivity of the hydroxylation of 1,4-dichlorobenzene to 2,5-dichlorophenol is from about 50% to about 99%, from about 50% to about 90%, from about 60% to about 99%, from about 60% to about 95%, from about 60% to about 90%, from about 70% to about 99%, from about 70% to about 95%, from about 70% to about 90%, or from about 75% to about 95%.

Embodiment F29 is the process of any one of embodiments F1 to F28 wherein the conversion of 1,4-dichlorobenzene is at least about 5%, at least about 10%, at least about 15%, or at least about 20%.

Embodiment F30 is the process of any one of embodiments F1 to F28 wherein the conversion of 1,4-dichlorobenzene is in the range of from about 5% to about 50%, from about 5% to about 40%, from about 5% to about 30%, or from about 20% to about 30%.

Embodiment F31 is the process of any one of embodiments F1 to F30 wherein the molar yield of 2,4-dichlorophenol in the hydroxylation reaction product is less than about 40%, less than about 35%, less than about 30%, less than about 25%, less than about 20%, less than about 15%, less than about 10%, less than about 5%, or less than about 1%.

Embodiment F32 is the process of any one of embodiments F1 to F30 wherein the molar yield of 2,4-dichlorophenol in the hydroxylation reaction product is in the range of from about 0.01% to about 40%, from about 0.01% to about 35%, from about 0.01% to about 25%, from about 0.1% to about 20%, from about 0.5% to about 40%, from about 0.5% to about 35%, from about 0.01% to about 15%, from about 0.01% to about 10%, from about 0.01% to about 5%, from about 0.1% to about 1%, from about 0.5% to about 10%, or from about 0.5% to about 5%.

Embodiment F33 is the process of any one of embodiments F1 to F32 wherein the sum of molar yields of 2-chlorophenol, 3-chlorophenol, and 4-chlorophenol in the hydroxylation reaction product is less than about 10%, or less than about 5%, less than about 1%.

Embodiment F34 is the process of any one of embodiments F1 to F32 wherein the sum of molar yields of 2-chlorophenol, 3-chlorophenol, and 4-chlorophenol in the hydroxylation reaction product is in the range of from about 0.1% and about 10% or from about 1% to about 5%.

Embodiment F35 is the process of any one of embodiments F1 to F34 further comprising regenerating the first zeolite catalyst.

Embodiment F36 is the process of any one of embodiments F1 to F35 wherein the isomerization is conducted according to the process of any one of embodiments the preceding embodiments.

Embodiment G1 is a process for producing 3,6-dichloro-2-methoxybenzoic acid comprising:
  carboxylating at least a portion of the 2,5-dichlorophenol prepared in accordance with any one of embodiments of the preceding embodiments to produce 2-hydroxy-3,6-dichlorobenzoic acid and
  methylating the 2-hydroxy-3,6-dichlorobenzoic acid to 3,6-dichloro-2-methoxybenzoic acid.

When introducing elements of the present invention or the preferred embodiments(s) thereof, the articles "a", "an", "the" and "said" are intended to mean that there are one or more of the elements. The terms "comprising", "including" and "having" are intended to be inclusive and open-ended and mean that there may be additional elements other than the listed elements and do not exclude unrecited elements or steps.

In view of the above, it will be seen that the several objects of the invention are achieved and other advantageous results attained.

As various changes could be made in the above processes without departing from the scope of the invention, it is intended that all matter contained in the above description shall be interpreted as illustrative and not in a limiting sense.

What is claimed is:

1. A process for producing 2,5-dichlorophenol, the process comprising:
  contacting a feed comprising 2,4-dichlorophenol with a desilicated zeolite catalyst in acid form in an isomerization zone to isomerize at least a portion of the 2,4-dichlorophenol to 2,5-dichlorophenol, wherein the desilicated zeolite catalyst has a meso-macro pore volume (attributable to pores that have diameters greater than 20 Å up to 2500 Å) that is at least about 50% greater than the meso-macro pore volume of the initial zeolite catalyst before desilication; or
  contacting a feed comprising 2,4-dichlorophenol with a zeolite catalyst in acid form in an isomerization zone to isomerize at least a portion of the 2,4-dichlorophenol to 2,5-dichlorophenol, wherein the zeolite catalyst has a meso-macro pore volume that is at least about 0.15 cm$^3$/g.

2. The process of claim 1 wherein the zeolite catalyst has a SiO$_2$/Al$_2$O$_3$ mole ratio of from about 23:1 to about 80:1.

3. The process of claim 1 wherein the zeolite catalyst comprises a HZSM-5 zeolite.

4. The process of claim 1 further comprising feeding water to the isomerization zone.

5. The process of claim 1 wherein the feed comprising 2,4-dichlorophenol is contacted with the desilicated zeolite catalyst in acid form and the desilicated zeolite catalyst has a meso-macro pore volume (attributable to pores that have diameters greater than 20 Å up to 2500 Å) from about 50% to about 500% greater than the meso-macro pore volume of the initial zeolite catalyst before desilication.

6. The process of claim 1 wherein the feed comprising 2,4-dichlorophenol is contacted with the zeolite catalyst in acid form having a meso-macro pore volume (attributable to pores that have diameters greater than 20 Å up to 2500 Å) of at least about 0.15 cm$^3$/g and the meso-macro pore volume of the zeolite catalyst is from about 0.15 cm$^3$/g to about 0.3 cm$^3$/g.

7. A process for producing 3,6-dichloro-2-methoxybenzoic acid comprising:
  contacting a feed comprising 2,4-dichlorophenol with a zeolite catalyst in acid form in an isomerization zone to isomerize at least a portion of the 2,4-dichlorophenol to 2,5-dichlorophenol, wherein the zeolite catalyst has a SiO$_2$/Al$_2$O$_3$ mole ratio of no greater than about 35:1;
  carboxylating at least a portion of the 2,5-dichlorophenol to produce 2-hydroxy-3,6-dichlorobenzoic acid; and
  methylating the 2-hydroxy-3,6-dichlorobenzoic acid to 3,6-dichloro-2-methoxybenzoic acid.

8. The process of claim 7 wherein the zeolite catalyst comprises at least one alumino-silicate zeolite selected from the group consisting of ZSM zeolites, Beta zeolites, Y zeolites, and mixtures thereof.

9. The process of claim 1 further comprising:
  carboxylating at least a portion of the 2,5-dichlorophenol to produce 2-hydroxy-3,6-dichlorobenzoic acid; and
  methylating the 2-hydroxy-3,6-dichlorobenzoic acid to 3,6-dichloro-2-methoxybenzoic acid.

10. A process for producing 2,5-dichlorophenol, the process comprising:
  hydroxylating 1,4-dichlorobenzene with an oxidizing agent in the presence of a first zeolite catalyst in a hydroxylation zone to form a hydroxylation reaction product comprising 2,5-dichlorophenol and 2,4-dichlorophenol;
  separating at least a portion of the 2,4-dichlorophenol from the hydroxylation reaction product to form a fraction comprising 2,4-dichlorophenol; and
  contacting the fraction comprising 2,4-dichlorophenol with a second zeolite catalyst in acid form in an isomerization zone to isomerize at least a portion of the 2,4-dichlorophenol to 2,5-dichlorophenol.

11. The process of claim 10 wherein the oxidizing agent comprises nitrous oxide.

12. The process of claim 10 wherein the first zeolite catalyst comprises an iron-promoted alumino-silicate zeolite.

13. The process of claim 12 wherein the iron loading of the iron-promoted zeolite is in the range of from about 0.01 wt. % to about 2 wt. % of the total catalyst weight.

14. The process of claim 10 wherein the first zeolite catalyst has a SiO$_2$/Al$_2$O$_3$ mole ratio that is in the range of from about 20:1 to about 1000:1.

15. The process of claim 10 wherein a feed gas comprising the 1,4-dichlorobenzene is contacted with the first zeolite catalyst in the hydroxylation zone at a temperature in the range of from about 250° C. to about 550° C.

16. The process of any one of claim 10 further comprising:
  carboxylating at least a portion of the 2,5-dichlorophenol to produce 2-hydroxy-3,6-dichlorobenzoic acid; and
  methylating the 2-hydroxy-3,6-dichlorobenzoic acid to 3,6-dichloro-2-methoxybenzoic acid.

17. The process of claim 7 wherein the SiO$_2$/Al$_2$O$_3$ mole ratio is from about 23:1 to about 35:1.

18. The process of claim 7 wherein the zeolite catalyst comprises a HZSM-5 zeolite, a HZSM-11 zeolite, or a mixture thereof.

19. The process of claim 7 further comprising feeding water to the isomerization zone.

20. The process of claim 7 wherein the isomerization is conducted at a catalyst temperature of from about 280° C. to about 325° C.

21. The process of claim 7 wherein the feed comprises a feed gas comprising 2,4-dichlorophenol and the partial pressure of 2,4-dichlorophenol in the feed gas is from about 0.05 kPa to about 10 kPa.

22. The process of claim 7 further comprising:
suspending contact of the feed comprising 2,4-dichlorophenol with the zeolite catalyst; and
contacting the zeolite catalyst with steam at a temperature from about 250° C. to about 375° C. to rejuvenate the catalyst.

23. A process for producing 2,5-dichlorophenol, the process comprising:
contacting a feed comprising 2,4-dichlorophenol and water with a zeolite catalyst in acid form in an isomerization zone to isomerize at least a portion of the 2,4-dichlorophenol to 2,5-dichlorophenol, wherein the water is fed continuously or intermittently to the isomerization zone as steam.

24. The process of claim 23 wherein the water is fed intermittently to the isomerization zone as steam.

25. The process of claim 23 wherein the water is fed continuously to the isomerization zone as steam.

26. The process of claim 23 wherein the zeolite catalyst comprises at least one alumino-silicate zeolite selected from the group consisting of ZSM zeolites, Beta zeolites, Y zeolites, and mixtures thereof.

27. The process of claim 23 wherein the zeolite catalyst comprises a ZSM zeolite.

28. The process of claim 23 wherein the zeolite catalyst comprises a HZSM-5 zeolite, a HZSM-11 zeolite or a mixture thereof.

29. The process of claim 23 wherein the isomerization is conducted at a catalyst temperature of from about 280° C. to about 325° C.

30. The process of any one of claim 23 further comprising:
carboxylating at least a portion of the 2,5-dichlorophenol to produce 2-hydroxy-3,6-dichlorobenzoic acid; and
methylating the 2-hydroxy-3,6-dichlorobenzoic acid to 3,6-dichloro-2-methoxybenzoic acid.

31. A process for producing 2,5-dichlorophenol, the process comprising:
contacting a feed comprising 2,4-dichlorophenol and water with a zeolite catalyst in acid form in an isomerization zone to isomerize at least a portion of the 2,4-dichlorophenol to 2,5-dichlorophenol, wherein the weight ratio of catalyst to water per hour is from about 150:1 to about 500:1.

32. The process of claim 31 wherein the zeolite catalyst comprises at least one alumino-silicate zeolite selected from the group consisting of ZSM zeolites, Beta zeolites, Y zeolites, and mixtures thereof.

33. The process of claim 31 wherein the zeolite catalyst comprises a ZSM zeolite.

34. The process of claim 31 wherein the zeolite catalyst comprises a HZSM-5 zeolite, a HZSM-11 zeolite or a mixture thereof.

35. The process of claim 31 wherein the isomerization is conducted at a catalyst temperature of from about 280° C. to about 325° C.

36. The process of any one of claim 31 further comprising:
carboxylating at least a portion of the 2,5-dichlorophenol to produce 2-hydroxy-3,6-dichlorobenzoic acid; and
methylating the 2-hydroxy-3,6-dichlorobenzoic acid to 3,6-dichloro-2-methoxybenzoic acid.

37. A process for producing 2,5-dichlorophenol, the process comprising:
contacting a feed comprising 2,4-dichlorophenol and water with a zeolite catalyst in acid form in an isomerization zone to isomerize at least a portion of the 2,4-dichlorophenol to 2,5-dichlorophenol, wherein the weight ratio of 2,4-dichlorophenol in the feed to water per hour is from about 5:1 to about 30:1.

38. The process of claim 37 wherein the zeolite catalyst comprises at least one alumino-silicate zeolite selected from the group consisting of ZSM zeolites, Beta zeolites, Y zeolites, and mixtures thereof.

39. The process of claim 37 wherein the zeolite catalyst comprises a ZSM zeolite.

40. The process of claim 37 wherein the zeolite catalyst comprises a HZSM-5 zeolite, a HZSM-11 zeolite or a mixture thereof.

41. The process of claim 37 wherein the isomerization is conducted at a catalyst temperature of from about 280° C. to about 325° C.

42. The process of any one of claim 37 further comprising:
carboxylating at least a portion of the 2,5-dichlorophenol to produce 2-hydroxy-3,6-dichlorobenzoic acid; and
methylating the 2-hydroxy-3,6-dichlorobenzoic acid to 3,6-dichloro-2-methoxybenzoic acid.

* * * * *